US012024553B2

(12) United States Patent
Khan et al.

(10) Patent No.: US 12,024,553 B2
(45) Date of Patent: Jul. 2, 2024

(54) DOSAGE REGIMENS FOR AND COMPOSITIONS INCLUDING ANTI-RSV ANTIBODIES

(71) Applicants: MedImmune Limited, Cambridge (GB); SANOFI PASTEUR INC., Swiftwater, PA (US)

(72) Inventors: Anis Ahmed Khan, Gaithersburg, MD (US); Vadryn Pierre, Gaithersburg, MD (US)

(73) Assignees: MedImmune Limited, Cambridge (GB); Sanofi Pasteur Inc., Swiftwater, PA (US)

( * ) Notice: Subject to any disclaimer, the term of this patent is extended or adjusted under 35 U.S.C. 154(b) by 634 days.

(21) Appl. No.: 16/859,750

(22) Filed: Apr. 27, 2020

(65) Prior Publication Data

US 2020/0347120 A1 Nov. 5, 2020

Related U.S. Application Data

(60) Provisional application No. 62/840,701, filed on Apr. 30, 2019.

(51) Int. Cl.

| | |
|---|---|
| ***A61K 39/395*** | (2006.01) |
| ***A61K 47/18*** | (2017.01) |
| ***A61K 47/26*** | (2006.01) |
| ***A61P 31/14*** | (2006.01) |
| ***C07K 16/10*** | (2006.01) |
| *A61K 39/00* | (2006.01) |

(52) U.S. Cl.

CPC ........ *C07K 16/1027* (2013.01); *A61K 47/183* (2013.01); *A61K 47/26* (2013.01); *A61P 31/14* (2018.01); *A61K 2039/545* (2013.01); *C07K 2317/21* (2013.01); *C07K 2317/76* (2013.01)

(58) Field of Classification Search

None

See application file for complete search history.

(56) References Cited

U.S. PATENT DOCUMENTS

| | | | |
|---|---|---|---|
| 8,562,996 | B2 | 10/2013 | Spits et al. |
| 8,568,726 | B2 | 10/2013 | Beaumont et al. |
| 9,283,274 | B2 | 3/2016 | Beaumont et al. |
| 9,321,831 | B2 | 4/2016 | Spits et al. |
| 10,016,496 | B2 | 7/2018 | Ulbrandt |
| 10,035,843 | B2 | 7/2018 | Beaumont et al. |
| 10,059,757 | B2 | 8/2018 | Spits et al. |
| 10,689,437 | B2 | 6/2020 | Ulbrandt et al. |
| 10,723,786 | B2 | 7/2020 | Beaumont et al. |
| 10,730,931 | B2 | 8/2020 | Spits et al. |
| 10,774,133 | B2 | 9/2020 | Lobo et al. |
| 2016/0340414 | A1 | 11/2016 | Ulbrandt et al. |
| 2020/0317754 | A1 | 10/2020 | Beaumont et al. |
| 2020/0325213 | A1 | 10/2020 | Spits et al. |
| 2020/0331989 | A1 | 10/2020 | Ulbrandt et al. |
| 2020/0339667 | A1 | 10/2020 | Lobo et al. |

FOREIGN PATENT DOCUMENTS

| | | | | |
|---|---|---|---|---|
| EP | 2238985 | A1 * | 10/2010 | ............ A61K 39/00 |
| WO | WO 2015/108967 | A2 | 7/2015 | |
| WO | WO 2018/158332 | A1 | 9/2018 | |
| WO | WO 2018/160722 | A1 | 9/2018 | |

OTHER PUBLICATIONS

Wegzyn et al., Infect Dis Ther., 2014, vol. 3, pp. 133-158 (Year: 2014).*

Altman et al., Respiratory syncytial virus in patients with congenital heart disease: a contemporary look at epidemiology and success of preoperative screening. *Pediatr Cardiol* 21, 433-438 (2000).

American Academy of Pediatrics. Committee on Infectious Diseases and Bronchiolitis Guidelines Committee. Updated guidance for palivizumab prophylaxis among infants and young children at increased risk of hospitalization for respiratory syncytial virus infection. *Pediatrics*. 134, 415-20 (2014).

American Type Culture Collection Certificate of Deposit, "ATCC No. PTA-125140" (RSV mAb 1G7 pOE) and "ATTC No. PTA-125140" (RSV mAb 1G7 YTE pOE), each deposited on Sep. 21, 2018. 2 pages.

Beckhaus et al., Down Syndrome and the Risk of Severe RSV Infection: A Meta-analysis. *Pediatrics* 142, e20180225 (2018) (published online Aug. 31, 2018).

Beeler and Van Wyke Coelingh, Neutralization epitopes of the F glycoprotein of respiratory syncytial virus: effect of mutation upon fusion function. *J Virol* 63, 2941-2950 (1989).

Blanken et al. Respiratory syncytial virus and recurrent wheeze in healthy preterm infants. *N Engl J Med.* 368(19), 1791-9 (2013).

Boyce et al., Rates of hospitalization for respiratory syncytial virus infection among children in medicaid. *J Pediatr* 137, 865-870 (2000).

Carpenter et al., Predisposition of infants with chronic lung disease to respiratory syncytial virus-induced respiratory failure: a vascular hypothesis. *Pediatr Infect Dis J* 23, S33-40 (2004).

Carbonell-Estrany et al. Motavizumab for prophylaxis of respiratory syncytial virus in high-risk children: a noninferiority trial. *Pediatrics* 125(1), e35-51 (2010).

(Continued)

*Primary Examiner* — Yunsoo Kim

(74) *Attorney, Agent, or Firm* — Finnegan, Henderson, Farabow, Garrett & Dunner, LLP

(57) ABSTRACT

In one aspect, this disclosure describes methods of treating or preventing RSV infection in a patient in need thereof. The methods include dosing regiments for administering a composition including a fixed dose of an anti-RSV monoclonal antibody or an antigen binding fragment thereof. In another aspect, this disclosure describes pharmaceutical compositions for the treatment or prevention of RSV infection. In yet another aspect, this disclosure describes a pharmaceutical unit dose including nirsevimab.

18 Claims, 32 Drawing Sheets

Specification includes a Sequence Listing.

(56) References Cited

OTHER PUBLICATIONS

Carroll et al. Increasing burden and risk factors for bronchiolitis-related medical visits in infants enrolled in a state health care insurance plan. *Pediatrics* 122(1), 58-64 (2008).

Clinicaltrials.gov NCT02878330, Study Description, "A Study to Evaluate the Safety and Efficacy of MEDI8897 for the Prevention of Medically Attended RSV LRTI in Healthy Preterm Infants (MEDI8897 Ph2b),", 2016, [online]; [retrieved on Jul. 22, 2020] from the Internet. Retrieved from the Internet :<URL:https://clinicaltrials.gov/ct2/show/study/NCT02878330>; 8 pgs.

Clinicaltrials.gov NCT02878330, Study Results, "A Study to Evaluate the Safety and Efficacy of MEDI8897 for the Prevention of Medically Attended RSV LRTI in Healthy Preterm Infants (MEDI8897 Ph2b)," 2016, [online]; [retrieved on Jul. 22, 2020] from the Internet. Retrieved from the Internet :<URL:https://clinicaltrials.gov/ct2/show/results/NCT02878330>; 22 pgs.

Coffman. Late preterm infants and risk for Rsv. *MCN Am J Matern Child Nurs*. 34(6), 378-84 (2009).

Department of Health, United Kingdom, "Joint Committee on Vaccination and Immunisation. Statement on immunisation for respiratory syncytial virus" (Jul. 9, 2011), available online https://webarchive.nationalarchives.gov.uk/20110907130105/http://www.dh.gov.uk/prod_consum_dh/groups/dh_digitalassets/@dh/@ab/documents/digitalasset/dh_120395.pdf (last accessed Feb. 10, 2021), 9 pages.

Domachowske et al., Safety, Tolerability and Pharmacokinetics of MEDI8897, an Extended Half-life Single-dose Respiratory Syncytial Virus Prefusion F-targeting Monoclonal Antibody Administered as a Single Dose to Healthy Preterm Infants, *Pediatr Infect Dis J* 37, 886-892 (Sep. 2018).

Domachowske et al., A Single Dose Monoclonal Antibody Immunoprophylaxis Strategy to Prevent Respiratory Syncytial Virus Disease in All Infants: Results of the First in Infant Study with medi8897, *Pediatrics* 141(1-MeetingAbstract):256 (Jan. 1, 2018).

European Medicines Agency. Guideline on the clinical evaluation of medicinal product indicated for the prophylaxis or treatment of respiratory syncytial virus (RSV) disease. Oct. 2018. Available from online https://www.ema.europa.eu/documents/scientific-guideline/guideline-clinical-evaluation-medicinal-products-indicated-prophylaxis-treatment-respiratory_en.pdf (last accessed Feb. 10, 2021), 20 pages.

Fenton et al., A systematic review and meta-analysis to revise the Fenton growth chart for preterm infants. *BMC Pediatr* 13, 59 (2013).

Greenough et al. Health care utilisation of infants with chronic lung disease, related to hospitalisation for RSV infection. *Arch Dis Child*. 85(6):463-8 (2001).

Griffin et al., Safety, Tolerability, and Pharmacokinetics of MEDI8897, the Respiratory Syncytial Virus Prefusion F-Targeting Monoclonal Antibody with an Extended Half-Life, in Healthy Adults. *Antimicrob Agents Chemother* 61, e01714-16 (2017).

Hall. Respiratory syncytial virus and parainfluenza virus. *New Engl J Med*. 344(25), 1917-28 (2001).

Hall et al. The burden of respiratory syncytial virus infection in young children. *New Engl J M*. 360(6), 588-98 (2009).

Hall. The burgeoning burden of respiratory syncytial virus among children. *Infect Disord Drug Targets* 12(2), 92-7 (2012).

Hall et al. Respiratory syncytial virus-associated hospitalizations among children less than 24 months of age. *Pediatrics* 132(2), e341-8 (2013).

Hothorn and Lausen, On the exact distribution of maximally selected rank statistics. *Computational Statistics & Data Analysis* 43, 121-137 (2003).

International Nonproprietary Names for Pharmaceutical Substances (INN), *WHO Drug Information*, 32(2) (2018) (excerpt: pp. 283-284 and 332-333).

Jansen et al. Influenza- and respiratory syncytial virus-associated mortality and hospitalisations. *Eur Respir J*. 30(6), 1158-66 (2007).

König et al. Prospective study of human metapneumovirus infection in children less than 3 years of age. *J Clin Microbiol*. 42(10), 4632-5 (2004).

Lanari et al., Respiratory syncytial virus infections in infants affected by primary immunodeficiency. *J Immunol Res* 2014, 850831 (2014) (6 pages).

Leader et al. Respiratory syncytial virus-coded pediatric hospitalizations, 1997 to 1999. *Pediatr Infect Dis J*. 21(7):629-32 (2002).

Lindbom et al., Perl-speaks-NONMEM (PsN)—a Perl module for NONMEM related programming. *Comput Methods Programs Biomed* 75, 85-94 (2004).

Madhi et al. Five-year cohort study of hospitalization for respiratory syncytial virus associated lower respiratory tract infection in African children. *J Clin Virol*. 36(3), 215-21 (2006).

Mazur et al., The respiratory syncytial virus vaccine landscape: lessons from the graveyard and promising candidates. *Lancet Infect Dis* 18, e295-312 (2018).

"MedImmune and Sanofi Pasteur form alliance to develop and commercialise potential next-generation respiratory syncytial virus antibody MEDI8897," Mar. 3, 2017, [online]; [retrieved on Jul. 22, 2020] from the Internet. Retrieved from the Internet:<URL:https://www.astrazeneca.com/media-centre/press-releases/2017/medimmune-and-sanofi-pasteur-form-alliance-to-develop-and-commercialise-potential-next-generation-respiratory-syncytial-virus-antibody-medi8897-030317.html#>; 5 pgs.

Meissner. Selected populations at increased risk from respiratory syncytial virus infection. *Pediatr Infect Dis J*. 22(2 Suppl):S40-4; Discussion S44-5 (2003).

Olsen et al., BMI curves for preterm infants. *Pediatrics* 135, e572-581 (2015).

Paramore et al. Outpatient RSV lower respiratory infections among high-risk infants and other pediatric populations. *Pediatr Pulmonol*. 45, 578-84 (2010).

Parrott et al. Epidemiology of respiratory syncytial virus infection in Washington, D.C. II. Infection and disease with respect to age, immunologic status, race and sex. *Am J Epidemiol*. 98(4), 289-300 (1973).

Robbie et al., A novel investigational Fc-modified humanized monoclonal antibody, motavizumab-YTE, has an extended half-life in healthy adults. *Antimicrob Agents Chemother* 57, 6147-6153 (2013).

Rose et al., Respiratory Syncytial Virus Seasonality—United States, 2014-2017. *MMWR Morb Mortal Wkly Rep* 67, 71-76 (Jan. 19, 2018).

Ruzin et al. Characterization of circulating RSV strains among subjects in the OUTSMART-RSV surveillance program during the 2016-17 winter viral season in the United States. *PLoS One* 13(7), e0200319 (Jul. 24, 2018).

Shay et al. Bronchiolitis-associated hospitalizations among US children, 1980-1996. *JAMA* 282(15), 1440-6 (1999).

Shi et al. Global, regional, and national disease burden estimates of acute lower respiratory infections due to respiratory syncytial virus in young children in 2015: a systematic review and modelling study. *Lancet* 390(10098), 946-58 (2017).

Sricharoenchai et al., Seasonality of respiratory syncytial virus—lower respiratory tract infection (RSV-LRTI) in children in developing countries. *Journal of Human Virology & Retrovirology* 3, 00076 (2016) (11 pages).

Stockman et al. Respiratory syncytial virus-associated hospitalizations among infants and young children in the United States, 1997-2006. *Pediatr Infect Dis J*. 31(1), 5-9 (2012).

Synagis Summary of Product Characteristics, (First published Apr. 12, 2009, Last Updated Aug. 20, 2020), available online at https://www.ema.europa.eu/en/documents/product-information/synagis-epar-product-information_en.pdf (last accessed Feb. 10, 2021), 61 pages.

US Food and Drug Administration. Respiratory syncytial virus infection: developing antiviral drugs for prophylaxis and treatment. Guidance for Industry: Draft Guidance. Oct. 2017. Available from: https://www.fda.gov/downloads/Drugs/GuidanceComplianceRegulatoryInformation/Guidances/UCM579756.pdf (last accessed Feb. 10, 2021), 27 pages.

(56) References Cited

OTHER PUBLICATIONS

Van Gageldonk-Lafeber et al. A case-control study of acute respiratory tract infection in general practice patients in the Netherlands. *Clin Infect Dis.* 41(4), 490-7 (2005).

Weigl et al. Incidence of respiratory syncytial virus-positive hospitalizations in Germany. *Eur J Clin Microbiol Infect Dis* 20(7), 452-9 (2001).

Zhu et al., Prevalence and Significance of Substitutions in the Fusion Protein of Respiratory Syncytial Virus Resulting in Neutralization Escape from Antibody MEDI8897. *J Infect Dis* 218, 572-580 (Mar. 30, 2018).

Zhu et al., A highly potent extended half-life antibody as a potential RSV vaccine surrogate for all infants. *Sci Transl Med* 9, eaaj1928 (2017) (11 pages).

Zou. A modified Poisson regression approach to prospective studies with binary data. *Am J Epidemiol* 159(7), 702-6 (2004).

International Search Report and Written Opinion for International Application No. PCT/US2020/030619, dated Aug. 7, 2020, 14 pages.

Dubovsky (2016) "Passive vaccination as a global strategy for preventing RSV disease in infants", Retrieved from the Internet: <URL:http://www.who.int/immunization/research/forums_and_initiatives/2_FDubovsky_Case_study_anti_RSV_mAbs_gvirfl6.pdf?ua=>], 23 pages.

cdc.gov (2023) "CDC Recommends a Powerful New Tool to Protect Infants from the Leading Cause of Hospitalization," retrieved from the internet: ,https://www.cdc.gov/media/releases/2023/p-0803-new-tool-prevent-infant-hospitalization-.html> [retrieved on Nov. 21, 2023], 2 p.

Sanofi Pasteur Inc. Beyfortus-nirsevimab injection [package insert]. (Published Jul. 2023). Available from: https://dailymed.nlm.nih.gov/dailymed/drugInfo.cfm?setid=2f08fa60-f674-432d-801b-1f9514bd9b39&audience=consumer (last accessed Nov. 16, 2023), 23 pages.

* cited by examiner

FIG. 1A

```
      D   I   Q   M   T   Q   S   P   S   S   L   S   A   A   V   G   D   R   V   T
  1 GAC ATC CAG ATG ACC CAG TCC CCC TCC TCT CTG TCT GCT GCC GTG GGC GAC AGA GTG ACC

      I   T   C   Q   A   S   Q   D   I   V   N   Y   L   N   W   Y   Q   Q   K   P
 61 ATC ACC TGT CAG GCC TCC CAG GAC ATC GTG AAC TAC CTG AAC TGG TAT CAG CAG AAG CCC

      G   K   A   P   K   L   L   I   Y   V   A   S   N   L   E   T   G   V   P   S
121 GGC AAG GCC CCC AAG CTG CTG ATC TAC GTG GCC TCC AAC CTG GAA ACC GGC GTG CCC TCC

      R   F   S   G   S   G   S   G   T   D   F   S   L   T   I   S   S   L   Q   P
181 AGA TTC TCC GGC TCT GGC TCT GGC ACC GAC TTC AGC CTG ACC ATC TCC AGC CTG CAG CCT

      E   D   V   A   T   Y   Y   C   Q   Q   Y   D   N   L   P   L   T   F   G   G
241 GAG GAC GTG GCC ACC TAC TAC TGC CAG CAG TAC GAC AAC CTG CCC CTG ACC TTT GGC GGA

      G   T   K   V   E   I   K | R   T   V   A   A   P   S   V   F   I   F   P   P
301 GGC ACC AAG GTG GAG ATC AAA|CGA ACT GTG GCT GCA CCA TCT GTC TTC ATC TTC CCC CCC

      S   D   E   Q   L   K   S   G   T   A   S   V   V   C   L   L   N   N   F   Y
361 AGC GAC GAG CAG CTG AAG AGC GGC ACC GCC TCC GTG GTG TGC CTG CTG AAC AAC TTC TAC
```

FIG. 1B

```
     P   R   E   A   K   V   Q   W   K   V   D   N   A   L   Q   S   G   N   S   Q
421  CCC CGC GAG GCC AAG GTG CAG TGG AAG GTG GAC AAC GCC CTG CAG TCC GGC AAC AGC CAG

     E   S   V   T   E   Q   D   S   K   D   S   T   Y   S   L   S   S   T   L   T
481  GAG AGC GTC ACC GAG CAG GAC AGC AAG GAC TCC ACC TAC AGC CTG AGC AGC ACC CTG ACC

     L   S   K   A   D   Y   E   K   H   K   V   Y   A   C   E   V   T   H   Q   G
541  CTG AGC AAG GCC GAC TAC GAG AAG CAC AAG GTG TAC GCC TGC GAG GTG ACC CAC CAG GGC

     L   S   S   P   V   T   K   S   F   N   R   G   E   C
601  CTG TCC AGC CCC GTG ACC AAG AGC TTC AAC AGG GGC GAG TGC
```

FIG. 2A

```
      Q   V   Q   L   V   Q   S   G   A   E   V   K   K   P   G   S   S   V   M   V
  1 CAA GTG CAG CTG GTG CAG TCT GGC GCC GAA GTG AAG AAA CCC GGC TCC TCC GTG ATG GTG

      S   C   Q   A   S   G   G   L   L   E   D   Y   I   I   N   W   V   R   Q   A
 61 TCC TGC CAG GCT TCT GGC GGC CTG CTG GAA GAT TAC ATC ATC AAC TGG GTG CGA CAG GCC

      P   G   Q   G   P   E   W   M   G   G   I   I   P   V   L   G   T   V   H   Y
121 CCA GGC CAG GGA CCT GAA TGG ATG GGC GGA ATC ATC CCC GTG CTG GGC ACC GTG CAC TAC

      G   P   K   F   Q   G   R   V   T   I   T   A   D   E   S   T   D   T   A   Y
181 GGC CCT AAG TTC CAG GGC AGA GTG ACC ATC ACC GCC GAC GAG TCT ACC GAC ACC GCC TAC

      M   E   L   S   S   L   R   S   E   D   T   A   M   Y   Y   C   A   T   E   T
241 ATG GAA CTG TCC TCC CTG CGG AGC GAG GAC ACC GCC ATG TAC TAC TGC GCC ACC GAG ACA

      A   L   V   V   S   E   T   Y   L   P   H   Y   F   D   N   W   G   Q   G   T
301 GCC CTG GTG GTG TCC GAG ACA TAC CTG CCC CAC TAC TTC GAC AAC TGG GGC CAG GGA ACC

      L   V   T   V   S   S | A   S   T   K   G   P   S   V   F   P   L   A   P   S
361 CTC GTG ACC GTC TCC TCA|GCC TCC ACC AAG GGC CCA TCG GTC TTC CCC CTG GCA CCC TCC

      S   K   S   T   S   G   G   T   A   A   L   G   C   L   V   K   D   Y   F   P
421 TCC AAG TCC ACC TCC GGC GGC ACC GCC GCT CTG GGC TGC CTG GTG AAG GAC TAC TTC CCT

      E   P   V   T   V   S   W   N   S   G   A   L   T   S   G   V   H   T   F   P
481 GAG CCT GTG ACC GTG TCC TGG AAC TCT GGC GCC CTG ACC TCT GGC GTG CAC ACC TTC CCT
```

FIG. 2B

```
     A   V   L   Q   S   S   G   L   Y   S   L   S   S   V   V   T   V   P   S   S
541  GCC GTG CTG CAG TCC TCC GGC CTG TAC TCC CTG TCC TCC GTG GTG ACA GTG CCT TCC TCC

     S   L   G   T   Q   T   Y   I   C   N   V   N   H   K   P   S   N   T   K   V
601  TCC CTG GGC ACC CAG ACC TAC ATC TGC AAC GTG AAC CAC AAG CCC AGC AAC ACC AAG GTG

     D   K   R   V   E   P   K   S   C   D   K   T   H   T   C   P   P   C   P   A
661  GAC AAG AGA GTT GAG CCC AAA TCT TGT GAC AAA ACT CAC ACA TGC CCA CCG TGC CCA GCA

     P   E   L   L   G   G   P   S   V   F   L   F   P   P   K   P   K   D   T   L
721  CCT GAA CTC CTG GGG GGA CCG TCA GTC TTT CTG TTC CCT CCT AAG CCT AAG GAC ACC CTG

     Y   I   T   R   E   P   E   V   T   C   V   V   V   D   V   S   H   E   D   P
781  TAC ATC ACC CGG GAG CCT GAA GTG ACC TGC GTG GTG GTG GAT GTG TCC CAC GAG GAC CCT

     E   V   K   F   N   W   Y   V   D   G   V   E   V   H   N   A   K   T   K   P
841  GAG GTG AAG TTC AAT TGG TAC GTG GAC GGC GTG GAG GTG CAC AAC GCC AAG ACC AAG CCT

     R   E   E   Q   Y   N   S   T   Y   R   V   V   S   V   L   T   V   L   H   Q
901  CGG GAG GAG CAG TAC AAC TCC ACC TAC CGG GTG GTG TCT GTG CTG ACC GTG CTG CAC CAG

     D   W   L   N   G   K   E   Y   K   C   K   V   S   N   K   A   L   P   A   P
961  GAC TGG CTG AAC GGC AAA GAA TAC AAG TGC AAA GTC TCC AAC AAG GCC CTG CCT GCC CCC

     I   E   K   T   I   S   K   A   K   G   Q   P   R   E   P   Q   V   Y   T   L
1021 ATC GAG AAA ACC ATC TCC AAA GCC AAA GGG CAG CCC CGA GAA CCA CAG GTG TAC ACC CTG
```

FIG. 2C

```
      P   P   S   R   E   E   M   T   K   N   Q   V   S   L   T   C   L   V   K   G
1081 CCT CCC TCC CGC GAG GAG ATG ACC AAG AAC CAG GTG TCC CTG ACC TGT CTG GTG AAG GGC

      F   Y   P   S   D   I   A   V   E   W   E   S   N   G   Q   P   E   N   N   Y
1141 TTC TAC CCT TCC GAT ATC GCC GTG GAG TGG GAG TCC AAC GGC CAG CCT GAG AAC AAC TAC

      K   T   T   P   P   V   L   D   S   D   G   S   F   F   L   Y   S   K   L   T
1201 AAG ACC ACC CCT CCT GTG CTG GAC TCC GAC GGC TCC TTC TTC CTG TAC TCC AAG CTG ACC

      V   D   K   S   R   W   Q   Q   G   N   V   F   S   C   S   V   M   H   E   A
1261 GTG GAC AAG TCC CGG TGG CAG CAG GGC AAC GTG TTC TCC TGC TCC GTG ATG CAC GAG GCT

      L   H   N   H   Y   T   Q   K   S   L   S   L   S   P   G   K
1321 CTG CAC AAC CAC TAC ACC CAG AAA AGC CTC TCC CTG TCT CCG GGT AAA
Á
```

FIG. 6A

| Subgroup | Interaction p-value | Placebo (N=484) Number of Subjects | Placebo (N=484) Observed Events | MEDI8897 (N=969) Number of Subjects | MEDI8897 (N=969) Observed Events | RRR (95% CI) |
|---|---|---|---|---|---|---|
| Hemisphere | 0.6038 | | | | | |
| Northern Hemisphere | | 329 | 25 (7.6%) | 659 | 12 (1.8%) | 76.0% (52.9%, 87.8%) |
| Southern Hemisphere | | 155 | 21 (13.5%) | 310 | 13 (4.2%) | 69.0% (39.9%, 84.1%) |
| Age at randomization | 0.2291 | | | | | |
| Age<= 3 months | | 257 | 22 (8.6%) | 516 | 7 (1.4%) | 84.2% (63.4%, 93.1%) |
| Age> 3 to <=6 months | | 153 | 16 10.5%) | 320 | 13 (4.1%) | 61.2% (21.3%, 80.8%) |
| Age> 6 months | | 74 | 8 (10.8%) | 133 | 5 (3.8%) | 65.2 (-2.5%, 88.2%) |
| Gender | 0.1165 | | | | | |
| Female | | 224 | 24 (10.7%) | 468 | 9 (1.9%) | 82.1% (62.0%, 91.5%) |
| Male | | 260 | 22 (8.5%) | 501 | 16 (3.2%) | 62.3% (29.4%, 79.8%) |
| Race | 0.8266 | | | | | |
| Caucasian | | 355 | 38 (10.7%) | 693 | 21 (3.0%) | 71.7% (52.5%, 83.1%) |
| Non-Caucasian | | 129 | 8 (6.2%) | 275 | 4 (1.5%) | 76.5% (23.5%, 92.8%) |

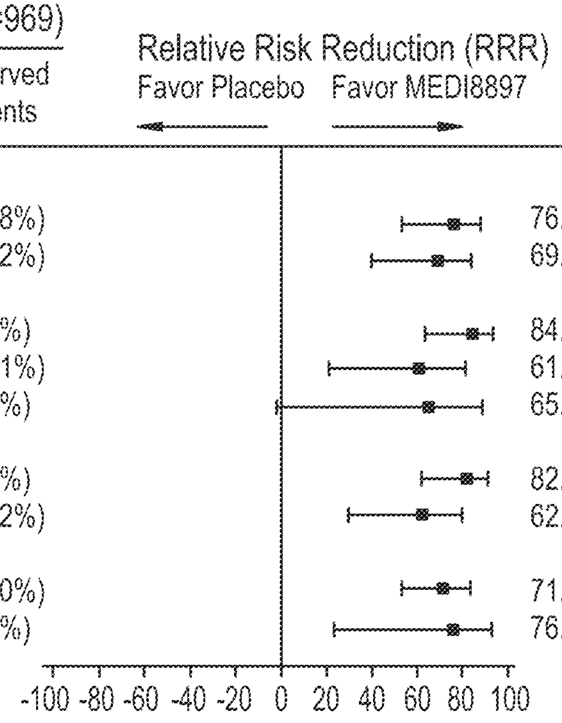

SEQUENCE LISTING

<160> NUMBER OF SEQ ID NOS: 19

<210> SEQ ID NO 1
<211> LENGTH: 214
<212> TYPE: PRT
<213> ORGANISM: artificial
<220> FEATURE:
<223> OTHER INFORMATION: nirsevimab light chain

<400> SEQUENCE: 1

Asp Ile Gln Met Thr Gln Ser Pro Ser Ser Leu Ser Ala Ala Val Gly
1               5                   10                  15

Asp Arg Val Thr Ile Thr Cys Gln Ala Ser Gln Asp Ile Val Asn Tyr
                20                  25                  30

Leu Asn Trp Tyr Gln Gln Lys Pro Gly Lys Ala Pro Lys Leu Leu Ile
            35                  40                  45

Tyr Val Ala Ser Asn Leu Glu Thr Gly Val Pro Ser Arg Phe Ser Gly
        50                  55                  60

Ser Gly Ser Gly Thr Asp Phe Ser Leu Thr Ile Ser Ser Leu Gln Pro
65                  70                  75                  80

Glu Asp Val Ala Thr Tyr Tyr Cys Gln Gln Tyr Asp Asn Leu Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

```
<210> SEQ ID NO 2
<211> LENGTH: 456
<212> TYPE: PRT
<213> ORGANISM: artificial
<220> FEATURE:
<223> OTHER INFORMATION: nirsevimab heavy chain

<400> SEQUENCE: 2

Gln Val Gln Leu Val Gln Ser Gly Ala Glu Val Lys Lys Pro Gly Ser
1               5                   10                  15

Ser Val Met Val Ser Cys Gln Ala Ser Gly Gly Leu Leu Glu Asp Tyr
            20                  25                  30

Ile Ile Asn Trp Val Arg Gln Ala Pro Gly Gln Gly Pro Glu Trp Met
        35                  40                  45

Gly Gly Ile Ile Pro Val Leu Gly Thr Val His Tyr Gly Pro Lys Phe
    50                  55                  60

Gln Gly Arg Val Thr Ile Thr Ala Asp Glu Ser Thr Asp Thr Ala Tyr
65                  70                  75                  80

Met Glu Leu Ser Ser Leu Arg Ser Glu Asp Thr Ala Met Tyr Tyr Cys
                85                  90                  95

Ala Thr Glu Thr Ala Leu Val Val Ser Glu Thr Tyr Leu Pro His Tyr
            100                 105                 110

Phe Asp Asn Trp Gly Gln Gly Thr Leu Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Arg Val
    210                 215                 220

Glu Pro Lys Ser Cys Asp Lys Thr His Thr Cys Pro Pro Cys Pro Ala
225                 230                 235                 240

Pro Glu Leu Leu Gly Gly Pro Ser Val Phe Leu Phe Pro Pro Lys Pro
                245                 250                 255

Lys Asp Thr Leu Tyr Ile Thr Arg Glu Pro Glu Val Thr Cys Val Val
            260                 265                 270

Val Asp Val Ser His Glu Asp Pro Glu Val Lys Phe Asn Trp Tyr Val
        275                 280                 285

Asp Gly Val Glu Val His Asn Ala Lys Thr Lys Pro Arg Glu Glu Gln
    290                 295                 300

Tyr Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Ala
                325                 330                 335

Leu Pro Ala Pro Ile Glu Lys Thr Ile Ser Lys Ala Lys Gly Gln Pro
            340                 345                 350

Arg Glu Pro Gln Val Tyr Thr Leu Pro Pro Ser Arg Glu Glu Met Thr
        355                 360                 365

Lys Asn Gln Val Ser Leu Thr Cys Leu Val Lys Gly Phe Tyr Pro Ser
```

-continued

```
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Lys Leu Thr Val Asp Lys Ser Arg Trp Gln Gln Gly Asn Val Phe
            420                 425                 430

Ser Cys Ser Val Met His Glu Ala Leu His Asn His Tyr Thr Gln Lys
        435                 440                 445

Ser Leu Ser Leu Ser Pro Gly Lys
    450                 455


<210> SEQ ID NO 3
<211> LENGTH: 11
<212> TYPE: PRT
<213> ORGANISM: artificial
<220> FEATURE:
<223> OTHER INFORMATION: nirsevimab light chain CDR-L1

<400> SEQUENCE: 3

Gln Ala Ser Gln Asp Ile Val Asn Tyr Leu Asn
1               5                   10


<210> SEQ ID NO 4
<211> LENGTH: 7
<212> TYPE: PRT
<213> ORGANISM: artificial
<220> FEATURE:
<223> OTHER INFORMATION: nirsevimab light chain CDR-L2

<400> SEQUENCE: 4

Val Ala Ser Asn Leu Glu Thr
1               5


<210> SEQ ID NO 5
<211> LENGTH: 9
<212> TYPE: PRT
<213> ORGANISM: artificial
<220> FEATURE:
<223> OTHER INFORMATION: nirsevimab light chain CDR-L3

<400> SEQUENCE: 5

Gln Gln Tyr Asp Asn Leu Pro Leu Thr
1               5


<210> SEQ ID NO 6
<211> LENGTH: 5
<212> TYPE: PRT
<213> ORGANISM: artificial
<220> FEATURE:
<223> OTHER INFORMATION: nirsevimab heavy chain CDR-H1

<400> SEQUENCE: 6

Asp Tyr Ile Ile Asn
1               5


<210> SEQ ID NO 7
<211> LENGTH: 17
<212> TYPE: PRT
<213> ORGANISM: artificial
<220> FEATURE:
<223> OTHER INFORMATION: nirsevimab heavy chain CDR-H2

<400> SEQUENCE: 7
```

-continued

```
Gly Ile Ile Pro Val Leu Gly Thr Val His Tyr Gly Pro Lys Phe Gln
1               5                   10                  15

Gly


<210> SEQ ID NO 8
<211> LENGTH: 17
<212> TYPE: PRT
<213> ORGANISM: artificial
<220> FEATURE:
<223> OTHER INFORMATION: nirsevimab heavy chain CDR-H3

<400> SEQUENCE: 8

Glu Thr Ala Leu Val Val Ser Glu Thr Tyr Leu Pro His Tyr Phe Asp
1               5                   10                  15

Asn


<210> SEQ ID NO 9
<211> LENGTH: 107
<212> TYPE: PRT
<213> ORGANISM: artificial
<220> FEATURE:
<223> OTHER INFORMATION: nirsevimab light chain variable region

<400> SEQUENCE: 9

Asp Ile Gln Met Thr Gln Ser Pro Ser Ser Leu Ser Ala Ala Val Gly
1               5                   10                  15

Asp Arg Val Thr Ile Thr Cys Gln Ala Ser Gln Asp Ile Val Asn Tyr
            20                  25                  30

Leu Asn Trp Tyr Gln Gln Lys Pro Gly Lys Ala Pro Lys Leu Leu Ile
        35                  40                  45

Tyr Val Ala Ser Asn Leu Glu Thr Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Val Ala Thr Tyr Tyr Cys Gln Gln Tyr Asp Asn Leu Pro Leu
                85                  90                  95

Thr Phe Gly Gly Gly Thr Lys Val Glu Ile Lys
            100                 105


<210> SEQ ID NO 10
<211> LENGTH: 126
<212> TYPE: PRT
<213> ORGANISM: artificial
<220> FEATURE:
<223> OTHER INFORMATION: nirsevimab heavy chain variable region

<400> SEQUENCE: 10

Gln Val Gln Leu Val Gln Ser Gly Ala Glu Val Lys Lys Pro Gly Ser
1               5                   10                  15

Ser Val Met Val Ser Cys Gln Ala Ser Gly Gly Leu Leu Glu Asp Tyr
            20                  25                  30

Ile Ile Asn Trp Val Arg Gln Ala Pro Gly Gln Gly Pro Glu Trp Met
        35                  40                  45

Gly Gly Ile Ile Pro Val Leu Gly Thr Val His Tyr Gly Pro Lys Phe
    50                  55                  60

Gln Gly Arg Val Thr Ile Thr Ala Asp Glu Ser Thr Asp Thr Ala Tyr
65                  70                  75                  80

Met Glu Leu Ser Ser Leu Arg Ser Glu Asp Thr Ala Met Tyr Tyr Cys
                85                  90                  95
```

-continued

```
Ala Thr Glu Thr Ala Leu Val Val Ser Glu Thr Tyr Leu Pro His Tyr
            100                 105                 110

Phe Asp Asn Trp Gly Gln Gly Thr Leu Val Thr Val Ser Ser
        115                 120                 125
```

<210> SEQ ID NO 11
<211> LENGTH: 642
<212> TYPE: DNA
<213> ORGANISM: artificial
<220> FEATURE:
<223> OTHER INFORMATION: nirsevimab light chain

<400> SEQUENCE: 11

```
gacatccaga tgacccagtc cccctcctct ctgtctgctg ccgtgggcga cagagtgacc     60

atcacctgtc aggcctccca ggacatcgtg aactacctga actggtatca gcagaagccc    120

ggcaaggccc ccaagctgct gatctacgtg gcctccaacc tggaaaccgg cgtgccctcc    180

agattctccg gctctggctc tggcaccgac ttcagcctga ccatctccag cctgcagcct    240

gaggacgtgg ccacctacta ctgccagcag tacgacaacc tgcccctgac ctttggcgga    300

ggcaccaagg tggagatcaa acgaactgtg gctgcaccat ctgtcttcat cttccccccc    360

agcgacgagc agctgaagag cggcaccgcc tccgtggtgt gcctgctgaa caacttctac    420

ccccgcgagg ccaaggtgca gtggaaggtg gacaacgccc tgcagtccgg caacagccag    480

gagagcgtca ccgagcagga cagcaaggac tccacctaca gcctgagcag caccctgacc    540

ctgagcaagg ccgactacga gaagcacaag gtgtacgcct gcgaggtgac ccaccagggc    600

ctgtccagcc ccgtgaccaa gagcttcaac aggggcgagt gc                       642
```

<210> SEQ ID NO 12
<211> LENGTH: 1368
<212> TYPE: DNA
<213> ORGANISM: artificial
<220> FEATURE:
<223> OTHER INFORMATION: nirsevimab heavy chain

<400> SEQUENCE: 12

```
caagtgcagc tggtgcagtc tggcgccgaa gtgaagaaac ccggctcctc cgtgatggtg     60

tcctgccagg cttctggcgg cctgctggaa gattacatca tcaactgggt gcgacaggcc    120

ccaggccagg gacctgaatg gatgggcgga atcatccccg tgctgggcac cgtgcactac    180

ggccctaagt tccagggcag agtgaccatc accgccgacg agtctaccga caccgcctac    240

atggaactgt cctccctgcg gagcgaggac accgccatgt actactgcgc caccgagaca    300

gccctggtgg tgtccgagac atacctgccc cactacttcg acaactgggg ccagggaacc    360

ctcgtgaccg tctcctcagc ctccaccaag ggcccatcgg tcttccccct ggcaccctcc    420

tccaagtcca cctccggcgg caccgccgct ctgggctgcc tggtgaagga ctacttccct    480

gagcctgtga ccgtgtcctg gaactctggc gccctgacct ctggcgtgca caccttccct    540

gccgtgctgc agtcctccgg cctgtactcc ctgtcctccg tggtgacagt gccttcctcc    600

tccctgggca cccagaccta catctgcaac gtgaaccaca agcccagcaa caccaaggtg    660

gacaagagag ttgagcccaa atcttgtgac aaaactcaca catgcccacc gtgcccagca    720

cctgaactcc tggggggacc gtcagtcttt ctgttccctc ctaagcctaa ggacaccctg    780

tacatcaccc gggagcctga agtgacctgc gtggtggtgg atgtgtccca cgaggaccct    840

gaggtgaagt tcaattggta cgtggacggc gtggaggtgc acaacgccaa gaccaagcct    900

cgggaggagc agtacaactc cacctaccgg gtggtgtctg tgctgaccgt gctgcaccag    960
```

-continued

```
gactggctga acggcaaaga atacaagtgc aaagtctcca acaaggccct gcctgccccc   1020

atcgagaaaa ccatctccaa agccaaaggg cagccccgag aaccacaggt gtacaccctg   1080

cctccctccc gcgaggagat gaccaagaac caggtgtccc tgacctgtct ggtgaagggc   1140

ttctaccctt ccgatatcgc cgtggagtgg gagtccaacg gccagcctga gaacaactac   1200

aagaccaccc ctcctgtgct ggactccgac ggctccttct tcctgtactc caagctgacc   1260

gtggacaagt cccggtggca gcagggcaac gtgttctcct gctccgtgat gcacgaggct   1320

ctgcacaacc actacaccca gaaaagcctc tccctgtctc cgggtaaa                1368
```

<210> SEQ ID NO 13
<211> LENGTH: 126
<212> TYPE: PRT
<213> ORGANISM: artificial
<220> FEATURE:
<223> OTHER INFORMATION: D25 heavy chain variable region

<400> SEQUENCE: 13

```
Gln Val Gln Leu Val Gln Ser Gly Ala Glu Val Lys Lys Pro Gly Ser
1               5                   10                  15

Ser Val Met Val Ser Cys Gln Ala Ser Gly Gly Pro Leu Arg Asn Tyr
            20                  25                  30

Ile Ile Asn Trp Leu Arg Gln Ala Pro Gly Gln Gly Pro Glu Trp Met
        35                  40                  45

Gly Gly Ile Ile Pro Val Leu Gly Thr Val His Tyr Ala Pro Lys Phe
    50                  55                  60

Gln Gly Arg Val Thr Ile Thr Ala Asp Glu Ser Thr Asp Thr Ala Tyr
65                  70                  75                  80

Ile His Leu Ile Ser Leu Arg Ser Glu Asp Thr Ala Met Tyr Tyr Cys
                85                  90                  95

Ala Thr Glu Thr Ala Leu Val Val Ser Thr Thr Tyr Leu Pro His Tyr
            100                 105                 110

Phe Asp Asn Trp Gly Gln Gly Thr Leu Val Thr Val Ser Ser
        115                 120                 125
```

<210> SEQ ID NO 14
<211> LENGTH: 126
<212> TYPE: PRT
<213> ORGANISM: artificial
<220> FEATURE:
<223> OTHER INFORMATION: 1F5 heavy chain variable region

<400> SEQUENCE: 14

```
Gln Val Gln Leu Val Gln Ser Gly Ala Glu Val Lys Lys Pro Gly Ser
1               5                   10                  15

Ser Val Met Val Ser Cys Gln Ala Ser Gly Gly Pro Leu Glu Asp Tyr
            20                  25                  30

Ile Ile Asn Trp Val Arg Gln Ala Pro Gly Gln Gly Pro Glu Trp Met
        35                  40                  45

Gly Gly Ile Ile Pro Val Leu Gly Thr Val His Tyr Gly Pro Lys Phe
    50                  55                  60

Gln Gly Arg Val Thr Ile Thr Ala Asp Glu Ser Thr Asp Thr Ala Tyr
65                  70                  75                  80

Met Glu Leu Ser Ser Leu Arg Ser Glu Asp Thr Ala Met Tyr Tyr Cys
                85                  90                  95

Ala Thr Glu Thr Ala Leu Val Val Ser Thr Thr Tyr Leu Pro His Tyr
            100                 105                 110
```

Phe Asp Asn Trp Gly Gln Gly Thr Leu Val Thr Val Ser Ser
115 120 125

<210> SEQ ID NO 15
<211> LENGTH: 126
<212> TYPE: PRT
<213> ORGANISM: artificial
<220> FEATURE:
<223> OTHER INFORMATION: 2D10 heavy chain variable region

<400> SEQUENCE: 15

Gln Val Gln Leu Val Gln Ser Gly Ala Glu Val Lys Lys Pro Gly Ser
1 5 10 15

Ser Val Met Val Ser Cys Gln Ala Ser Gly Gly Pro Leu Glu Asp Tyr
20 25 30

Ile Ile Asn Trp Val Arg Gln Ala Pro Gly Gln Gly Pro Glu Trp Met
35 40 45

Gly Gly Ile Ile Pro Val Leu Gly Thr Val His Tyr Gly Pro Lys Phe
50 55 60

Gln Gly Arg Val Thr Ile Thr Ala Asp Glu Ser Thr Asp Thr Ala Tyr
65 70 75 80

Met Glu Leu Ser Ser Leu Arg Ser Glu Asp Thr Ala Met Tyr Tyr Cys
85 90 95

Ala Thr Glu Thr Ala Leu Val Val Ser Thr Thr Tyr Arg Pro His Tyr
100 105 110

Phe Asp Asn Trp Gly Gln Gly Thr Leu Val Thr Val Ser Ser
115 120 125

<210> SEQ ID NO 16
<211> LENGTH: 126
<212> TYPE: PRT
<213> ORGANISM: artificial
<220> FEATURE:
<223> OTHER INFORMATION: 1G7-GLM heavy chain variable region

<400> SEQUENCE: 16

Gln Val Gln Leu Val Gln Ser Gly Ala Glu Val Lys Lys Pro Gly Ser
1 5 10 15

Ser Val Lys Val Ser Cys Lys Ala Ser Gly Gly Leu Leu Glu Asp Tyr
20 25 30

Ile Ile Asn Trp Val Arg Gln Ala Pro Gly Gln Gly Pro Glu Trp Met
35 40 45

Gly Gly Ile Ile Pro Val Leu Gly Thr Val His Tyr Gly Pro Lys Phe
50 55 60

Gln Gly Arg Val Thr Ile Thr Ala Asp Glu Ser Thr Ser Thr Ala Tyr
65 70 75 80

Met His Leu Ser Ser Leu Arg Ser Glu Asp Thr Ala Met Tyr Tyr Cys
85 90 95

Ala Arg Glu Thr Ala Leu Val Val Ser Thr Thr Tyr Leu Pro His Tyr
100 105 110

Phe Asp Asn Trp Gly Gln Gly Thr Leu Val Thr Val Ser Ser
115 120 125

<210> SEQ ID NO 17
<211> LENGTH: 126
<212> TYPE: PRT
<213> ORGANISM: artificial
<220> FEATURE:
<223> OTHER INFORMATION: B12-1 heavy chain variable region

<400> SEQUENCE: 17

Gln Val Gln Leu Val Gln Ser Gly Ala Glu Val Lys Lys Pro Gly Ser
1 5 10 15

Ser Val Lys Val Ser Cys Lys Ala Ser Gly Gly Leu Leu Glu Asp Tyr
20 25 30

Ile Ile Asn Trp Val Arg Gln Ala Pro Gly Gln Gly Pro Glu Trp Met
35 40 45

Gly Gly Ile Ile Pro Val Leu Gly Thr Val His Tyr Gly Pro Lys Phe
50 55 60

Gln Gly Arg Val Thr Ile Thr Ala Asp Glu Ser Thr Asp Thr Ala Tyr
65 70 75 80

Met His Leu Ser Ser Leu Arg Ser Glu Asp Thr Ala Met Tyr Tyr Cys
85 90 95

Ala Thr Glu Thr Ala Leu Val Val Ser Thr Thr Tyr Leu Pro His Tyr
100 105 110

Phe Asp Asn Trp Gly Gln Gly Thr Leu Val Thr Val Ser Ser
115 120 125

<210> SEQ ID NO 18
<211> LENGTH: 126
<212> TYPE: PRT
<213> ORGANISM: artificial
<220> FEATURE:
<223> OTHER INFORMATION: E3-5 heavy chain variable region

<400> SEQUENCE: 18

Gln Val Gln Leu Val Gln Ser Gly Ala Glu Val Lys Lys Pro Gly Ser
1 5 10 15

Ser Val Lys Val Ser Cys Lys Ala Ser Gly Gly Leu Leu Glu Asp Tyr
20 25 30

Ile Ile Asn Trp Val Arg Gln Ala Pro Gly Gln Gly Pro Glu Trp Met
35 40 45

Gly Gly Ile Ile Pro Val Leu Gly Thr Val His Tyr Gly Pro Lys Phe
50 55 60

Gln Gly Arg Val Thr Ile Thr Ala Asp Glu Ser Thr Ser Thr Ala Tyr
65 70 75 80

Met Glu Leu Ser Ser Leu Arg Ser Glu Asp Thr Ala Met Tyr Tyr Cys
85 90 95

Ala Thr Glu Thr Ala Leu Val Val Ser Thr Thr Tyr Leu Pro His Tyr
100 105 110

Phe Asp Asn Trp Gly Gln Gly Thr Leu Val Thr Val Ser Ser
115 120 125

<210> SEQ ID NO 19
<211> LENGTH: 126
<212> TYPE: PRT
<213> ORGANISM: artificial
<220> FEATURE:
<223> OTHER INFORMATION: E9-2 heavy chain variable region

<400> SEQUENCE: 19

Gln Val Gln Leu Val Gln Ser Gly Ala Glu Val Lys Lys Pro Gly Ser
1 5 10 15

Ser Val Lys Val Ser Cys Lys Ala Ser Gly Gly Leu Leu Glu Asp Tyr
20 25 30

Ile Ile Asn Trp Val Arg Gln Ala Pro Gly Gln Gly Pro Glu Trp Met
35 40 45

-continued

```
Gly Gly Ile Ile Pro Val Leu Gly Thr Val His Tyr Gly Pro Lys Phe
    50                  55                  60

Gln Gly Arg Val Thr Ile Thr Ala Asp Glu Ser Thr Ser Thr Ala Tyr
65                  70                  75                  80

Met His Leu Ser Ser Leu Arg Ser Glu Asp Thr Ala Met Tyr Tyr Cys
                85                  90                  95

Ala Thr Glu Thr Ala Leu Val Val Ser Thr Thr Tyr Leu Pro His Tyr
            100                 105                 110

Phe Asp Asn Trp Gly Gln Gly Thr Leu Val Thr Val Ser Ser
        115                 120                 125
```

DOSAGE REGIMENS FOR AND COMPOSITIONS INCLUDING ANTI-RSV ANTIBODIES

RELATED APPLICATIONS

This application claims the benefit of U.S. Provisional Application Ser. No. 62/840,701, filed Apr. 30, 2019, which is incorporated by reference herein.

SEQUENCE LISTING

This application contains a Sequence Listing electronically submitted to the United States Patent and Trademark Office via EFS-Web as an ASCII text file entitled “0490-000006US01_ST25.txt” having a size of 24 kilobytes and created on Apr. 27, 2020. Due to the electronic filing of the Sequence Listing, the electronically submitted Sequence Listing serves as both the paper copy required by 37 CFR § 1.821(c) and the CRF required by § 1.821(e). The information contained in the Sequence Listing is incorporated by reference herein.

BACKGROUND

Respiratory syncytial virus (RSV) is the most common cause of lower respiratory tract infections among infants and children worldwide. Nearly all children are infected with RSV during the first 2 years of life. In 2005, RSV was responsible for more than 30 million episodes of new lower respiratory tract infections among children 5 years and younger, resulting in an estimated 66,000-199,000 deaths globally.

While all children are at risk for severe lower respiratory tract infections during their primary infection, healthy term infants 3 months of age and younger account for more RSV-associated hospitalizations than any other group. Severe illness during infancy has the potential to cause both acute and long-term pulmonary sequelae, including recurrent wheezing episodes throughout childhood.

Currently, the only approved prophylaxis for RSV disease is palivizumab (Synagis; MedImmune, Gaithersburg, MD). Palivizumab is an RSV fusion (F)-specific immunoglobulin G monoclonal antibody indicated for the prevention of serious lower respiratory tract disease caused by RSV in children at high risk, including preterm infants born at 35 weeks gestational age or less. Due in part to the high cost of palivizumab prophylaxis, the most recent guidance from the American Academy of Pediatrics does not recommend it for healthy preterm infants born at or after 29 weeks gestational age. Moreover, safe and effective active vaccines remain elusive. Additional means for RSV prophylaxis, particularly for use in healthy term infants, would therefore be advantageous.

SUMMARY OF THE INVENTION

This disclosure describes methods, including a dosing regimen for an anti-RSV antibody or fragment thereof pharmaceutical compositions; and pharmaceutical unit doses for the treatment or prevention of RSV infection in a patient.

In one aspect, this disclosure describes methods of treating or preventing RSV infection in a patient in need thereof.

In some embodiments, a method of treating or preventing RSV infection in a patient in need thereof includes determining the age of the patient. In response to the patient being in the second year of life, the method includes administering a composition comprising a fixed dose of 200 milligrams (mg) of an anti-RSV monoclonal antibody or an antigen binding fragment thereof. In response to the patient being in the first year of life, the method includes determining the patient’s weight and, in response to the patient having a weight of at least 5 kilograms (kg), the method includes administering a composition comprising a fixed dose of 100 mg of an anti-RSV monoclonal antibody or an antigen binding fragment thereof.

In some embodiments, a method of treating or preventing RSV infection in a patient in need thereof includes administering a fixed dose of 200 mg of an anti-RSV monoclonal antibody or an antigen binding fragment thereof to a patient having a weight of at least 5 kg.

In some embodiments, a method of treating or preventing RSV infection in a patient in need thereof includes determining the weight of a patient and administering to a patient having a weight of at least 5 kg a fixed dose of 200 mg of an anti-RSV monoclonal antibody or an antigen binding fragment thereof or administering to a patient having a weight of up to 5 kg a fixed dose of 100 mg of an anti-RSV monoclonal antibody or an antigen binding fragment thereof.

In some embodiments, a patient having a weight of at least 5 kg has a weight of up to 10 kg, up to 15 kg, or up to 20 kg.

In some embodiments, a method of treating or preventing RSV infection in a patient in need thereof includes determining the age of the patient and administering a fixed dose of 200 mg of an anti-RSV monoclonal antibody or an antigen binding fragment thereof to a patient aged 3 months or older. In some embodiments, a method of treating or preventing RSV infection in a patient in need thereof includes determining the age of the patient and administering a fixed dose of 200 mg of an anti-RSV monoclonal antibody or an antigen binding fragment thereof to a patient aged 6 months or older.

In some embodiments, a method of treating or preventing RSV infection in a patient in need thereof includes determining the age of the patient and administering a fixed dose of 200 mg of an anti-RSV monoclonal antibody or an antigen binding fragment thereof to a patient aged 3 months or older and administering a fixed dose of 100 mg of an anti-RSV monoclonal antibody or an antigen binding fragment thereof to a patient aged up to 3 months.

In some embodiments, a method of treating or preventing RSV infection in a patient in need thereof includes determining the age of the patient and administering a fixed dose of 200 mg of an anti-RSV monoclonal antibody or an antigen binding fragment thereof to a patient aged 6 months or older and administering a fixed dose of 100 mg of an anti-RSV monoclonal antibody or an antigen binding fragment thereof to a patient aged up to 6 months.

In some embodiments, a method of treating or preventing RSV infection in a patient in need thereof includes determining whether the patient is experiencing their first or second RSV season. In response to the patient experiencing their second RSV season, the method includes administering a composition comprising a fixed dose of 200 milligrams (mg) of an anti-RSV monoclonal antibody or an antigen binding fragment thereof. In response to the patient experiencing their first RSV season, the method includes determining the patient’s weight; and in response to the patient having a weight of at least 5 kilograms (kg), administering a composition comprising a fixed dose of 100 mg of an anti-RSV monoclonal antibody or an antigen binding fragment thereof.

In some embodiments, a method of treating or preventing RSV infection in a patient in need thereof includes determining whether the patient is experiencing their first or second RSV season; and administering a fixed dose of 200 milligrams (mg) of an anti-RSV monoclonal antibody or an antigen binding fragment thereof to a patient experiencing their second RSV season.

In some embodiments, a method of treating or preventing RSV infection in a patient in need thereof includes determining whether the patient is experiencing their first or second RSV season. When the patient is experiencing their second RSV season, the method includes administering a fixed dose of 200 milligrams (mg) of an anti-RSV monoclonal antibody or an antigen binding fragment thereof to a patient. When the patient is experiencing their first RSV season, the method includes administering a fixed dose of 100 mg of an anti-RSV monoclonal antibody or an antigen binding fragment thereof to a patient, wherein the patient is experiencing their first RSV season.

In some embodiments, the anti-RSV monoclonal antibody or an antigen binding fragment thereof has an IC50 of 5.0 ng/ml or less in a neutralization assay of RSV A, or has an IC50 of 3.0 ng/ml or less in a neutralization assay of RSV B9320, or both.

In some embodiments, the anti-RSV monoclonal antibody includes nirsevimab. In some embodiments, the antigen binding fragment of the anti-RSV monoclonal antibody includes an antigen binding fragment of nirsevimab.

In some embodiments, the method may include administering an anti-RSV monoclonal antibody or an antigen binding fragment thereof in a composition. In some embodiments, the composition includes an ionic excipient, a buffer, a sugar, and/or a surfactant. In some embodiments, the ionic excipient includes L-arginine hydrochloride at a concentration of 80 mM. In some embodiments, buffer includes 30 mM L-histidine/L-histidine hydrochloride. In some embodiments, the sugar includes 120 mM sucrose. In some embodiments, the surfactant includes polysorbate-80 in a range of 0.01% (w/v) to 0.05% (w/v). In some embodiments, the composition may have a pH in a range of from 5.5 to 6.5. In some embodiments, the anti-RSV monoclonal antibody or an antigen binding fragment thereof may be present in the composition at a concentration of 100 mg/mL.

In another aspect, this disclosure describes pharmaceutical compositions for the treatment or prevention of RSV infection. In some embodiments, the pharmaceutical compositions may include 100 mg of nirsevimab, and the composition may be administered to a patient in the first year of life, the patient having a weight of at least 5 kg. In some embodiments, the pharmaceutical compositions may include 200 mg of nirsevimab, and the composition may be administered to a patient in the second year of life.

In some embodiments, after administration of the pharmaceutical composition, the patient exhibits $AUG_{0-\infty}$ of greater than 13.4 day·mg/mL.

In some embodiments, the pharmaceutical composition includes an ionic excipient, a buffer, a sugar, and/or a surfactant. In some embodiments, the ionic excipient includes L-arginine hydrochloride at a concentration of 80 mM. In some embodiments, buffer includes 30 mM L-histidine/L-histidine hydrochloride. In some embodiments, the sugar includes 120 mM sucrose. In some embodiments, the surfactant includes polysorbate-80 in a range of 0.01% (w/v) to 0.05% (w/v). In some embodiments, the composition may have a pH in a range of from 5.5 to 6.5. In some embodiments, the nirsevimab thereof may be present in the composition at a concentration of 100 mg/mL.

In yet another aspect, this disclosure describes a pharmaceutical unit dose including nirsevimab. In some embodiments, the pharmaceutical unit dose includes 100 mg of nirsevimab. In some embodiments, the pharmaceutical unit dose includes 200 mg of nirsevimab. In some embodiments, the unit dose is suitable for intramuscular administration.

In some embodiments, the pharmaceutical unit dose comprises a composition comprising nirsevimab. In some embodiments, the composition includes an ionic excipient, a buffer, a sugar, and/or a surfactant. In some embodiments, the ionic excipient includes L-arginine hydrochloride at a concentration of 80 mM. In some embodiments, buffer includes 30 mM L-histidine/L-histidine hydrochloride. In some embodiments, the sugar includes 120 mM sucrose. In some embodiments, the surfactant includes polysorbate-80 in a range of 0.01% (w/v) to 0.05% (w/v). In some embodiments, the composition may have a pH in a range of from 5.5 to 6.5. In some embodiments, the nirsevimab thereof may be present in the composition at a concentration of 100 mg/mL.

In some embodiments, the nirsevimab in the composition is stable at 2° C. to 8° C. for at least 3 months as determined by high performance size exclusion chromatography (HPSEC).

As used herein, the terms "antibody" or "immunoglobulin" refer to a tetrameric glycoprotein that consists of two heavy chains and two light chains, each comprising a variable region and a constant region. Antigen-binding portions may be produced by recombinant DNA techniques or by enzymatic or chemical cleavage of intact antibodies. The term "antibody" includes monoclonal antibodies, polyclonal antibodies, chimeric antibodies, human antibodies, and humanized antibodies.

As used herein, the terms "antibody" or "antigen binding fragment thereof" include man-made antibodies such as monoclonal antibodies (mAbs) and/or an antigen binding fragments thereof, produced by conventional hybridoma technology, by phage display, and/or recombinant technology. The terms include both intact immunoglobulin molecules including, for example, a polyclonal antibody, a monoclonal antibody (mAb), a monospecific antibody, a bispecific antibody, a polyspecific antibody, as well as portions, fragments, regions, peptides and derivatives thereof (provided by any known technique, such as, but not limited to, enzymatic cleavage, peptide synthesis, or recombinant techniques), such as, for example, immunoglobulin devoid of light chains, Fab, Fab', F $(ab')_2$, Fv, scFv, antibody fragment, diabody, Fd, CDR regions, or any portion or peptide sequence of the antibody that is capable of binding antigen or epitope. The antibody, or antigen binding fragment thereof, may be a human antibody, a humanized antibody, an animal antibody (e.g. camelid antibody), or chimeric antibody. In one embodiment, the "antigen binding fragment thereof" is a single chain antibody, a single chain variable fragment (scFv), a Fab fragment, or a $F(ab')_2$ fragment.

As used herein, the term "monoclonal antibody" refers to an antibody obtained from a population of substantially homogeneous antibodies, that is, the individual antibodies comprising the population are identical except for possible naturally occurring mutations that may be present in minor amounts.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

All headings are for the convenience of the reader and should not be used to limit the meaning of the text that follows the heading, unless so specified.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure.

Furthermore, the particular features, configurations, compositions, or characteristics may be combined in any suitable manner in one or more embodiments.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

BRIEF DESCRIPTION OF THE FIGURES

FIG. 1A-FIG. 1B show nirsevimab light chain nucleotide sequence (SEQ ID NO:11) and translation (SEQ ID NO:1). CDRs are underlined, and the division between the variable and constant regions is marked by a '|'.

FIG. 2A-FIG. 2C show nirsevimab heavy chain nucleotide sequence (SEQ ID NO:12) and translation (SEQ ID NO:2). CDRs are underlined, and the division between the variable and constant regions is marked by a '|'. Locations of three amino acid substitutions (M252Y/S254T/T256E; "YTE") in the CH2 region of the Fc domain, introduced to increase the serum half-life of nirsevimab, are circled.

FIG. 6A-FIG. 6B show a Forest plot for subgroup analysis for incidence of medically attended RSV-confirmed LRTI (observed) through 150 days post dose, as further described in Example 1. CI=confidence interval; LRTI=lower respiratory tract infection; RRR=relative risk reduction; RSV=respiratory syncytial virus.

FIG. 13A shows population predicted nirsevimab concentrations in mcg/mL. FIG. 13B shows time after dose in days. FIG. 13C shows density of the conditional weighted residuals.

FIG. 27A shows that a patient born in April (indicated by an unfilled arrow) may be experiencing their second RSV season in October of the year of their birth (while ~7 months old, indicated by a filled arrow). FIG. 27B shows a patient born in June (indicated by an unfilled arrow) may at ~7 months old (indicated by a filled arrow) be experiencing their first RSV season.

DETAILED DESCRIPTION OF ILLUSTRATIVE EMBODIMENTS

Figure 3:
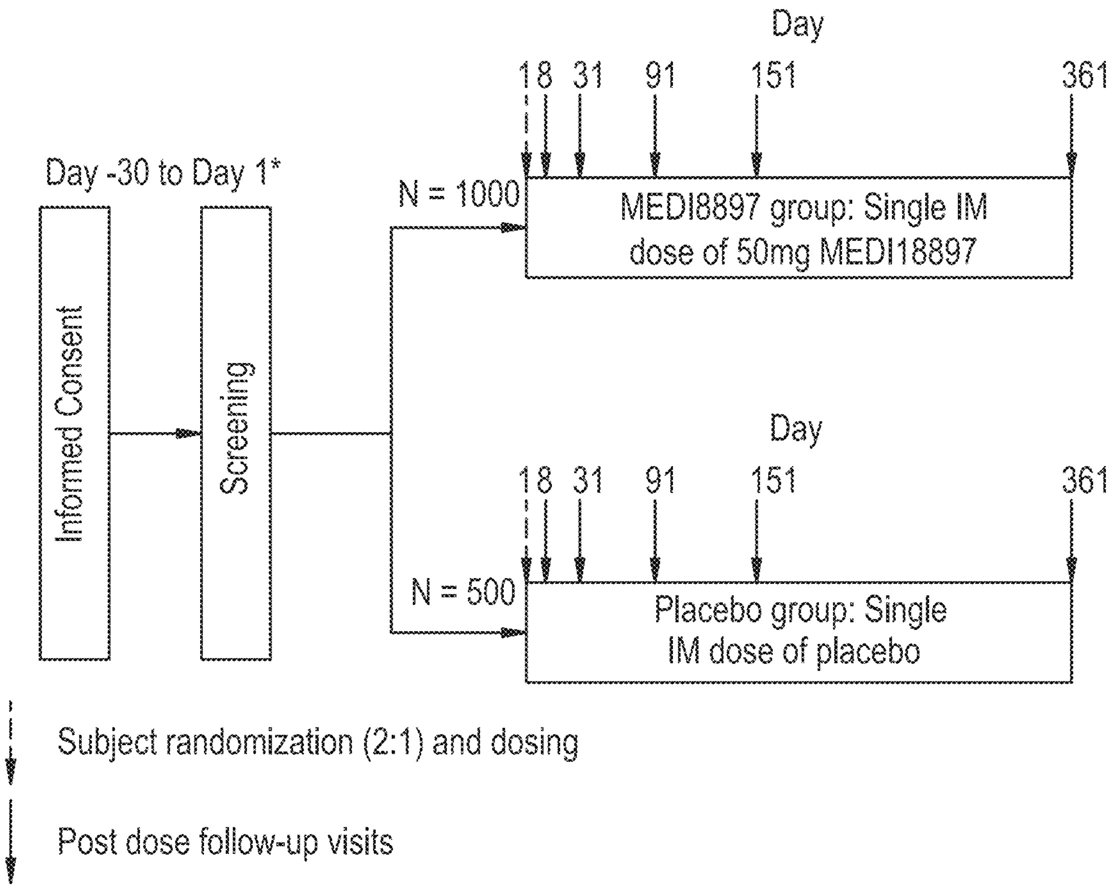
FIG. 3 shows a schematic of the Phase 2b study design, as further described in Example 1. ADA=anti-drug antibody; IM=intramuscular; LRTI=lower respiratory tract infection; PK=pharmacokinetics. PK and ADA samples were collected during screening; on Days 91, 151, 361; and at hospitalisation for LRTI. Safety assessments were performed from screening through Day 361. * Screening and Day 1 visits could occur on the same day.

This disclosure describes methods, including a dosing regimen for an anti-RSV antibody or fragment thereof; pharmaceutical compositions; and pharmaceutical unit doses for the treatment or prevention of RSV infection in a patient. In some embodiments, the anti-RSV antibody or fragment thereof includes nirsevimab (also known as MEDI8897) or a fragment of nirsevimab.

In one aspect, this disclosure describes a dosing regimen for an anti-RSV antibody or an antigen binding fragment thereof. In particular, the dosing regimen provides fixed doses for patients based on age or weight or both. In some embodiments, the anti-RSV antibody or an antigen binding fragment thereof includes a monoclonal antibody or an antigen binding fragment of a monoclonal antibody.

In some embodiments, the anti-RSV antibody or an antigen binding fragment thereof has an IC50 value of up to 10 ng/ml in an in vitro neutralization assay. In an exemplary in vitro neutralization assay, HEp-2 cells are infected with RSV and the antibody or antigen binding fragment thereof. In some embodiments, the IC50 is at least 1 ng/ml, at least 2 ng/ml, at least 3 ng/ml, at least 4 ng/ml, at least 5 ng/ml, at least 6 ng/ml, at least 7 ng/ml, or at least 8 ng/ml for RSV A subtype including, for example, RSV A2. In some embodiments, the IC50 is up to 9 ng/ml, up to 8 ng/ml, up to 7 ng/ml, up to 6 ng/ml, up to 5 ng/ml, up to 4 ng/ml, up to 3 ng/ml, or up to 2 ng/ml for RSV subtype including, for example, RSV A2. In some embodiments, the IC50 is at least 1 ng/ml, at least 2 ng/ml, at least 3 ng/ml, at least 4 ng/ml, at least 5 ng/ml, at least 6 ng/ml, at least 7 ng/ml, or at least 8 ng/ml for RSV B subtype including, for example, RSV B9320. In some embodiments, the IC50 is up to 9 ng/ml, up to 8 ng/ml, up to 7 ng/ml, up to 6 ng/ml, up to 5 ng/ml, up to 4 ng/ml, up to 3 ng/ml, or up to 2 ng/ml for RSV subtype B including, for example RSV B9320. In one embodiment, the IC50 is measured in the in vitro neutralization assay is measured as described in Example 3 and/or 4, including, for example, for RSV A2 and/or RSV B9320.

In some embodiments, the anti-RSV antibody or an antigen binding fragment thereof includes a human antibody or antigen binding fragment thereof. The use of human antibodies for human therapy may diminish the chance of side effects due to an immunological reaction in a human individual against nonhuman sequences. In another embodiment, the antibody or antigen binding fragment thereof may be humanized. In another embodiment, the anti-RSV antibody or an antigen binding fragment thereof may be a chimeric antibody or antigen binding fragment thereof.

In some embodiments, the anti-RSV antibody or an antigen binding fragment thereof may have an IgG, IgA, IgM, or IgE isotype. In one embodiment, the anti-RSV antibody or an antigen binding fragment thereof has an IgG isotope.

In some embodiments, the anti-RSV antibody or an antigen binding fragment thereof has a low or neutral isoelectric point (pI)—that is, the pH at which a protein has no net charge. In some embodiments, the pI of the anti-RSV antibody or an antigen binding fragment thereof is at pH 5.5, at least pH 6, at least pH 6.3, at least pH 6.4. In some embodiments, the pI of the anti-RSV antibody or an antigen binding fragment thereof is up to pH 6.7, up to pH 7, up to pH 7.5 In an exemplary embodiment, the anti-RSV antibody or an antigen binding fragment thereof may have a pI in the range of for example in the range about pH 5.5 to about pH 7.5. In an exemplary embodiment, the anti-RSV antibody or an antigen binding fragment thereof may have a pI in the range of pH 6.4 to pH 6.7. In one embodiment, the anti-RSV antibody or an antigen binding fragment thereof has a pI of pH 6.4.

In some embodiments, the anti-RSV antibody or an antigen binding fragment thereof includes nirsevimab (also known as MEDI8897) or an antigen binding fragment of nirsevimab. Nirsevimab is a recombinant human immunoglobulin (Ig) G1 kappa (κ monoclonal antibody derived from D25. Nirsevimab neutralizes RSV by binding to a highly conserved, neutralizing epitope on the prefusion conformation of the RSV F protein. This binding prevents the RSV F protein from mediating fusion between the viral and cellular membranes, which is an essential step for viral entry.

Nirsevimab has a full-length light chain amino acid sequence as shown in FIG. 1 (SEQ ID NO:1) and a full-length heavy chain amino acid sequence as shown in of FIG. 2 (SEQ ID NO:2).

Nirsevimab has the following CDR sequences: light chain CDR-L1 of QASQDIVNYLN (SEQ ID NO:3), light chain CDR-L2 of VASNLET (SEQ ID NO:4), light chain CDR-L3 of QQYDNLPLT (SEQ ID NO:5), heavy chain CDR-H1 of DYIIN (SEQ ID NO:6), heavy chain CDR-H2 of GIIPVLGTVHYGPKFQG (SEQ ID NO:7), and heavy chain CDR-H3 of ETALVVSETYLPHYFDN (SEQ ID NO:8). The 6 CDRS are underlined in FIG. 1 and FIG. 2.

Nirsevimab has a light chain variable sequence of amino acid residues 1 to 107 of FIG. 1 (SEQ ID NO:9) and a heavy chain variable sequence of amino acid residues 1 to 126 of FIG. 2 (SEQ ID NO:10).

Nucleotides encoding the amino acids of the full-length light chain of nirsevimab are also shown in in FIG. 1 (SEQ ID NO:11). Nucleotides encoding the amino acids of the full-length heavy chain of nirsevimab are also shown in in FIG. 2 (SEQ ID NO:12).

Nirsevimab is encoded by the RSV mAb 1G7 pOE YTE vector, deposited with the American Type Culture Collection (ATCC®), 10801 University Boulevard, Manassas, Va. 20110-2209, USA under ATCC Patent Designation PTA-125141 on Sep. 21, 2018. This deposit is in accordance with the Budapest Treaty on the International Recognition of the Deposit of Microorganisms for the Purposes of Patent Procedure.

The nirsevimab-containing vector RSV mAb 1G7 pOE was deposited with the American Type Culture Collection (ATCC®), 10801 University Boulevard, Manassas, Va. 20110-2209, USA under ATCC Patent Designation PTA-125140 on Sep. 21, 2018. This deposit is in accordance with the Budapest Treaty on the International Recognition of the Deposit of Microorganisms for the Purposes of Patent Procedure.

Nirsevimab binds a highly conserved epitope on RSV F and neutralizes a diverse panel of RSV A and B strains with >50-fold higher activity than palivizumab. At similar serum concentrations, prophylactic administration of nirsevimab is 9-fold more potent than palivizumab at reducing pulmonary viral loads by >3 logs in cotton rats infected with either RSV A or B subtypes. (Zhu et al. Sci Transl Med. 2017; 9(388). pii:eaaj1928.) The nirsevimab antibody is engineered with 3 amino acid changes (M257Y/S259T/T261E [YTE]) in the highly conserved fragment crystallizable region. This YTE modification extends the serum half-life ($t_{1/2}$) of the antibody beyond the typical 21-28 days. In a phase 1, placebo-controlled study of healthy adults, nirsevimab had a favorable safety profile and an extended mean $t_{1/2}$ of 85-117 days with increased levels of RSV-neutralizing antibodies detected in serum for more than 150 days. (Griffin et al. Antimicrob Agents Chemother. 2016; 61:e01714-e01716.)

In a phase 1b/2a dose-escalation study, healthy preterm infants with a gestational age of 32-35 weeks were randomized to receive a single intramuscular injection of nirsevimab (10 mg, 25 mg, or 50 mg) or placebo, and nirsevimab was observed to have a favorable safety profile in healthy preterm infants and to support protection from RSV for the duration of a typical 5-month season after a single 50 mg intramuscular (IM) dose. (Domachowske et al. Pediatr Infect Dis J. 2018; 37(9):886-892.)

Pharmacokinetic data in the phase 1b/2a study of nirsevimab demonstrated that a single 50 mg dose maintains antibody concentrations predictive of protection from RSV illness for at least 5 months in the majority of infants. (Domachowske et al. Pediatr Infect Dis J. 2018; 37(9):886-892.)

In some embodiments, the anti-RSV monoclonal antibody or the antigen binding fragment of the anti-RSV monoclonal antibody may include a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO:1 (the light chain sequence of nirsevimab) and/or a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO:2 (the heavy chain chain sequence of nirsevimab). In some embodiments, the anti-RSV monoclonal antibody may include a sequence comprising SEQ ID NO:1 and/or SEQ ID NO:2.

In some embodiments, the anti-RSV monoclonal antibody or the antigen binding fragment of the anti-RSV monoclonal antibody may include a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence QASQDIVNYLN (SEQ ID NO:3); a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence VASNLET (SEQ ID NO:4); a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence QQYDNLPLT (SEQ ID NO:5); a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence DYIIN (SEQ ID NO:6), a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence GIIPVLGTVHYGPKFQG (SEQ ID NO:7); and/or a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence ETALVVSETYLPHYFDN (SEQ ID NO:8).

In some embodiments, the anti-RSV monoclonal antibody or the antigen binding fragment of the anti-RSV monoclonal antibody may include QASQDIVNYLN (SEQ ID NO:3), VASNLET (SEQ ID NO:4), QQYDNLPLT (SEQ ID NO:5), DYIIN (SEQ ID NO:6), GIIPVLGTVHYGPKFQG (SEQ ID NO:7), and/or ETALVVSETYLPHYFDN (SEQ ID NO:8).

In some embodiments, the anti-RSV monoclonal antibody or the antigen binding fragment of the anti-RSV monoclonal antibody may include a light chain variable region CDR sequence or heavy chain variable region CDR sequence which differs by one amino acid from the corresponding CDR sequence of nirsevimab. In some embodiments, the anti-RSV monoclonal antibody or the antigen binding fragment of the anti-RSV monoclonal antibody may include a light chain variable region CDR sequence or heavy chain variable region CDR sequence which differs by two amino acids from the corresponding CDR sequence of nirsevimab.

In some embodiments, the anti-RSV monoclonal antibody or the antigen binding fragment of the anti-RSV monoclonal antibody may include a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence of SEQ ID NO:9 and/or a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence of SEQ ID NO:10.

Unexpectedly, and as further described in the Examples of this disclosure, population pharmacokinetic and exposure-response analyses of all the accrued pharmacokinetic data (see Griffin et al. 2017, Antimicrob Agents Chemother. 61(3), pii: e01714-16; Domachowske et al. Pediatr Infect Dis J. 2018; 37(9):886-892; and Example 1) in healthy adults and infants and the efficacy data from the Phase 2b study in infants with various degrees of prematurity (see Example 1) revealed that while a 50 mg IM dose of nirsevimab maintained nirsevimab serum concentrations at a level expected to be protective throughout the RSV season, reduced efficacy was observed in heavier infants.

A target serum concentration of 6.8 μg/mL was selected for the Phase 2b Study based on RSV challenge studies in cotton rats, a model that has been proven to be a reliable predictor of target concentrations and was used for dose selection of palivizumab. A 50 mg IM dose was selected for the Phase 2b study based on the population-PK model used to identify a dose that would maintain nirsevimab serum concentrations above 6.8 μg/mL throughout a 5 month RSV season. And, indeed, Domachowske et al. reported that pharmacokinetic data in the phase 1b/2a study of nirsevimab demonstrated that a single 50 mg dose maintains antibody serum concentrations above 6.8 μg/mL for at least 5 months in the majority of infants. (Pediatr Infect Dis J. 2018; 37(9):886-892.)

However, data analysis and modeling completed using the data obtained in the Phase 2b study using the fixed 50-mg dose resulted in a newly defined clinically efficacious $AUG_{0-\infty}$ exposure target of 13.4 day·mg/mL. While a 50-mg dose resulted in achieving the efficacious $AUC_{0-\infty}$ exposure target of 13.4 day·mg/mL in 97% of infants weighing <5 kg, a 50 mg dose was suboptimal for >59% of infants weighing ≥5 kg.

Additional modeling (see Example 2) indicates that different fixed doses (including, for example, administered by weight) would ensure an adequate dose to maintain nirsevimab serum concentrations above the target AUC demonstrated to be clinically efficacious in the Phase 2b study throughout an RSV season. Those doses are: a single fixed 50 mg IM dose for infants up to 5 kg entering their first RSV season; a single fixed 100 mg IM dose for infants having a weight of at least 5 kg entering their first RSV season; and a single fixed 200 mg IM dose for infants entering their second RSV season. The body weight of majority of the infants in the second year of life at time of dosing is expected to be in a range of 10 kg to 15 kg.

Methods of Administration

In one aspect, this disclosure describes methods of treating or preventing RSV infection in a patient in need thereof.

In some embodiments, the method includes determining the age of the patient. For example, it may be determined whether the patient is in the first year of life or in the second year of life. In some embodiments, the patient may have an age of at least 1 month, at least 3 months, at least 6 months, or at least 12 months (that is, one year). In some embodiments, the patient may have an age of up to one year, or up to two years.

In some embodiments, determining the age of the patient may include determining the gestational age of the patient. For example, in some embodiments, the patient may have a gestational age of at least 20 weeks, at least 21 weeks, at least 22 weeks, at least 23 weeks, at least 24 weeks, at least 25 weeks, at least 26 weeks, at least 27 weeks, at least 28 weeks, at least 29 weeks, at least 30 weeks, at least 31 weeks, at least 32 weeks, at least 33 weeks, at least 34 weeks, at least 35 weeks, at least 36 weeks, at least 37 weeks, at least 38 weeks, or at least 39 weeks. In an exemplary embodiment, a patient may have a gestational age of at least 29 weeks.

Figure 27A:
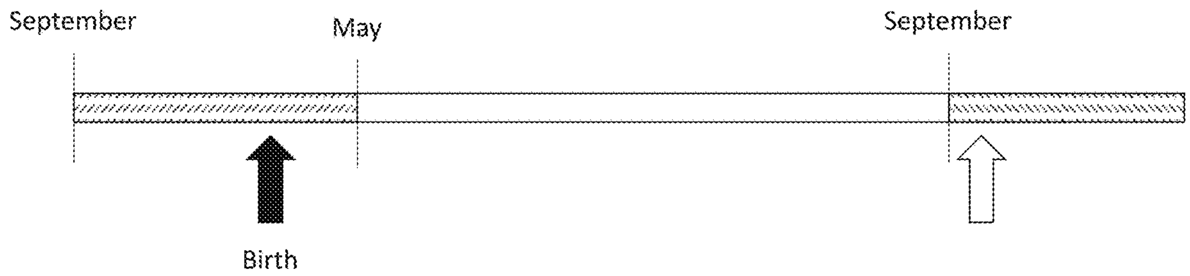
FIG. 27A-FIG. 27B show the effect of birth month on an exemplary patient's age during an RSV season in the United States.
Figure 27B:
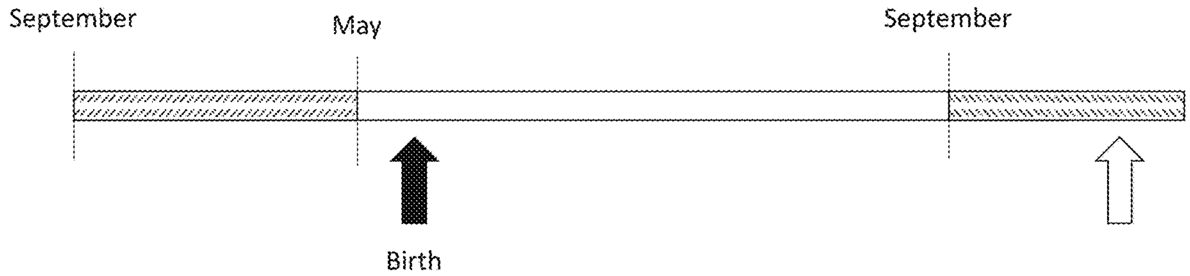

In some embodiments, the method includes determining whether the patient is experiencing the patient's first RSV season or second RSV season. For example, in the United States, where the RSV season onset ranges from mid-September to mid-November and season offset ranging from mid-April to mid-May, a patient born in April may be experiencing their second RSV season in October of the year of their birth (while ~7 months old) (see FIG. 27A) while a patient born in June may be experiencing their first RSV in December of the same year (while also ~7 months old) (see FIG. 27B).

In some embodiments, a patient experiencing the patient's first RSV season may have an age of at least 1 month, an age of at least 3 months, or an age of at least 6 months. In some embodiments, a patient experiencing the patient's second RSV season life has an age of at least 6 months and up to 2 years.

In some embodiments, the method includes determining the weight of the patient. For example, in some embodiments, the patient may have a weight of at least 4 kilograms (kg), at least 5 kg, at least 6 kg, at least 7 kg, at least 8 kg, at least 9 kg, or at least 10 kg. In some embodiments, the patient may have a weight of up to 5 kg, up to 6 kg, up to 7 kg, up to 8 kg, up to 9 kg, up to 10 kg, up to 11 kg, up to 12 kg, up to 13 kg, up to 14 kg, up to 15 kg, up to 16 kg, up to 17 kg, up to 18 kg, up to 19 kg, or up to 20 kg. In an exemplary embodiment, a patient may have a weight of at least 5 kg and up to 20 kg.

In some embodiments, the patient may have chronic lung disease (CLD). Premature babies are at increased risk for CLD due to the immaturity of their lung at birth and lung injury resulting from treatments such as use of a mechanical ventilator and/or use of a high concentration of oxygen. Infants with CLD are at particular risk of morbidity due to RSV infection. (Carpenter et al. 2004 Pediatr Infect Dis J. 23(1 Suppl):S33-40.)

In some embodiments, the patient may have congenital heart disease (CHD). In some embodiments, the CHD may include hemodynamically significant CHD which may adversely affect pulmonary blood flow. Children with hemodynamically significant CHD have a greater rate of RSV-related hospitalization (Boyce et al. 2000 J Pediatr. 137(6): 865-870), and children with CHD hospitalized for RSV are at increased risk of needing intensive care and mechanical ventilation (Altman et al. 2000 Pediatr Cardiol. 21(5):433-438).

In some embodiments, the patient may have Down's Syndrome. Children with Down's Syndrome have been reported to have a significantly higher risk of severe RSV infection than children without Down's Syndrome (Beckhaus et al., *Pediatrics* 2018; 142 (3):e20180225). In some embodiments, the patient may exhibit an immunodeficiency. The immunodeficiency may be a primary immunodeficiency or an acquired immunodeficiency. Several studies have reported that RSV infections may be more frequent or more severe in infants with congenital or acquired immunodeficiencies (including, for example, infants with HIV infections or hematopoietic stem cell and solid organs transplant recipients) than in healthy infants (see, for example, Lanari et al., *J Immunol Res.* 2014; 2014:850831).

In some embodiments, the method will include administering a composition including a fixed dose of the anti-RSV antibody or an antigen binding fragment thereof including, for example, nirsevimab or an antigen binding fragment thereof. In some embodiments, a fixed dose of the anti-RSV antibody or an antigen binding fragment thereof may include a 50 mg dose, a 100 mg dose, a 150 mg dose, a 200 mg dose, a 250 mg dose, or a 300 mg dose.

In some embodiments, the method will include administering a composition depending on the patient's age and/or weight.

For example, in an exemplary embodiment, the method may include administering a composition including a fixed dose of 200 mg of nirsevimab in response to the patient being in the second year of life.

In another exemplary embodiment, the method may include administering a composition including a fixed dose of 200 mg of nirsevimab in response to the patient having a weight of at least 5 kg.

In an exemplary embodiment, the method may include administering a composition including a fixed dose of 50 mg or 100 mg of the anti-RSV antibody or an antigen binding fragment thereof in response to the patient being in the first year of life, depending on the weight of the patient. For example, in response to the patient having a weight of up to 5 kg, a composition including a fixed dose of 50 mg of nirsevimab may be administered. Additionally or alternatively in response to the patient having a weight of at least 5 kg, a composition including a fixed dose of 100 mg of nirsevimab may be administered.

In another exemplary embodiment, the method may include administering a composition including a fixed dose of 200 mg of the anti-RSV antibody or an antigen binding fragment thereof in response to the patient aged 3 months or older.

In a further exemplary embodiment, the method may include determining the age of the patient and administering a composition including a fixed dose of 200 mg of the anti-RSV antibody or an antigen binding fragment thereof in response to the patient aged 3 months or older, administering a composition including a fixed dose of 100 mg of the anti-RSV antibody or an antigen binding fragment thereof in response to the patient aged up to 3 months.

In an additional exemplary embodiment, the method may include determining the weight of the patient and administering a composition including a fixed dose of 200 mg of the anti-RSV antibody or an antigen binding fragment thereof in response to the patient having a weight of at least 5 kg, administering a composition including a fixed dose of 100 mg of the anti-RSV antibody or an antigen binding fragment thereof in response to the patient having a weight of up to 5 kg.

In some embodiments, the method will include administering a composition depending on the RSV season the patient is experiencing (that is, first RSV season or second RSV season) and/or the patient's weight.

For example, in an exemplary embodiment, the method may include administering a composition including a fixed dose of 100 mg of nirsevimab in response to the patient experiencing their first RSV season.

In another exemplary embodiment, the method may include administering a composition including a fixed dose of 200 mg of nirsevimab in response to the patient experiencing their second RSV season.

In an additional exemplary embodiment, the method may include determining the patient's RSV season and the weight of the patient. The method may further include administering a composition including a fixed dose of 100 mg of the anti-RSV antibody or an antigen binding fragment thereof in response to the patient experiencing their first RSV season and having a weight of at least 5 kg, and administering a composition including a fixed dose of 200 mg of the anti-RSV antibody or an antigen binding fragment thereof in response to the patient experiencing their second RSV season. In some embodiments, the method may further include administering a composition including a fixed dose of 50 mg of the anti-RSV antibody or an antigen binding fragment thereof in response to the patient experiencing their first RSV season and having a weight of up to 5 kg.

In some embodiments, the dose may be administered at the beginning of the RSV season. In the United States, for example, the RSV season onset ranges from mid-September to mid-November, with the season peak ranging from late December to mid-February, and season offset ranging from mid-April to mid-May. (Rose et al. 2018 MMWR Morb Mortal Wkly Rep. 67:71-76.) Lower latitudes, for example, Florida, have an earlier RSV season onset and longer duration than most regions of the country. (Id.) In contrast, in much of the southern hemisphere, RSV epidemics typically occur between May and September but in tropical or semitropical climates, RSV outbreaks are frequently associated with the rainy season. (Sricharoenchai et al. 2016 J Hum Virol Retrovirol 3(1): 00076.)

In some embodiments, the dose may be administered parenterally. In some embodiments, the dose may be administered intramuscularly.

In some embodiments, the patient exhibits $AUC_{0-\infty}$ of greater than 10 day·mg/mL, 11 day·mg/mL, 12 day·mg/mL, 13 day·mg/mL, or 14 day·mg/mL. In an exemplary embodiment, the patient exhibits $AUC_{0-\infty}$ of greater than 13.4 day·mg/mL. As further described in Example 2, a nirsevimab dose resulting in a serum AUC greater than 13.4 day·mg/mL throughout the typical 5-month RSV season is expected to provide optimal protection against RSV in infants during the first year of life and high-risk children during the second year of life.

In some embodiments, the method includes administering a composition including the anti-RSV antibody or an antigen binding fragment thereof prophylactically, to prevent or delay the development of RSV infection. Treatment that is prophylactic may be initiated before the patient manifests symptoms of infection with RSV. Administration may be performed before, during, or after the diagnosis or development of symptoms of infection with RSV. Treatment initiated after the development of symptoms may result in decreasing the severity of the symptoms of RSV, or completely removing the symptoms of RSV.

Administration of a composition including the anti-RSV antibody or an antigen binding fragment thereof can occur before, during, and/or after other treatments. Such combination therapy can involve the administration of the anti-RSV antibody or an antigen binding fragment thereof during and/or after the use of another anti-viral compound. The administration of the anti-RSV antibody or an antigen binding fragment thereof can be separated in time from the administration of other agents by hours, days, or even weeks.

Compositions

In another aspect, the disclosure describes a composition including the anti-RSV antibody or an antigen binding fragment thereof. In some embodiments, the composition includes nirsevimab or an antigen binding fragment thereof. In some embodiments, the composition includes a therapeutically effective amount of the anti-RSV antibody or an antigen binding fragment thereof. In some embodiments, the composition may include a formulation as described in WO 2018/160722 A1. In some embodiments, the composition includes a pharmaceutical composition. A pharmaceutical composition may further include a pharmaceutically acceptable diluent, carrier, solubilizer, emulsifier, preservative, and/or adjuvant. In addition, the disclosure provides methods of treating a patient by administering such pharmaceutical composition.

In certain embodiments, acceptable materials included in the composition are nontoxic to recipients at the dosages and concentrations employed. In certain embodiments, the pharmaceutical composition may contain formulation materials for modifying, maintaining or preserving, for example, the pH, osmolality, viscosity, clarity, color, isotonicity, odor, sterility, stability, rate of dissolution, or release, adsorption, or penetration of the composition. In such embodiments, suitable formulation materials include, but are not limited to, amino acids (such as glycine, glutamine, asparagine, arginine, or lysine); antimicrobials; antioxidants (such as ascorbic acid, sodium sulfite, or sodium hydrogen-sulfite); buffers (such as borate, bicarbonate, Tris-HCl, citrates, phosphates, or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin, or hydroxypropyl-beta-cyclodextrin); fillers; monosaccharides; disaccharides; and other carbohydrates (such as glucose, sucrose, mannose, or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate-20, polysorbate-80, triton, tromethamine, lecithin, cholesterol, tyloxapal); stability enhancing agents (such as sucrose or sorbitol); tonicity enhancing agents (such as alkali metal halides, sodium or potassium chloride, mannitol sorbitol); delivery vehicles; diluents; excipients and/or pharmaceutical adjuvants.

A suitable vehicle or carrier may be water for injection, physiological saline solution or artificial cerebrospinal fluid. In some embodiments the vehicle or carrier may be supplemented with other materials common in compositions for parenteral administration. Neutral buffered saline or saline mixed with serum albumin are further exemplary vehicles.

In some embodiments, the composition includes a buffer. Exemplary buffers include Tris buffer of pH 7.0-8.5, acetate buffer of pH 4.0-5.5, or histidine buffer of pH 5.5-7.4. In some embodiments, the composition includes histidine or histidine hydrochloride or a mixture thereof. When the buffer includes an amino acid (e.g., histidine), the amino acid or amino acid salt may include the physiological active (e.g., L-form) of the amino acid. In some embodiments, a buffer may be included at a concentration of at least 20 mM, at least 30 mM, at least 40 mM, at least 50 mM, at least 60 mM, at least 70 mM, at least 80 mM, at least 90 mM, at least 100 mM, at least 110 mM, at least 120 mM, at least 130 mM, at least 140 mM, or at least 150 mM. In some embodiments, a buffer may be included at a concentration of up to 50 mM, up to 60 mM, up to 70 mM, up to 80 mM, up to 90 mM, up to 100 mM, up to 110 mM, up to 120 mM, up to 130 mM, up to 140 mM, up to 150 mM, or up to 160 mM. In an exemplary embodiment, the buffer includes 30 mM L-histidine/L-histidine hydrochloride.

In some embodiments, the composition may include a humectant including, for example, sorbitol or a suitable substitute therefor.

The formulation components may be present in concentrations that are acceptable to the site of administration. In certain embodiments, a buffer may be used to maintain the composition at physiological pH or at a slightly lower that physiological pH. In some embodiments, the pH of the composition may be at least 5, at least 5.1, at least 5.2, at least 5.3, at least 5.4, at least 5.5, at least 5.6, at least 5.7, at least 5.8, at least 5.9, at least 6.0, at least 6.1, at least 6.2, at least 6.3, at least 6.4, at least 6.5, at least 6.6, at least 6.7, at least 6.8, at least 6.9, at least 7.0, at least 7.1, at least 7.2, at least 7.3, at least 7.4, at least 7.5, at least 7.6, at least 7.7, at least 7.8, or at least 7.9. In some embodiments, the pH of the composition may be up to 5.1, up to 5.2, up to 5.3, up to 5.4, up to 5.5, up to 5.6, up to 5.7, up to 5.8, up to 5.9, up to 6.0, up to 6.1, up to 6.2, up to 6.3, up to 6.4, up to 6.5, up to 6.6, up to 6.7, up to 6.8, up to 6.9, up to 7.0, up to 7.1, up to 7.2, up to 7.3, up to 7.4, up to 7.5, up to 7.6, up to 7.7, up to 7.8, up to 7.9, or up to 8.0. In an exemplary embodiment, the pH of the composition may be in a range of from 5 to 8. In an exemplary embodiment, the pH of the composition may be in a range of from 5.5 to 6.5. In an exemplary embodiment, the pH of the composition may be 6.0.

In some embodiments, the composition may include an ionic excipient. An ionic excipient may be included in an antibody formulation for the purpose of changing the charge state of the antibody in the formulation, for changing the distribution of the antibody in the formulation, and/or for colloidally stabilizing the antibody in the formulation. In some embodiments, the ionic excipient may include a charged amino acid including, for example, lysine and/or arginine. In some embodiments, the ionic excipient may include a salt including, for example arginine hydrochloride (arginine-HCl), lysine hydrochloride (lysine-HCl), or sodium chloride (NaCl). In some embodiments, the amino acid or amino acid salt may include the physiological active (e.g., L-form) of the amino acid. In some embodiments, an ionic excipient may be included at a concentration of at least 20 mM, at least 30 mM, at least 40 mM, at least 50 mM, at least 60 mM, at least 70 mM, at least 80 mM, at least 90 mM, at least 100 mM, at least 110 mM, at least 120 mM, at least 130 mM, at least 140 mM, or at least 150 mM. In some embodiments, an ionic excipient may be included at a concentration of up to 50 mM, up to 60 mM, up to 70 mM, up to 80 mM, up to 90 mM, up to 100 mM, up to 110 mM, up to 120 mM, up to 130 mM, up to 140 mM, up to 150 mM, or up to 160 mM. In an exemplary embodiment, an ionic excipient may be present at a concentration in a range of 50 mM to 150 mM. In an exemplary embodiment, an ionic excipient may be present at a concentration in a range of 75 mM to 100 mM. In exemplary embodiments, the ionic excipient may include L-arginine hydrochloride present at a concentration of 75 mM or 80 mM.

In some embodiments, a composition that includes the anti-RSV antibody or an antigen binding fragment thereof may further include a sugar including, for example, sucrose. In some embodiments, the composition may include up to 0.5% (w/v) sucrose, up to 1% (w/v) sucrose, up to 5% (w/v) sucrose, up to 10% (w/v) sucrose, or up to 15% (w/v) sucrose. In some embodiments, a sugar may be included at a concentration of at least 50 mM, at least 60 mM, at least 70 mM, at least 80 mM, at least 90 mM, at least 100 mM, at least 110 mM, at least 120 mM, at least 130 mM, at least 140 mM, or at least 150 mM. In some embodiments, a sugar may be included at a concentration of up to 60 mM, up to 70 mM, up to 80 mM, up to 90 mM, up to 100 mM, up to 110 mM, up to 120 mM, up to 130 mM, up to 140 mM, up to 150 mM, or up to 160 mM. In an exemplary embodiment, the sugar includes sucrose at a concentration in a range of 100 mM to 140 mM. For example, the composition may include sucrose at a concentration of 120 mM.

In some embodiments, a composition that includes the anti-RSV antibody or an antigen binding fragment thereof may further include a surfactant including, for example, a polysorbate. A polysorbate may include, for example, polysorbate-20, polysorbate-40, polysorbate-60, and polysorbate-80. In some embodiments, the surfactant may be included at a concentration of 0.0001% (w/v), at least 0.001% (w/v), at least 0.002% (w/v), at least 0.01% (w/v), at least 0.02% (w/v), at least 0.03% (w/v), at least 0.04% (w/v), at least 0.05% (w/v), at least 0.06% (w/v), at least 0.07% (w/v), at least 0.08% (w/v), at least 0.09% (w/v), or at least 0.1% (w/v). In some embodiments, the surfactant may be included at a concentration of up to 0.0001% (w/v), up to 0.0005% (w/v), up to 0.001% (w/v), up to 0.002% (w/v), up to 0.01% (w/v), up to 0.02% (w/v), up to 0.03% (w/v), up to 0.04% (w/v), up to 0.05% (w/v), up to 0.06% (w/v), up to 0.07% (w/v), up to 0.08% (w/v), up to 0.09% (w/v), or up to 0.1% (w/v). For example, in an exemplary embodiment, a surfactant may be included in a concentration in a range of 0.001% (w/v) to 0.5% (w/v), in a range of 0.002% (w/v) to 0.1% (w/v), or in a range of 0.01% (w/v) to 0.05% (w/v). In an exemplary embodiment, polysorbate-80 is included in a range of 0.01% (w/v) to 0.05% (w/v). In a further exemplary embodiment, 0.02% (w/v) polysorbate-80 is included in the composition. In another exemplary embodiment, 0.04% (w/v) polysorbate-80 is included in the composition.

In some embodiments, the anti-RSV antibody or an antigen binding fragment thereof may be at a concentration of at least 50 mg/mL, at least 60 mg/mL, at least 70 mg/mL, at least 80 mg/mL, at least 90 mg/mL, at least 100 mg/mL, at least 110 mg/mL, at least 120 mg/mL, at least 130 mg/mL, at least 140 mg/mL, or at least 150 mg/mL. In some embodiments, the anti-RSV antibody or an antigen binding fragment thereof may be at a concentration of up to 60 mg/mL, up to 70 mg/mL, up to 80 mg/mL, up to 90 mg/mL, up to 100 mg/mL, up to 110 mg/mL, up to 120 mg/mL, up to 130 mg/mL, up to 140 mg/mL, up to 150 mg/mL, or up to 160 mg/mL. In an exemplary embodiment, the anti-RSV antibody or an antigen binding fragment thereof may present at a concentration in a range of 100 mg/ml to 165 mg/ml. In an exemplary embodiment, nirsevimab may be at a concentration of 100 mg/mL.

In some embodiments, the composition may be stored at −20° C. to −70° C.

In some embodiments, the composition may be stored at 2° C. to 8° C. In some embodiments, the formulations described herein are stable for extended periods of storage at room temperature or at a temperature in a range of 2° C. to 8° C., including, for example, 5° C. As used herein, room temperature is generally a temperature in the range of 22° C. to 25° C. Suitably the pharmaceutical formulations are stable after storage at a temperature in a range of 2° C. to 8° C. (including, for example, 5° C.) for at least one month, at least three months, or at least six months. As used herein, the term "stable" for a period of storage (or "stability") is used to indicate that the formulations resist aggregation, degradation, half antibody formation, and/or fragmentation. The stability of the monoclonal antibodies can be assessed by degrees of aggregation, degradation, half antibody formation or fragmentation, as measured by high performance size exclusion chromatography (HPSEC), static light scattering (SLS), Fourier Transform Infrared Spectroscopy (FTIR), circular dichroism (CD), urea unfolding techniques, intrinsic tryptophan fluorescence, differential scanning calorimetry, and/or ANS binding techniques, compared to a reference.

When parenteral administration is contemplated, the therapeutic compositions for use may be provided in the form of a pyrogen-free, parenterally acceptable aqueous solution including the anti-RSV antibody or an antigen binding fragment thereof in a pharmaceutically acceptable vehicle. In some embodiments, a particularly suitable vehicle for parenteral injection is sterile distilled water in which the antibody is formulated as a sterile, isotonic solution, properly preserved. Additionally or alternatively, formulations suitable for parenteral administration may include a sterile aqueous preparation of the anti-RSV antibody or an antigen binding fragment thereof, or dispersions of sterile powders of the anti-RSV antibody or an antigen binding fragment thereof, which are may be isotonic with the blood of the recipient. Isotonic agents that can be included in the liquid preparation include sugars, buffers, and sodium chloride. Solutions of the anti-RSV antibody or an antigen binding fragment thereof can be prepared in water, optionally mixed with a nontoxic surfactant.

Dispersions of the anti-RSV antibody or an antigen binding fragment thereof can be prepared in water, ethanol, a polyol (such as glycerol, propylene glycol, liquid polyethylene glycols, and the like), vegetable oils, glycerol esters, and mixtures thereof. The ultimate dosage form may, in some embodiments, be sterile, fluid, and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the anti-RSV antibody or an antigen binding fragment thereof, for example, by filter sterilization. Methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the anti-RSV antibody or an antigen binding fragment thereof over a prolonged period can be achieved by including agents for delaying, for example, aluminum monostearate and gelatin.

In certain embodiments, the composition can include a formulation of the anti-RSV antibody or an antigen binding fragment thereof with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the antibody.

In some embodiments, the composition may be conveniently presented in unit dosage form. For example, an exemplary pharmaceutical unit dose includes a 50 mg dose of nirsevimab; a 100 mg dose of nirsevimab, or a 200 mg dose of nirsevimab. Such a unit dose can be prepared by any of the methods well-known in the art of pharmacy. In some embodiments, the unit dose is suitable for parenteral administration including, for example, intramuscular administration

Exemplary Method Embodiments—Patient Age and Weight

1. A method of treating or preventing RSV infection in a patient in need thereof, the method comprising:

determining the age of the patient;

in response to the patient being in the second year of life, administering a composition comprising a fixed dose of 200 milligrams (mg) of an anti-RSV monoclonal antibody or an antigen binding fragment thereof;

in response to the patient being in the first year of life, determining the patient's weight; and in response to the patient having a weight of at least 5 kilograms (kg), administering a composition comprising a fixed dose of 100 mg of an anti-RSV monoclonal antibody or an antigen binding fragment thereof, wherein the anti-RSV monoclonal antibody or an antigen binding fragment thereof has an IC50 of 5.0 ng/ml or less in a neutralization assay of RSV A, or has an IC50 of 3.0 ng/ml or less in a neutralization assay of RSV B9320, or both.

2. The method of Embodiment 1, wherein the anti-RSV monoclonal antibody or the antigen binding fragment of the anti-RSV monoclonal antibody comprises a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO:1 and/or a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO:2.

3. The method of any one of the preceding Embodiments, wherein the anti-RSV monoclonal antibody or the antigen binding fragment of the anti-RSV monoclonal antibody comprises a sequence comprising SEQ ID NO:1 and/or SEQ ID NO:2.

4. The method of any one of the preceding Embodiments, wherein the anti-RSV monoclonal antibody or the antigen binding fragment of the anti-RSV monoclonal antibody comprises:

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence QASQDIVNYLN (SEQ ID NO:3);

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence VASNLET (SEQ ID NO:4);

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence QQYDNLPLT (SEQ ID NO:5);

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence DYIIN (SEQ ID NO:6);

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence GIIPVLGTVHYGPKFQG (SEQ ID NO:7); and/or a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence ETALVVSETYLPHYFDN (SEQ ID NO:8).

5. The method of any one of the preceding Embodiments, wherein the anti-RSV monoclonal antibody or the antigen binding fragment of the anti-RSV monoclonal antibody comprises QASQDIVNYLN (SEQ ID NO:3), VASNLET (SEQ ID NO:4), QQYDNLPLT (SEQ ID NO:5), DYIIN (SEQ ID NO:6), GIIPVLGTVHYGPKFQG (SEQ ID NO:7), and/or ETALVVSETYLPHYFDN (SEQ ID NO:8).

6. The method of any one of the preceding Embodiments, wherein the anti-RSV monoclonal antibody or the antigen binding fragment of the anti-RSV monoclonal antibody comprises QASQDIVNYLN (SEQ ID NO:3), VASNLET (SEQ ID NO:4), QQYDNLPLT (SEQ ID NO:5), DYIIN (SEQ ID NO:6), GIIPVLGTVHYGPKFQG (SEQ ID NO:7), and ETALVVSETYLPHYFDN (SEQ ID NO:8).

7. The method of any one of the preceding Embodiments, wherein the anti-RSV monoclonal antibody comprises a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence of SEQ ID NO:9 and/or a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence of SEQ ID NO:10.

8. The method of any one of the preceding Embodiments, wherein the anti-RSV monoclonal antibody comprises nirsevimab or wherein the antigen binding fragment of the anti-RSV monoclonal antibody comprises an antigen binding fragment of nirsevimab.

9. The method of any one of the preceding Embodiments, wherein the patient having a weight of at least 5 kg has a weight of up to 10 kg, up to 15 kg, or up to 20 kg.

10. The method of any one of the preceding Embodiments, wherein the patient being in the first year of life has an age of at least 1 month, an age of at least 3 months, or an age of at least 6 months.

11. The method of any one of the preceding Embodiments, wherein the patient in the second year of life has an age of at least one year and up to 2 years.

12. The method of any one of the preceding Embodiments, wherein the patient has a gestational age of at least 29 weeks.

13. The method of any one of the preceding Embodiments, wherein the patient exhibits $AUC_{0-\infty}$ of greater than 13.4 day·mg/mL.

14. The method of any one of the preceding Embodiments, the method comprising administering the dose at the beginning of the RSV season.

15. The method of any one of the preceding Embodiments, the method comprising administering the dose intramuscularly.

16. The method of any one of the preceding Embodiments, wherein the patient exhibits Down's Syndrome, an immunodeficiency, congenital lung disease, or congenital heart disease or a combination thereof.

17. The method of any one of the preceding Embodiments, wherein the patient exhibits congenital lung disease or congenital heart disease or both.

18. The method of any one of the preceding Embodiments, the method comprising administering the anti-RSV monoclonal antibody or an antigen binding fragment thereof in a composition comprising at least one of an ionic excipient, a buffer, a sugar, and a surfactant.

19. The method of Embodiment 28, wherein the ionic excipient comprises L-arginine hydrochloride at a concentration of 80 mM.

20. The pharmaceutical unit dose of Embodiment 18 or Embodiment 19, wherein the buffer comprises 30 mM L-histidine/L-histidine hydrochloride, the sugar comprises 120 mM sucrose, and the surfactant comprises polysorbate-80 in a range of 0.01% (w/v) to 0.05% (w/v).

21. The method of any one of Embodiments 18 to 20, wherein the anti-RSV monoclonal antibody or an antigen binding fragment thereof in the composition is stable at 2° C. to 8° C. for at least 3 months as determined by high performance size exclusion chromatography (HPSEC).

22. The method of any one of Embodiments 18 to 21, wherein the composition has a pH in a range of from 5.5 to 6.5.

23. The method of any one of Embodiments 18 to 22, wherein the the anti-RSV monoclonal antibody or an antigen binding fragment thereof is present in the composition at a concentration of 100 mg/mL.

Exemplary Method Embodiments—Patient Age or Weight

1. A method of treating or preventing RSV infection in a patient in need thereof, the method comprising administering to a patient having a weight of at least 5 kilograms (kg) a fixed dose of 200 milligrams (mg) of an anti-RSV monoclonal antibody or an antigen binding fragment thereof, wherein the anti-RSV monoclonal antibody or an antigen binding fragment thereof has an IC50 of 5.0 ng/ml or less in a neutralization assay of RSV A, or has an IC50 of 3.0 ng/ml or less in a neutralization assay of RSV B9320, or both.

2. A method of treating or preventing RSV infection in a patient in need thereof, the method comprising:

- determining the weight of a patient;
- administering to a patient having a weight of at least 5 kilograms (kg) a fixed dose of 200 milligrams (mg) of an anti-RSV monoclonal antibody or an antigen binding fragment thereof, wherein the anti-RSV monoclonal antibody or an antigen binding fragment thereof has an IC50 of 5.0 ng/ml or less in a neutralization assay of RSV A, or has an IC50 of 3.0 ng/ml or less in a neutralization assay of RSV B9320, or both;
- administering to a patient having a weight of up to 5 kg a fixed dose of 100 mg of an anti-RSV monoclonal antibody or an antigen binding fragment thereof, wherein the anti-RSV monoclonal antibody or an antigen binding fragment thereof has an IC50 of 5.0 ng/ml or less in a neutralization assay of RSV A, or has an IC50 of 3.0 ng/ml or less in a neutralization assay of RSV B9320, or both.

3. The method of either of the preceding Embodiments, wherein the patient having a weight of at least 5 kg has a weight of up to 10 kg, up to 15 kg, or up to 20 kg.

4. A method of treating or preventing RSV infection in a patient in need thereof, the method comprising

- determining the age of the patient; and
- administering a fixed dose of 200 milligrams (mg) of an anti-RSV monoclonal antibody or an antigen binding fragment thereof to a patient aged 3 months or older, wherein the anti-RSV monoclonal antibody or an antigen binding fragment thereof has an IC50 of 5.0 ng/ml or less in a neutralization assay of RSV A, or has an IC50 of 3.0 ng/ml or less in a neutralization assay of RSV B9320 or both.

5. The method of Embodiment 4, where the patient is 6 months or older.

6. The method of Embodiment 4 or Embodiment 5, wherein the patient is up to two years old.

7. A method of treating or preventing RSV infection in a patient in need thereof, the method comprising:

- determining the age of a patient;
- administering a fixed dose of 200 milligrams (mg) of an anti-RSV monoclonal antibody or an antigen binding fragment thereof to a patient aged 3 months or older;
- administering a fixed dose of 100 mg of an anti-RSV monoclonal antibody or an antigen binding fragment thereof to a patient aged up to 3 months,
- wherein the anti-RSV monoclonal antibody or an antigen binding fragment thereof has an IC50 of 5.0 ng/ml or less in a neutralization assay of RSV A, or has an IC50 of 3.0 ng/ml or less in a neutralization assay of RSV B9320, or both.

8. The method of Embodiment 7, wherein the patient aged 3 months or older is up to two years old.

9. A method of treating or preventing RSV infection in a patient in need thereof, the method comprising:

determining the age of a patient;

administering a fixed dose of 200 milligrams (mg) of an anti-RSV monoclonal antibody or an antigen binding fragment thereof to a patient aged 6 months or older;

administering a fixed dose of 100 mg of an anti-RSV monoclonal antibody or an antigen binding fragment thereof to a patient aged up to 6 months, wherein the anti-RSV monoclonal antibody or an antigen binding fragment thereof has an IC50 of 5.0 ng/ml or less in a neutralization assay of RSV A, or has an IC50 of 3.0 ng/ml or less in a neutralization assay of RSV B9320, or both.

10. The method of Embodiment 9, wherein the patient aged 6 months or older is up to two years old.

11. The method of any one of the preceding Embodiments, wherein the patient has a gestational age of at least 29 weeks.

12. The method of any one of the preceding Embodiments, wherein the patient exhibits $AUG_{0-\infty}$ of greater than 13.4 day·mg/mL.

13. The method of any one of the preceding Embodiments, the method comprising administering the dose at the beginning of the RSV season.

14. The method of any one of the preceding Embodiments, the method comprising administering the dose intramuscularly.

15. The method of any one of the preceding Embodiments, wherein the patient exhibits Down's Syndrome, an immunodeficiency, congenital lung disease, or congenital heart disease or a combination thereof.

16. The method of any one of the preceding Embodiments, wherein the patient exhibits congenital lung disease or congenital heart disease or both.

17. The method of any one of the preceding Embodiments, the method comprising administering the anti-RSV monoclonal antibody or an antigen binding fragment thereof in a composition comprising at least one of an ionic excipient, a buffer, a sugar, and a surfactant.

18. The method of Embodiment 17, wherein the ionic excipient comprises L-arginine hydrochloride at a concentration of 80 mM.

19. The method of Embodiment 17 or Embodiment 18, wherein the buffer comprises 30 mM L-histidine/L-histidine hydrochloride, the sugar comprises 120 mM sucrose, and/or the surfactant comprises polysorbate 80 in a range of 0.01% (w/v) to 0.05% (w/v).

20. The method of any one of Embodiments 18 to 19, wherein the anti-RSV monoclonal antibody or an antigen binding fragment thereof in the composition is stable at 2° C. to 8° C. for at least 3 months as determined by high performance size exclusion chromatography (HPSEC).

21. The method of any one of Embodiments 18 to 20, wherein the composition has a pH in a range of from 5.5 to 6.5.

22. The method of any one of Embodiments 18 to 21, wherein the the anti-RSV monoclonal antibody or an antigen binding fragment thereof is present in the composition at a concentration of 100 mg/mL.

23. The method of any one of the preceding Embodiments, wherein the anti-RSV monoclonal antibody or the antigen binding fragment of the anti-RSV monoclonal antibody comprises a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO:1 and/or a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical SEQ ID NO:2.

24. The method of any one of the preceding Embodiments, wherein the anti-RSV monoclonal antibody or the antigen binding fragment of the anti-RSV monoclonal antibody comprises a sequence comprising SEQ ID NO:1 and/or SEQ ID NO:2.

25. The method of any one of the preceding Embodiments, wherein the anti-RSV monoclonal antibody or the antigen binding fragment of the anti-RSV monoclonal antibody comprises:

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence QASQDIVNYLN (SEQ ID NO:3);

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence VASNLET (SEQ ID NO:4);

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence QQYDNLPLT (SEQ ID NO:5);

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence DYIIN (SEQ ID NO:6);

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence GIIPVLGTVHYGPKFQG (SEQ ID NO:7); and/or a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence ETALVVSETYLPHYFDN (SEQ ID NO:8).

26. The method of any one of the preceding Embodiments, wherein the anti-RSV monoclonal antibody or the antigen binding fragment of the anti-RSV monoclonal antibody comprises QASQDIVNYLN (SEQ ID NO:3), VASNLET (SEQ ID NO:4), QQYDNLPLT (SEQ ID NO:5), DYIIN (SEQ ID NO:6), GIIPVLGTVHYGPKFQG (SEQ ID NO:7), and/or ETALVVSETYLPHYFDN (SEQ ID NO:8).

27. The method of any one of the preceding Embodiments, wherein the anti-RSV monoclonal antibody or the antigen binding fragment of the anti-RSV monoclonal antibody comprises QASQDIVNYLN (SEQ ID NO:3), VASNLET (SEQ ID NO:4), QQYDNLPLT (SEQ ID NO:5), DYIIN (SEQ ID NO:6), GIIPVLGTVHYGPKFQG (SEQ ID NO:7), and ETALVVSETYLPHYFDN (SEQ ID NO:8).

28. The method of any one of the preceding Embodiments, wherein the anti-RSV monoclonal antibody comprises a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence of SEQ ID NO:9 and/or a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence of SEQ ID NO:10.

29. The method of any one of the preceding Embodiments, wherein the anti-RSV monoclonal antibody comprises nirsevimab or wherein the antigen binding fragment of the anti-RSV monoclonal antibody comprises an antigen binding fragment of nirsevimab.

Exemplary Method Embodiments—Patient's RSV Season and Weight

1. A method of treating or preventing RSV infection in a patient in need thereof, the method comprising:

determining whether the patient is experiencing their first or second RSV season;

in response to the patient experiencing their second RSV season, administering a composition comprising a fixed dose of 200 milligrams (mg) of an anti-RSV monoclonal antibody or an antigen binding fragment thereof;

in response to the patient experiencing their first RSV season, determining the patient's weight; and in response to the patient having a weight of at least 5 kilograms (kg), administering a composition comprising a fixed dose of 100 mg of an anti-RSV monoclonal antibody or an antigen binding fragment thereof, wherein the anti-RSV monoclonal antibody or an antigen binding fragment thereof has an IC50 of 5.0 ng/ml or less in a neutralization assay of RSV A, or has an IC50 of 3.0 ng/ml or less in a neutralization assay of RSV B9320, or both.

2. The method of Embodiment 1, wherein the anti-RSV monoclonal antibody or the antigen binding fragment of the anti-RSV monoclonal antibody comprises a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO:1 and/or a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO:2.

3. The method of any one of the preceding Embodiments, wherein the anti-RSV monoclonal antibody or the antigen binding fragment of the anti-RSV monoclonal antibody comprises a sequence comprising SEQ ID NO:1 and/or SEQ ID NO:2.

4. The method of any one of the preceding Embodiments, wherein the anti-RSV monoclonal antibody or the antigen binding fragment of the anti-RSV monoclonal antibody comprises:

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence QASQDIVNYLN (SEQ ID NO:3);

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence VASNLET (SEQ ID NO:4);

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence QQYDNLPLT (SEQ ID NO:5);

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence DYIIN (SEQ ID NO:6);

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence GIIPVLGTVHYGPKFQG (SEQ ID NO:7); and/or a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence ETALVVSETYLPHYFDN (SEQ ID NO:8).

5. The method of any one of the preceding Embodiments, wherein the anti-RSV monoclonal antibody or the antigen binding fragment of the anti-RSV monoclonal antibody comprises QASQDIVNYLN (SEQ ID NO:3), VASNLET (SEQ ID NO:4), QQYDNLPLT (SEQ ID NO:5), DYIIN (SEQ ID NO:6), GIIPVLGTVHYGPKFQG (SEQ ID NO:7), and/or ETALVVSETYLPHYFDN (SEQ ID NO:8).

6. The method of any one of the preceding Embodiments, wherein the anti-RSV monoclonal antibody or the antigen binding fragment of the anti-RSV monoclonal antibody comprises QASQDIVNYLN (SEQ ID NO:3), VASNLET (SEQ ID NO:4), QQYDNLPLT (SEQ ID NO:5), DYIIN (SEQ ID NO:6), GIIPVLGTVHYGPKFQG (SEQ ID NO:7), and ETALVVSETYLPHYFDN (SEQ ID NO:8).

7. The method of any one of the preceding Embodiments, wherein the anti-RSV monoclonal antibody comprises a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence of SEQ ID NO:9 and/or a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence of SEQ ID NO:10.

8. The method of any one of the preceding Embodiments, wherein the anti-RSV monoclonal antibody comprises nirsevimab or wherein the antigen binding fragment of the anti-RSV monoclonal antibody comprises an antigen binding fragment of nirsevimab.

9. The method of any one of the preceding Embodiments, wherein the patient having a weight of at least 5 kg has a weight of up to 10 kg, up to 15 kg, or up to 20 kg.

10. The method of any one of the preceding Embodiments, wherein the patient experiencing their first RSV season has an age of at least 1 month, an age of at least 3 months, or an age of at least 6 months.

11. The method of any one of the preceding Embodiments, wherein the patient experiencing their second RSV season life has an age of at least 6 months and up to 2 years.

12. The method of any one of the preceding Embodiments, wherein the patient has a gestational age of at least 29 weeks.

13. The method of any one of the preceding Embodiments, wherein the patient exhibits $AUC_{0-\infty}$ of greater than 13.4 day·mg/mL.

14. The method of any one of the preceding Embodiments, the method comprising administering the dose at the beginning of the RSV season.

15. The method of any one of the preceding Embodiments, the method comprising administering the dose intramuscularly.

16. The method of any one of the preceding Embodiments, wherein the patient exhibits Down's Syndrome, immunodeficiency, congenital lung disease, or congenital heart disease or a combination thereof.

17. The method of any one of the preceding Embodiments, wherein the patient exhibits congenital lung disease or congenital heart disease or both.

18. The method of any one of the preceding Embodiments, the method comprising administering the anti-RSV monoclonal antibody or an antigen binding fragment thereof in a composition comprising at least one of an ionic excipient, a buffer, a sugar, and a surfactant.

19. The method of Embodiment 28, wherein the ionic excipient comprises L-arginine hydrochloride at a concentration of 80 mM.

20. The pharmaceutical unit dose of Embodiment 18 or Embodiment 19, wherein the buffer comprises 30 mM L-histidine/L-histidine hydrochloride, the sugar comprises 120 mM sucrose, and the surfactant comprises polysorbate-80 in a range of 0.01% (w/v) to 0.05% (w/v).

21. The method of any one of Embodiments 18 to 20, wherein the anti-RSV monoclonal antibody or an antigen binding fragment thereof in the composition is stable at 2° C. to 8° C. for at least 3 months as determined by high performance size exclusion chromatography (HPSEC).

22. The method of any one of Embodiments 18 to 21, wherein the composition has a pH in a range of from 5.5 to 6.5.

23. The method of any one of Embodiments 18 to 22, wherein the the anti-RSV monoclonal antibody or an antigen binding fragment thereof is present in the composition at a concentration of 100 mg/mL.

Exemplary Method Embodiments—Patient's RSV Season

1. A method of treating or preventing RSV infection in a patient in need thereof, the method comprising determining whether the patient is experiencing their first or second RSV season; and administering a fixed dose of 200 milligrams (mg) of an anti-RSV monoclonal antibody or an antigen binding fragment thereof to a patient experiencing their second RSV season, wherein the anti-RSV monoclonal antibody or an antigen binding fragment thereof has an IC50 of 5.0 ng/ml or less in a neutralization assay of RSV A, or has an IC50 of 3.0 ng/ml or less in a neutralization assay of RSV B9320 or both.

2. The method of Embodiment 1, where the patient is 3 months or older.

3. The method of Embodiment 1, where the patient is 6 months or older.

4. The method of any one of Embodiments 1 to 3, wherein the patient is up to two years old.

5. A method of treating or preventing RSV infection in a patient in need thereof, the method comprising:

determining whether the patient is experiencing their first or second RSV season;

administering a fixed dose of 200 milligrams (mg) of an anti-RSV monoclonal antibody or an antigen binding fragment thereof to a patient, wherein the patient is experiencing their second RSV season;

administering a fixed dose of 100 mg of an anti-RSV monoclonal antibody or an antigen binding fragment thereof to a patient, wherein the patient is experiencing their first RSV season;

wherein the anti-RSV monoclonal antibody or an antigen binding fragment thereof has an IC50 of 5.0 ng/ml or less in a neutralization assay of RSV A, or has an IC50 of 3.0 ng/ml or less in a neutralization assay of RSV B9320, or both.

8. The method of Embodiment 7, wherein the patient is up to two years old.

9. The method of any one of the preceding Embodiments, wherein the patient has a weight of at least 5 kg.

10. The method of any one of the preceding Embodiments, wherein the patient has a gestational age of at least 29 weeks.

11. The method of any one of the preceding Embodiments, wherein the patient exhibits $AUC_{0-\infty}$ of greater than 13.4 day·mg/mL.

12. The method of any one of the preceding Embodiments, the method comprising administering the dose at the beginning of the RSV season.

13. The method of any one of the preceding Embodiments, the method comprising administering the dose intramuscularly.

14. The method of any one of the preceding Embodiments, wherein the patient exhibits Down's Syndrome, an immunodeficiency, congenital lung disease, or congenital heart disease or a combination thereof.

15. The method of any one of the preceding Embodiments, wherein the patient exhibits congenital lung disease or congenital heart disease or both.

16. The method of any one of the preceding Embodiments, the method comprising administering the anti-RSV monoclonal antibody or an antigen binding fragment thereof in a composition comprising at least one of an ionic excipient, a buffer, a sugar, and a surfactant.

17. The method of Embodiment 16, wherein the ionic excipient comprises L-arginine hydrochloride at a concentration of 80 mM.

18. The method of Embodiment 16 or Embodiment 17, wherein the buffer comprises 30 mM L-histidine/L-histidine hydrochloride, the sugar comprises 120 mM sucrose, and/or the surfactant comprises polysorbate 80 in a range of 0.01% (w/v) to 0.05% (w/v).

19. The method of any one of Embodiments 17 to 19, wherein the anti-RSV monoclonal antibody or an antigen binding fragment thereof in the composition is stable at 2° C. to 8° C. for at least 3 months as determined by high performance size exclusion chromatography (HPSEC).

20. The method of any one of Embodiments 17 to 21, wherein the composition has a pH in a range of from 5.5 to 6.5.

21. The method of any one of Embodiments 17 to 21, wherein the the anti-RSV monoclonal antibody or an antigen binding fragment thereof is present in the composition at a concentration of 100 mg/mL.

22. The method of any one of the preceding Embodiments, wherein the anti-RSV monoclonal antibody or the antigen binding fragment of the anti-RSV monoclonal antibody comprises a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to SEQ ID NO:1 and/or a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical SEQ ID NO:2.

23. The method of any one of the preceding Embodiments, wherein the anti-RSV monoclonal antibody or the antigen binding fragment of the anti-RSV monoclonal antibody comprises a sequence comprising SEQ ID NO:1 and/or SEQ ID NO:2.

24. The method of any one of the preceding Embodiments, wherein the anti-RSV monoclonal antibody or the antigen binding fragment of the anti-RSV monoclonal antibody comprises:

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence QASQDIVNYLN (SEQ ID NO:3);

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence VASNLET (SEQ ID NO:4);

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence QQYDNLPLT (SEQ ID NO:5);

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence DYIIN (SEQ ID NO:6);

a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence GIIPVLGTVHYGPKFQG (SEQ ID NO:7); and/or a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence ETALVVSETYLPHYFDN (SEQ ID NO:8).

25. The method of any one of the preceding Embodiments, wherein the anti-RSV monoclonal antibody or the antigen binding fragment of the anti-RSV monoclonal antibody comprises QASQDIVNYLN (SEQ ID NO:3), VASNLET (SEQ ID NO:4), QQYDNLPLT (SEQ ID NO:5), DYIIN (SEQ ID NO:6), GIIPVLGTVHYGPKFQG (SEQ ID NO:7), and/or ETALVVSETYLPHYFDN (SEQ ID NO:8).

26. The method of any one of the preceding Embodiments, wherein the anti-RSV monoclonal antibody or the antigen binding fragment of the anti-RSV monoclonal antibody comprises QASQDIVNYLN (SEQ ID NO:3), VASNLET (SEQ ID NO:4), QQYDNLPLT (SEQ ID NO:5), DYIIN (SEQ ID NO:6), GIIPVLGTVHYGPKFQG (SEQ ID NO:7), and ETALVVSETYLPHYFDN (SEQ ID NO:8).

27. The method of any one of the preceding Embodiments, wherein the anti-RSV monoclonal antibody comprises a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence of SEQ ID NO:9 and/or a sequence which is at least 70%, at least 75%, at least 80%, at least 85%, at least 90%, at least 91%, at least 92%, at least 93%, at least 94%, at least 95%, at least 96%, at least 97%, at least 98%, or at least 99% identical to the sequence of SEQ ID NO:10.

28. The method of any one of the preceding Embodiments, wherein the anti-RSV monoclonal antibody comprises nirsevimab or wherein the antigen binding fragment of the anti-RSV monoclonal antibody comprises an antigen binding fragment of nirsevimab.

Exemplary Pharmaceutical Unit Dose Embodiments

1. A pharmaceutical unit dose comprising 100 mg of nirsevimab, wherein said unit dose is suitable for intramuscular administration.

2. A pharmaceutical unit dose comprising 200 mg of nirsevimab, wherein said unit dose is suitable for intramuscular administration.

3. The pharmaceutical unit dose of any one of the preceding Embodiments, wherein the pharmaceutical unit dose comprising a composition comprising nirsevimab, the composition further comprising at least one of an ionic excipient, a buffer, a sugar, and a surfactant.

4. The pharmaceutical unit dose of Embodiment 3, wherein the ionic excipient comprises L-arginine hydrochloride at a concentration of 80 mM.

5. The pharmaceutical unit dose of Embodiment 3 or Embodiment 4, wherein the buffer comprises 30 mM L-histidine/L-histidine hydrochloride, the sugar comprises 120 mM sucrose, and the surfactant comprises polysorbate-80 in a range of 0.01% (w/v) to 0.05% (w/v).

6. The pharmaceutical unit dose of any one of Embodiments 3 to 5, wherein the nirsevimab in the composition is stable at 2° C. to 8° C. for at least 3 months as determined by high performance size exclusion chromatography (HPSEC).

7. The pharmaceutical unit dose of any one of Embodiments 3 to 6, wherein the composition has a pH in a range of from 5.5 to 6.5

8. The pharmaceutical unit dose of any one of the preceding Embodiments, wherein the nirsevimab is present at a concentration of 100 mg/mL.

Exemplary Pharmaceutical Composition Embodiments

1. A pharmaceutical composition for the treatment or prevention of RSV infection, the composition comprising 100 mg of nirsevimab, wherein the composition is administered to a patient in the first year of life, the patient having a weight of at least 5 kg.

2. The pharmaceutical composition of Embodiment 1, wherein the composition is administered when the patient is entering their first RSV season.

3. A pharmaceutical composition for the treatment or prevention of RSV infection, the composition comprising 100 mg of nirsevimab, wherein the composition is administered to a patient entering their first RSV season.

4. A pharmaceutical composition for the treatment or prevention of RSV infection, the composition comprising 200 mg of nirsevimab, wherein the composition is administered to a patient in the second year of life.

5. The pharmaceutical composition of Embodiment 3, wherein the patient is entering their second RSV season.

6. A pharmaceutical composition for the treatment or prevention of RSV infection, the composition comprising 200 mg of nirsevimab, wherein the composition is administered to a patient entering their second RSV season.

7. The pharmaceutical composition of any one of the preceding Embodiments, wherein the patient exhibits congenital lung disease or congenital heart disease or both.

8. The pharmaceutical composition of any one of the preceding Embodiments, wherein the patient exhibits $AUG_{0-\infty}$ of greater than 13.4 day·mg/mL.

9. The pharmaceutical composition of any one of the preceding Embodiments, the pharmaceutical composition having a pH in a range of from 5.5 to 6.5.

10. The pharmaceutical composition of any one of the preceding Embodiments, the pharmaceutical composition further comprising at least one of an ionic excipient, a buffer, a sugar, and a surfactant.

11. The pharmaceutical composition of Embodiment 10, the pharmaceutical composition comprising L-arginine hydrochloride at a concentration of 80 mM.

12. The pharmaceutical composition of any Embodiment 10 or 11, wherein the buffer comprises 30 mM L-histidine/L-histidine hydrochloride, the sugar comprises 120 mM sucrose, and the surfactant comprises polysorbate-80 in a range of 0.01% (w/v) to 0.05% (w/v).

13. The pharmaceutical composition of any one of the preceding Embodiments, wherein the nirsevimab in the pharmaceutical composition is stable at 2° C. to 8° C. for at least 3 months as determined by high performance size exclusion chromatography (HPSEC).

14. The pharmaceutical unit dose of any one of the preceding Embodiments, wherein the nirsevimab is present at a concentration of 100 mg/mL.

The present invention is illustrated by the following examples. It is to be understood that the particular examples, materials, amounts, and procedures are to be interpreted broadly in accordance with the scope and spirit of the invention as set forth herein.

EXAMPLES

Example 1—Phase 2b Study

This Example describes a Phase 2b study of nirsevimab. The primary objective of the study was to compare the efficacy of nirsevimab versus placebo for a reduction of medically attended RSV-confirmed lower respiratory tract infections (LRTI) during the first 150 days post dose (that is, Day 151; the duration of a typical 5-month RSV season). The secondary efficacy objective included a comparison of nirsevimab versus placebo for a reduction of hospitalisations due to confirmed RSV through Day 151. Other objectives included a comparison of the safety and tolerability of nirsevimab versus placebo and an evaluation of the pharmacokinetic (PK) and anti-drug antibody (ADA) response to nirsevimab.

The target serum concentration of 6.8 μg/mL for the Phase 2b Study was based on RSV challenge studies in cotton rats, a model that has been proven to be a reliable predictor of target concentrations and was used for dose selection of palivizumab (Synagis Summary of Product Characteristics, 2018). Selection of the 50-mg IM dose for the Phase 2b study was based on the population-PK model used to identify a dose that would maintain nirsevimab serum concentrations above 6.8 μg/mL throughout the RSV season. Nirsevimab met this exposure target (achieved in >95% subjects) and the primary endpoint in this study by achieving a statistically significant relative risk reduction (RRR) of medically attended RSV-confirmed LRTI when compared to placebo whilst demonstrating safety.

The Phase 2b Study was a randomised, double-blind, placebo-controlled study that evaluated the safety, efficacy, PK, and immunogenicity of nirsevimab in healthy preterm infants, born between 29 weeks 0 days and 34 weeks 6 days gestational age, entering their first RSV season (see FIG. 3). Subjects were not eligible for RSV prophylaxis with palivizumab based on the Joint Committee on Vaccination and Immunisation, American Academy of Pediatrics, or other local or national guidelines, allowing for a placebo comparator group. Subjects were randomised at a 2:1 ratio to receive a single IM dose of 50 mg nirsevimab or placebo. Randomisation was stratified by hemisphere (northern, southern) and by subject age at the time of randomisation (<3 months, >3 to <6 months, >6 months). Subjects were followed for 360 days after dosing.

Subjects were monitored throughout the study for LRTI. All subjects seeking medical attention for a respiratory illness (in an inpatient or outpatient setting) were evaluated for the occurrence of LRTI. Subjects who had a primary hospitalisation for a respiratory illness, a respiratory deterioration during a hospitalisation, or who sought outpatient medical attention, including emergency room visits for a respiratory illness, were assessed for RSV by diagnostic testing of respiratory secretions and clinical assessment for the presence of LRTI. Testing for RSV was performed centrally using the US FDA-approved and Conformité Européenne-marked in vitro diagnostic real-time RT-PCR assay (Lyra RSV+hMPV assay, Quidel Corporation, San Diego, CA; www.quidel.com). A diagnosis of RSV LRTI required having a respiratory sample positive for RSV by the central RT-PCR assay.

Subject Population

Disposition.

As of the data cutoff (DCO) date for the primary analysis, all subjects were enrolled and a complete dataset for all randomised subjects was available through Day 151. Overall, 1,453 subjects (969 subjects, nirsevimab; 484 subjects, placebo) were randomised, with 1,447 subjects receiving a single dose of nirsevimab (968 subjects) or placebo (479 subjects; Table 1). Two subjects randomised to the placebo group incorrectly received nirsevimab; both subjects were included in the As-treated Population under the nirsevimab group.

The majority of subjects completed the Day 151 efficacy follow-up (948 subjects [97.8%], nirsevimab; 474 subjects [97.9%], placebo). As of the DCO date, 676 subjects (46.5%) completed the study and 710 (48.9%) were ongoing. The median number of days on study was 252 (range, 229 to 289 days).

Demographics.

Demographic and baseline characteristics were comparable between the nirsevimab and placebo groups (Table 2). Overall, 52% of subjects were male, 72% were White, and 35% had siblings enrolled in the study.

Efficacy

Primary Endpoint—Incidence of Medically Attended RSV-Confirmed LRTI

Based on the primary analysis in the Intent-to-treat (ITT) Population, a single dose of 50 mg IM nirsevimab resulted in a relative risk reduction (RRR) in the incidence of medically attended RSV-confirmed LRTI through Day 151 of 70.2% (95% CI: 52.4%, 81.3%) when compared to placebo ($p<0.0001$; Table 3). Similar results were seen based on the same primary analysis model in the Per-protocol Population and the supporting Cochran-Mantel-Haenszel test in the ITT Population (Table 3).

Figure 4:
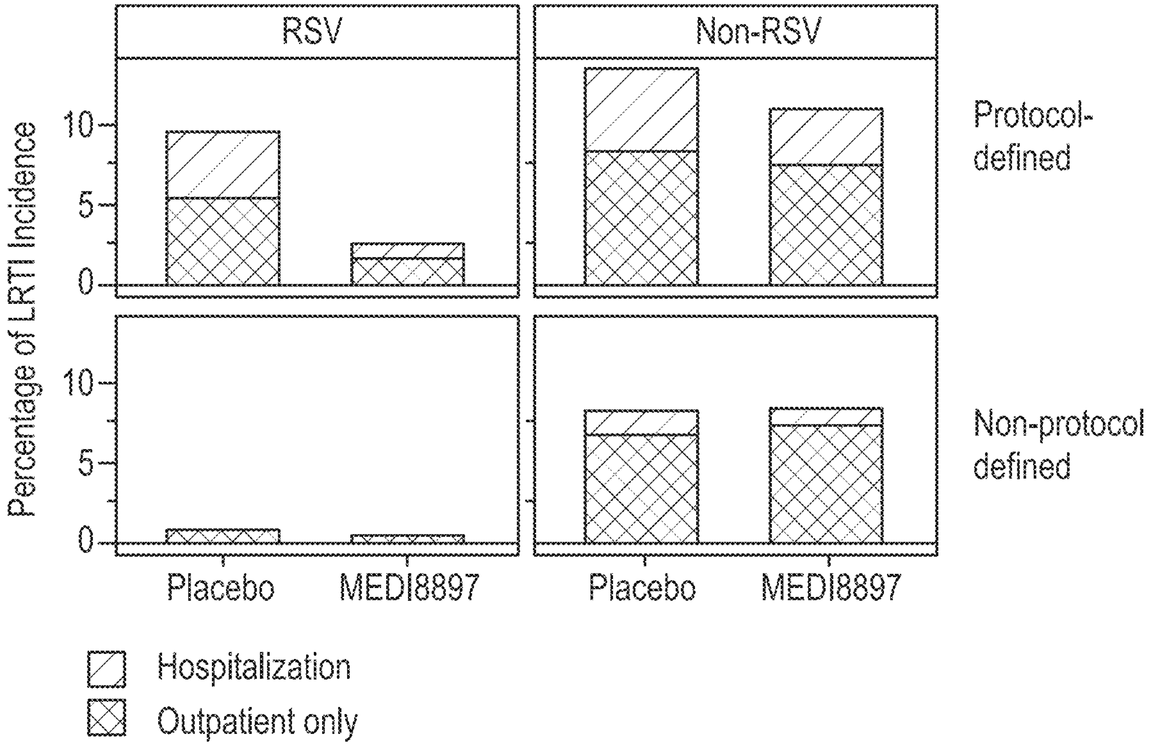
FIG. 4 shows incidence of all medically attended lower respiratory tract infections through 150 days post dose, as further described in Example 1. LRTI=lower respiratory tract infection; RSV=respiratory syncytial virus.

The incidence of all medically attended LRTI (protocol and non-protocol defined) through Day 151 was 19.7% in the nirsevimab group and 25.8% in the placebo group. As shown in Table 3, protocol-defined RSV-confirmed LRTI was seen in 2.6% of subjects in the nirsevimab group and 9.5% of subjects in the placebo group. The incidence of non-RSV LRTI (protocol or non-protocol defined) was generally similar between the groups (FIG. 4), suggesting that infection due to other viruses was not increased in the nirsevimab group.

Figure 5:
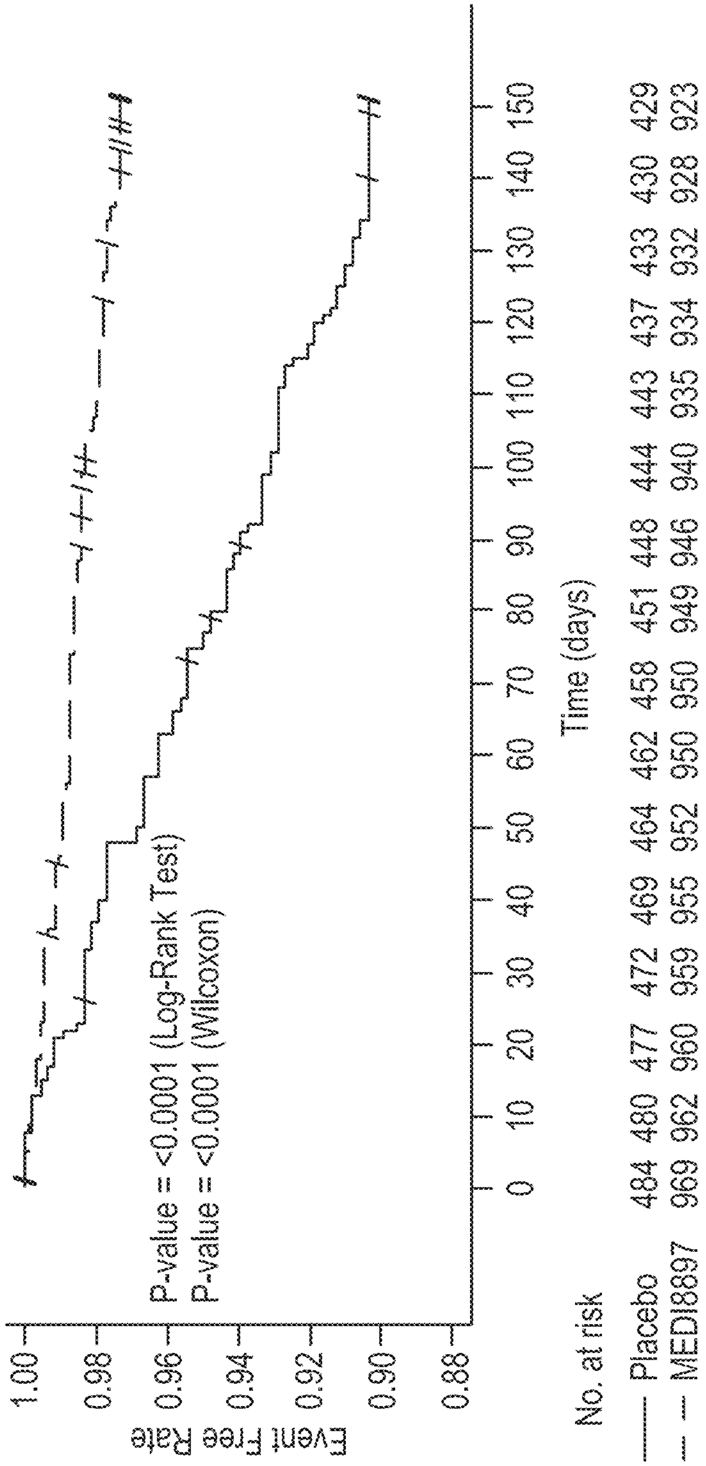
FIG. 5 shows a Kaplan-Meier plot for time to first medically attended RSV-confirmed LRTI through 150 days post dose, as further described in Example 1. LRTI=lower respiratory tract infection; No=number; RSV=respiratory syncytial virus. P-values were obtained from stratified log-rank test and Wilcoxon test with 2 stratification factors (age at randomisation and hemisphere) as the strata.

Efficacy of nirsevimab through Day 151 was confirmed with Kaplan-Meier analysis (p<0.0001; FIG. 5).

Subgroup Analysis.

Figure 6B:
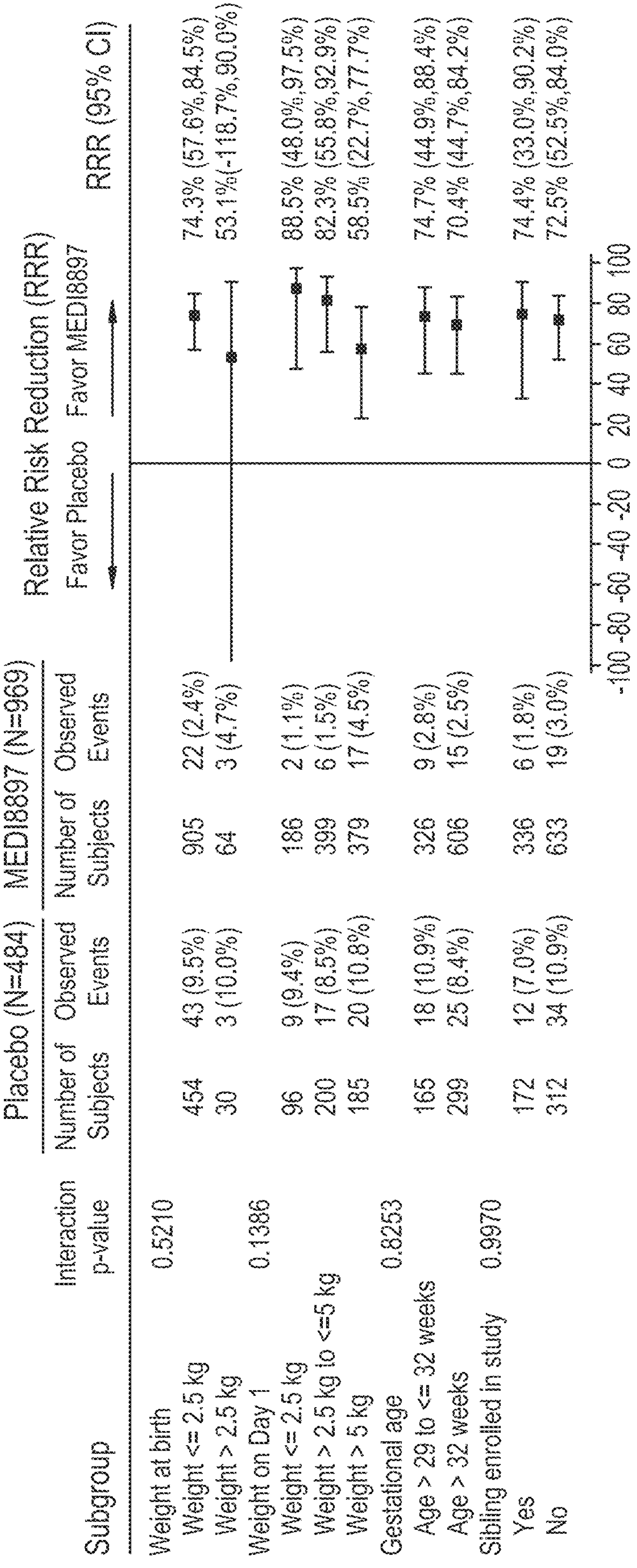

Subgroup analyses showed consistent results for hemisphere, age at randomisation, weight at birth, weight at Day 1, gestational age (GA), and siblings enrolled in the study, with no statistically significant interactions between each subgroup and treatment and relative risk reduction through Day 151 favouring nirsevimab vs placebo across all subgroups (FIG. 6). While efficacy was demonstrated for infants >5 kg, it was less than that seen for the smaller weight infants. Additional PK exposure-efficacy analyses showed that a dose of 100 mg would give similar exposures for infants ≥5 kg with a predicted improvement in efficacy.

TABLE 1

Subject Disposition, Primary Analysis

| Parameter | Placebo | Nirsevimab | Total |
|---|---|---|---|
| Subjects randomised | 484 | 969 | 1453 |
| Northern hemisphere | 329 (68.0%) | 659 (68.0%) | 988 (68.0%) |
| Southern hemisphere | 155 (32.0%) | 310 (32.0%) | 465 (32.0%) |
| Subjects treated [a] | 481 (99.4%) | 966 (99.7%) | 1447 (99.6%) |
| Completed Day 151 efficacy follow-up | 474 (97.9%) | 948 (97.8%) | 1422 (97.9%) |
| Completed the study | 221 (45.7%) | 455 (47.0%) | 676 (46.5%) |
| Early discontinuation | 27 (5.6%) | 40 (4.1%) | 67 (4.6%) |
| Death | 4 (0.8%)[b] | 2 (0.2%) | 6 (0.4%) |
| Lost to follow-up | 9 (1.9%) | 17 (1.8%) | 26 (1.8%) |
| Withdrawal by parent/legal representative | 12 (2.5%) | 19 (2.0%) | 31 (2.1%) |
| Other | 2 (0.4%) | 2 (0.2%) | 4 (0.3%) |
| Subjects who are ongoing | 236 (48.8%) | 474 (48.9%) | 710 (48.9%) |
| Days on study as of DCO, median (min, max) | 252.0 (229, 289) | 251.5 (229, 289) | 252.0 (229, 289) |

DCO = data cutoff; max = maximum; min = minimum.

Denominator in the percentage calculation is based on the number of randomised subjects.

[a] Two subjects randomised to the placebo group incorrectly received nirsevimab. Both subjects are included in the As-treated Population under the nirsevimab group.

[b] One of the 4 deaths in the placebo group occurred after Day 361.

TABLE 2

Demographics and Baseline Characteristics - Intent-to-treat Population

| Characteristic | Placebo (N = 484) | Nirsevimab (N = 969) | Total (N = 1453) |
|---|---|---|---|
| Age (months) at randomisation, mean (SD) | 3.28 (2.31) | 3.29 (2.22) | 3.29 (2.25) |
| Weight (kg) on Day 1, mean (SD) | 4.51 (1.96) | 4.60 (1.92) | 4.57 (1.93) |
| Gender: Male | 260 (53.7%) | 501 (51.7%) | 761 (52.4%) |
| Race | | | |
| White | 355 (73.3%) | 693 (71.6%) | 1048 (72.2%) |
| Black or African American | 67 (13.8%) | 189 (19.5%) | 256 (17.6%) |
| Asian | 10 (2.1%) | 5 (0.5%) | 15 (1.0%) |
| American Indian or Alaskan Native | 1 (0.2%) | 0 | 1 (0.1%) |
| Native Hawaiian or Other Pacific Islander | 3 (0.6%) | 8 (0.8%) | 11 (0.8%) |
| Other | 43 (8.9%) | 61 (6.3%) | 104 (7.2%) |
| Multiple categories checked | 5 (1.0%) | 12 (1.2%) | 17 (1.2%) |
| Gestational age (weeks), mean (SD) | 32.7 (1.5) | 32.7 (1.4) | 32.7 (1.4) |
| Gestational age >29 to <32 weeks | 165 (35.6%) | 326 (35.0%) | 491 (35.2%) |
| Gestational age >32 weeks | 299 (64.4%) | 606 (65.0%) | 905 (64.8%) |
| Siblings enrolled in the study | 172 (35.5%) | 336 (34.7%) | 508 (35.0%) |

SD = standard deviation.

TABLE 3

Incidence of Medically Attended RSV-confirmed LRTI Through 150 Days Post Dose

| Analysis | Placebo (N = 484) | Nirsevimab (N = 969) | Relative Risk Reduction (95% CI) | P value |
|---|---|---|---|---|
| Poisson regression with robust variance | | | | |
| Observed events | 46 (9.5%) | 25 (2.6%) | NA | |
| Subjects requiring imputation [a] | 9 (1.9%) | 21 (2.2%) | NA | |
| Efficacy | | | 70.2% (52.4%, 81.3%) | <0.0001 |

TABLE 3-continued

Incidence of Medically Attended RSV-confirmed LRTI Through 150 Days Post Dose

| Analysis | Placebo (N = 484) | Nirsevimab (N = 969) | Relative Risk Reduction (95% CI) | P value |
|---|---|---|---|---|
| Stratified Cochran-Mantel-Haenszel test | | | | |
| Observed events | 46 (9.5%) | 25 (2.6%) | NA | |
| Efficacy | | | 72.9% (56.5%, 83.1%) | <0.0001 |

CI = confidence interval; LRTI = lower respiratory tract infection; NA = not applicable; RSV = respiratory syncytial virus.
[c] Subjects who had no events and were not followed through 150 days post dose.

Secondary Endpoint—Incidence of RSV LRTI Hospitalisation

Based on the primary analysis model in the Intent-to-treat (ITT) Population, a single dose of 50 mg IM nirsevimab resulted in a relative risk reduction (RRR) in the incidence of RSV LRTI hospitalisation through Day 151 of 78.8% (95% CI: 52.3%, 90.6%) when compared to placebo (p=0.0002; Table 4). Similar results were seen based on the same primary analysis model in the Per-protocol Population and the supporting Cochran-Mantel-Haenszel test in the ITT Population (Table 4).

Efficacy by RSV Subtype

Nirsevimab demonstrated activity against RSV A and RSV B subtypes (Table 5). RSV A and RSV B subtypes were responsible for a similar proportion of RSV LRTI overall and hospitalisation through Day 151. The incidence due to either subtype was notably lower in the nirsevimab group vs the placebo group.

TABLE 4

Incidence of RSV LRTI Hospitalisation Through 150 Days Post Dose

| Analysis | Placebo (N = 484) | Nirsevimab (N = 969) | Relative Risk Reduction (95% CI) | P value |
|---|---|---|---|---|
| Poisson regression with robust variance | | | | |
| Observed events | 20 (4.1%) | 8 (0.8%) | NA | |
| Subjects requiring imputation[a] | 9 (1.9%) | 21 (2.2%) | NA | |
| Efficacy | | | 78.8% (52.3%, 90.6%) | 0.0002 |
| Stratified Cochran-Mantel-Haenszel test | | | | |
| Observed events | 20 (4.1%) | 8 (0.8%) | NA | |
| Efficacy | | | 80.0% (55.0%, 91.1%) | <0.0001 |

CI = confidence interval; LRTI = lower respiratory tract infection; RSV = respiratory syncytial virus.
[a] Subjects who had no events and were not followed through 150 days post dose.

TABLE 5

Summary of Efficacy by RSV Subtype Through 150 Days Post Dose

| Endpoint | Placebo (N = 484) | Nirsevimab (N = 969) |
|---|---|---|
| Incidence of medically attended RSV-confirmed LRTI | 46 (9.5%) | 25 (2.6%) |
| RSV A | 24 (5.0%) | 11 (1.1%) |
| RSV B | 22 (4.5%) | 14 (1.4%) |
| Incidence of RSV LRTI hospitalisation | 20 (4.1%) | 8 (0.8%) |
| RSV A | 12 (2.5%) | 5 (0.5%) |
| RSV B | 8 (1.7%) | 3 (0.3%) |

LRTI = lower respiratory tract infection; RSV = respiratory syncytial virus.

Safety

Summary of Adverse Events

In the As-treated Population, treatment-emergent adverse event (TEAE) rates for the nirsevimab group were generally comparable or lower than the placebo group across the TEAE categories (Table 6). Overall, 83.7% of subjects in the nirsevimab group and 83.9% of subjects in the placebo group had at least 1 TEAE. TEAEs ≤1 day post dose occurred in 2.5% of subjects in both groups. In comparison to the placebo group, the nirsevimab group had a lower incidence of TEAEs occurring ≤7 days post dose (15.2% vs 12.5%, respectively), TEAEs ≥Grade 3 in severity (12.3% vs 7.4%, respectively), or TESAEs (16.7% vs 10.4%, respectively).

Five deaths were reported during the study through Day 361 as of the DCO for the primary analysis, including 2 subjects (0.2%) in the nirsevimab group and 3 subjects (0.6%) in the placebo group. One additional subject in the placebo group died on Day 367. None of these deaths were related to study treatment according to the investigator.

Overall, the incidence of treatment-related AEs (nirsevimab 2.3%, placebo 2.1%); adverse events of special interest (AESIs), including hypersensitivity, immune complex disease, and thrombocytopenia (nirsevimab 0.5%, placebo 0.6%); and NOCDs (nirsevimab 0.3%, placebo 0.8%) was low and generally comparable between the placebo and nirsevimab groups. TEAEs that involved the skin and subcutaneous tissues (including diaper rash) were collected as skin reactions, with a few exceptions for skin reactions that could be definitively diagnosed such as impetigo, varicella, and scabies. Skin reactions were reported in a similar percentage of subjects in both treatment groups (nirsevimab 28.2%, placebo 26.5%).

Adverse Events

The TEAE profile was generally comparable between the nirsevimab and placebo groups (Table 7). Upper respiratory tract infection (URTI) was the most common TEAE in both groups (38.5% nirsevimab, 32.6% placebo). Similarly, within each age group (≤3 months, >3 to ≤6 months, or >6 months), the percentage of subjects with TEAEs overall or ≤1 day or ≤7 days post dose was comparable between the nirsevimab and placebo groups (Table 6, Table 8).

The percentage of subjects with treatment-related TEAEs according to the investigator was generally similar between the nirsevimab and placebo groups overall and across the 3 age groups (Table 6, Table 8). None of the treatment-related events were reported in more than 2 subjects.

Serious Adverse Events

Generally, there was a trend for lower treatment-emergent serious adverse event (TESAE) rates in the nirsevimab group vs the placebo group (overall: 10.4% nirsevimab, 16.7% placebo; (Table 9). The most common TESAEs, based on the nirsevimab group, were bronchiolitis (2.1% nirsevimab, 4.2% placebo), lower respiratory tract infection (1.4% nirsevimab, 2.7% placebo), pneumonia (1.4% nirsevimab, 2.1% placebo), and bronchitis (1.2% nirsevimab, 2.3% placebo). None of the TESAEs were considered related to study treatment by the investigator (Table 6).

Adverse Events of Special Interest

AESIs were reported in 5 subjects (0.5%) in the nirsevimab and 3 subjects (0.6%) in the placebo group (Table 10). All events were Grade 1 in severity. The TEAE of petechiae that was reported as an AESI was 1-day duration and was reported by the site investigator based on parental description. There were no laboratory assessments for the petechiae.

TABLE 6

Summary of Treatment-emergent Adverse Events

| Subjects[a] with | Placebo (N = 479) | Nirsevimab (N = 968) | Total (N = 1447) |
|---|---|---|---|
| At least 1 event | 402 (83.9%) | 810 (83.7%) | 1212 (83.8%) |
| At least 1 event occurring ≤1 day post dose | 12 (2.5%) | 24 (2.5%) | 36 (2.5%) |
| At least 1 event occurring ≤7 days post dose | 73 (15.2%) | 121 (12.5%) | 194 (13.4%) |
| At least 1 investigational product-related event | 10 (2.1%) | 22 (2.3%) | 32 (2.2%) |
| At least 1 event of > Grade 3 severity | 59 (12.3%) | 72 (7.4%) | 131 (9.1%) |
| Death (Grade 5 severity) | 3 (0.6%)[b] | 2 (0.2%) | 5 (0.3%) |
| At least 1 serious event | 80 (16.7%) | 101 (10.4%) | 181 (12.5%) |
| At least 1 serious and/or >Grade 3 severity event | 92 (19.2%) | 114 (11.8%) | 206 (14.2%) |
| At least 1 investigational product-related serious event | 0 | 0 | 0 |
| At least 1 AESI | 3 (0.6%) | 5 (0.5%) | 8 (0.6%) |
| At least 1 investigational product-related AESI | 3 (0.6%) | 5 (0.5%) | 8 (0.6%) |
| At least 1 skin reaction | 127 (26.5%) | 273 (28.2%) | 400 (27.6%) |
| At least 1 investigational product-related skin reaction | 4 (0.8%) | 9 (0.9%) | 13 (0.9%) |
| At least 1 skin hypersensitivity reaction | 3 (0.6%) | 5 (0.5%) | 8 (0.6%) |
| At least 1 investigational product-related skin hypersensitivity reaction | 3 (0.6%) | 5 (0.5%) | 8 (0.6%) |
| At least 1 NOCD | 4 (0.8%) | 3 (0.3%) | 7 (0.5%) |
| At least 1 investigational product-related NOCD | 0 | 0 | 0 |

AESI = adverse event of special interest; NOCD = new onset chronic disease.
[a]Subjects were counted once for each category regardless of the number of events.
[b]One additional death occurred in the placebo group after Day 361.

TABLE 7

Ten Most Common Treatment-emergent Adverse Events Occurring in the Nirsevimab Group by Preferred Term

| Preferred Term (MedDRA version 21.0) | Placebo (N = 479) | Nirsevimab (N = 968) | Total (N = 1447) |
|---|---|---|---|
| Subjects with at least 1 event | 402 (83.9%) | 810 (83.7%) | 1212 (83.8%) |
| Upper respiratory tract infection | 156 (32.6%) | 373 (38.5%) | 529 (36.6%) |
| Nasopharyngitis | 83 (17.3%) | 140 (14.5%) | 223 (15.4%) |
| Gastroenteritis | 41 (8.6%) | 105 (10.8%) | 146 (10.1%) |
| Rhinitis | 43 (9.0%) | 102 (10.5%) | 145 (10.0%) |
| Pyrexia | 53 (11.1%) | 94 (9.7%) | 147 (10.2%) |
| Bronchitis | 55 (11.5%) | 93 (9.6%) | 148 (10.2%) |
| Bronchiolitis | 51 (10.6%) | 89 (9.2%) | 140 (9.7%) |
| Diarrhoea | 45 (9.4%) | 88 (9.1%) | 133 (9.2%) |

TABLE 7-continued

Ten Most Common Treatment-emergent Adverse Events Occurring in the Nirsevimab Group by Preferred Term

| Preferred Term (MedDRA version 21.0) | Placebo (N = 479) | Nirsevimab (N = 968) | Total (N = 1447) |
|---|---|---|---|
| Lower respiratory tract infection | 50 (10.4%) | 82 (8.5%) | 132 (9.1%) |
| Conjunctivitis | 36 (7.5%) | 75 (7.7%) | 111 (7.7%) |

MedDRA = Medical Dictionary for Regulatory Activities.

TABLE 8

Treatment-emergent Adverse Events by Age and Time Post Dose

| Parameter | Placebo (N = 479) | Nirsevimab (N = 968) | Total (N = 1447) |
|---|---|---|---|
| Subjects with at least 1 event | 402 (83.9%) | 810 (83.7%) | 1212 (83.8%) |
| Age ≤3 months | 211/255 (82.7%) | 423/517 (81.8%) | 634/772 (82.1%) |
| Age >3 to ≤6 months | 126/150 (84.0%) | 272/320 (85.0%) | 398/470 (84.7%) |
| Age >6 months | 65/74 (87.8%) | 115/131 (87.8%) | 180/205 (87.8%) |
| Subjects with at least 1 event occurring ≤1 day post dose | 12 (2.5%) | 24 (2.5%) | 36 (2.5%) |
| Age ≤3 months | 2/255 (0.8%) | 10/517 (1.9%) | 12/772 (1.6%) |
| Age >3 to ≤6 months | 7/150 (4.7%) | 10/320 (3.1%) | 17/470 (3.6%) |
| Age >6 months | 3/74 (4.1%) | 4/131 (3.1%) | 7/205 (3.4%) |
| Subjects with at least 1 event occurring ≤7 days post dose | 73 (15.2%) | 121 (12.5%) | 194 (13.4%) |
| Age ≤3 months | 36/255 (14.1%) | 58/517 (11.2%) | 94/772 (12.2%) |
| Age >3 to ≤6 months | 21/150 (14.0%) | 42/320 (13.1%) | 63/470 (13.4%) |
| Age >6 months | 16/74 (21.6%) | 21/131 (16.0%) | 37/205 (18.0%) |

TABLE 9

Ten Most Common Treatment-emergent Serious Adverse Events Occurring in the Nirsevimab Group by Preferred Term

| Preferred Term (MedDRA version 21.0) | Placebo (N = 479) | Nirsevimab (N = 968) | Total (N = 1447) |
|---|---|---|---|
| Subjects with at least 1 serious event | 80 (16.7%) | 101 (10.4%) | 181 (12.5%) |
| Bronchiolitis | 20 (4.2%) | 20 (2.1%) | 40 (2.8%) |
| Lower respiratory tract infection | 13 (2.7%) | 14 (1.4%) | 27 (1.9%) |
| Pneumonia | 10 (2.1%) | 14 (1.4%) | 24 (1.7%) |
| Bronchitis | 11 (2.3%) | 12 (1.2%) | 23 (1.6%) |
| Gastroenteritis | 4 (0.8%) | 8 (0.8%) | 12 (0.8%) |
| Pneumonia viral | 2 (0.4%) | 7 (0.7%) | 9 (0.6%) |

TABLE 9-continued

Ten Most Common Treatment-emergent Serious Adverse Events Occurring in the Nirsevimab Group by Preferred Term

| Preferred Term (MedDRA version 21.0) | Placebo (N = 479) | Nirsevimab (N = 968) | Total (N = 1447) |
|---|---|---|---|
| Lower respiratory tract infection viral | 3 (0.6%) | 5 (0.5%) | 8 (0.6%) |
| Pyrexia | 1 (0.2%) | 3 (0.3%) | 4 (0.3%) |
| Upper respiratory tract infection | 3 (0.6%) | 3 (0.3%) | 6 (0.4%) |
| Croup infectious | 0 | 2 (0.2%) | 2 (0.1%) |

MedDRA = Medical Dictionary for Regulatory Activities.

TABLE 10

Adverse Events of Special Interest by Age and Preferred Term

| Age Preferred Term (MedDRA version 21.0) | Placebo (N = 479) | Nirsevimab (N = 968) | Total (N = 1447) |
|---|---|---|---|
| Subjects with at least 1 AESI | 3 (0.6%) | 5 (0.5%) | 8 (0.6%) |
| Age ≤3 months | | | |
| Subjects with at least 1 event | 0/255 | 3/517 (0.6%) | 3/772 (0.4%) |
| Rash | 0/255 | 2/517 (0.4%) | 2/772 (0.3%) |
| Petechiae | 0/255 | 1/517 (0.2%) | 1/772 (0.1%) |
| Age >3 to ≤6 months | | | |
| Subjects with at least 1 event | 3/150 (2.0%) | 1/320 (0.3%) | 4/470 (0.9%) |
| Rash | 2/150 (1.3%) | 1/320 (0.3%) | 3/470 (0.6%) |
| Rash papular | 1/150 (0.7%) | 0/320 | 1/470 (0.2%) |

TABLE 10-continued

| Adverse Events of Special Interest by Age and Preferred Term | | | |
|---|---|---|---|
| Age Preferred Term (MedDRA version 21.0) | Placebo (N = 479) | Nirsevimab (N = 968) | Total (N = 1447) |
| Age >6 months | | | |
| Subjects with at least 1 event | 0/74 | 1/131 (0.8%) | 1/205 (0.5%) |
| Rash macular | 0/74 | 1/131 (0.8%) | 1/205 (0.5%) |

AESI = adverse event of special interest; MedDRA = Medical Dictionary for Regulatory Activities.

Pharmacokinetics

Following a single fixed 50 mg IM dose of nirsevimab, over 95% of measurable Day 151 nirsevimab serum concentrations were greater than the nonclinical EC90 target of 6.8 μg/mL (Table 11).

Although the scheduled PK sampling scheme was sparse, $AUG_{0-\infty}$ and apparent t½ could be estimated by non-compartmental analysis for 26 infants with sufficient additional PK samples from unscheduled visits. Overall, the median $AUG_{0-\infty}$ and estimated apparent t½ were 5.3 day·mg/mL (range, 3.2 to 10.2 day·mg/mL) and 56.5 days (range, 46.8 to 81.1 days), respectively.

TABLE 11

Summary of Observed Nirsevimab Serum Concentrations by Scheduled PK Sampling Timepoint - As-treated Population, Nirsevimab Subjects with Available Serum Samples (Study D5290C00003)

| Parameter (μg/mL) | Day 91 (N = 881) | Day 151 (N = 848) | Day 361 (N = 372) |
|---|---|---|---|
| Mean (SD) | 36.0 (10.9) | 18.9 (7.36) | 1.91 (1.08) |
| Geomean (% CV) | 34.2 (30.3) | 17.5 (38.9) | 1.64 (56.3) |
| Range | 4.18, 71.9 | 2.24, 61.54 | 0.51, 6.21 |

CV = coefficient of variation; PK = pharmacokinetic; SD = standard deviation.
Includes data only from subjects in the nirsevimab group who had at least one measurable post-dose nirsevimab serum sample.

Anti-Drug Antibody

Overall, the rate and titres of anti-drug antibodies (ADA) were low, and in ADA-positive subjects there was no effect on PK or safety. Of the subjects who had serum samples available for testing, ADA was detected post baseline in 4.3% (40/921) of subjects in the nirsevimab group and 2.8% (13/466) of subjects in the placebo group: on Day 91 (nirsevimab 1.2%, placebo 0.9%), Day 151 (nirsevimab 2.0%, placebo 1.4%), and Day 361 (nirsevimab 3.5%, placebo 1.5%). ADA titres ranged from 1:50 to 1:3,200 in the nirsevimab group and 1:50 to 1:200 in the placebo group.

Of the nirsevimab subjects who were post-baseline ADA positive, ADA targeting the YTE domain was observed in 4/17 subjects (23.5%) on Day 151 and 10/15 subjects (66.7%) on Day 361. Two nirsevimab subjects had NAb on Day 361. Of the placebo subjects who were post-baseline ADA positive, ADA targeting the YTE domain was observed in 3/3 subjects on Day 361; 1 subject had NAb on Day 361.

Nirsevimab Resistance

All 103 RSV-positive serum samples (from 40 nirsevimab-dosed subjects and 63 placebo-dosed subjects; determined by the Lyra RSV+hMPV real-time RT-PCR assay) were subjected to Sanger sequencing of the F gene and resulted in complete full-length F gene sequence for analysis with 53 RSV A and 50 RSV B sequences. Of these samples, 84 (from 29 nirsevimab-dosed subjects and 55 placebo-dosed subjects) represented unique incidences of LRTI (protocol and non-protocol defined) that occurred within the first season (through Day 151). The remaining 19 sequences were isolated from samples that were collected in error from subjects with URTI (4 nirsevimab dosed, 3 placebo dosed), LRTI outside the 150-day window (6 nirsevimab dosed, 2 placebo dosed), or from multiple sample collections from the same subject during a single clinical incidence that resulted in identical sequences (1 nirsevimab dosed, 3 placebo dosed). All F gene sequences were aligned and compared to a consensus sequence to identify potential amino acid variations within the nirsevimab binding site (Table 12). Amino acid variation K209R in RSV A and I206M+Q209R in RSV B in the nirsevimab binding site have been seen in previous studies in subjects not dosed with study drug and have shown no change in nirsevimab susceptibility (Zhu et al, 2018 J Infect Dis. 218(4):572-580). Of the two other viruses identified with variations in the nirsevimab binding site compared to consensus, one encoded a N208S change in F sequence, and another isolate encoded changes at I64I/T+K68K/E+I206M+Q209R. The N208S change has previously been identified in the preclinical work, and this mutation in the context of RSV B9320 results in a substantial susceptibility shift to nirsevimab. The I64T+K68E+I206M+Q209R combination has previously not been naturally observed, and a recombinant RSV B9320 virus engineered to have those 4 mutations in the binding site showed a shift in nirsevimab susceptibility. These 2 viruses containing resistance-associated mutations were identified in nasal samples from nirsevimab-dosed subjects who were hospitalised for LRTI.

TABLE 12

Amino Acid Variation Within the Nirsevimab Binding Site of F and Susceptibility Profiles

| RSV Subtype | Amino Acid Variations Identified in the Nirsevimab Binding Site | Subject ID | No of Sequences [a] Placebo | Nirsevimab | Nirsevimab $IC_{50}$ (ng/mL) | Fold Change to Reference Virus |
|---|---|---|---|---|---|---|
| RSV A | K209R | 20029290003<br>20029290004 | 0 | 2 | 4.2 [b] | 0.8 [b] |
| | N208S | 20029560006 | 0 | 1 | 54161 [c] | 24618 [c] |

TABLE 12-continued

Amino Acid Variation Within the Nirsevimab Binding Site of F and Susceptibility Profiles

| RSV Subtype | Amino Acid Variations Identified in the Nirsevimab Binding Site | Subject ID | No of Sequences [a] Placebo | Nirsevimab | Nirsevimab $IC_{50}$ (ng/mL) | Fold Change to Reference Virus |
|---|---|---|---|---|---|---|
| RSV B | I206M, Q209R | Multiple [d] | 12 | 5 | 0.4 [c] | 0.1 [c] |
| | I64I/T, K68K/E, I206M, Q209R | 20029540026 | 0 | 1 | >ULOQ | >72 [e] |

IC50 = half-maximal inhibitory concentration; ID = identification; No = number; RSV = respiratory syncytial vims; ULOQ = upper limit of quantification.

[e] Total number of RSV A and RSV B sequences were 53 and 50, respectively

[f] Described in report ID8897-0013

[g] Described in Zhu et al., 2018 J Infect Dis. 218(4):572-80.

[h] Subject IDs: 20030680022, 20033400003, 20034020002, 20034470001, 20034150008, 20032830004, 20033140005, 20032860005, 20029480034, 20030780004, 20032760007, 20029980006, 20029980007, 20030680014, 20032820006, 20030070001, 20029600002.

[i] Recombinant virus constructed and tested in neutralization assay contained I64T + K68E + I206M + Q209R amino acids.

Example 2

The results of the Phase 2b Study (see Example 1) demonstrated the clinical efficacy of a single 50-mg IM nirsevimab dose in preterm infants with gestational age ranging from 29 to <35 weeks. Further analysis determined that the fixed 50-mg dose evaluated in Example 1 resulted in a wide distribution of weight-normalised doses with an average of 13.2 mg/kg (interquartile range [IQR], 8.33, 17.2 mg/kg) and 83 unique dose levels amongst 968 infants that received nirsevimab. This broad distribution of dose levels facilitated exposure-response analyses without studying multiple fixed doses in this population or potentially error-prone, individualised weight-based doses.

Population-PK and exposure-response analyses were conducted with the following aims: 1) characterise relevant sources of inter-subject variability in nirsevimab PK in adults and premature infants, 2) explore the relationship between nirsevimab serum exposure and the primary efficacy outcome of medically attended RSV-confirmed LRTI, and 3) conduct dose-optimisation analysis to identify clinical dose(s) for future studies.

Study Data

The population pharmacokinetic (popPK) dataset included clinical serum pharmacokinetic (PK) data from the Phase 1 study in healthy adult volunteers (Griffin et al. 2017, Antimicrob Agents Chemother. 61(3), pii: e01714-16), the Phase 1b/2a study in healthy preterm infants 32 to <35 weeks gestational age (GA) (Domachowske et al. Pediatr Infect Dis J. 2018; 37(9):886-892), and the Phase 2b study in healthy preterm infants 29 to <35 weeks GA (Example 1). The exposure-response analysis dataset consists of the efficacy data from Phase 2b and includes the empirical Bayes estimates from the popPK analysis (based on 1530 concentrations from 102 adults and total 2348 concentrations from 988 infants with 43 and 134 concentrations below the limit of quantitation, respectively.)

Sample and Data Collection

Details of the study designs, doses, and populations are outlined in Table 13.

TABLE 13

Summary of Clinical Studies Included in the PK Analysis Dataset

| Study # Phase/Status | Study Design/ Objective | Population (Npk; N BLQ) | Study Drug Dose and Route | PK Sampling Time | ADA |
|---|---|---|---|---|---|
| D5290C00001 Phase I Completed | Design: Single Ascending Dose, R, DB, PC Objective: Safety, PK | Healthy adults 182 (1530: 43) | IV: 300 mg (n = 6), 1000 mg (n = 6) 3000 mg (n = 6) IM: 100 mg (n = 6); 300 mg (n = 78) | 0, 8 h, and on Study Day 2, 4, 6, 8, 15 22, 31, 61, 91, 121, 151, 181, 271, and 361 | Study Day 6 31, 91, 181, and 361 |
| D529QC0002 Phase 1b/2a Completed | Design; Single Ascending Dose, R, DB, PC Objective: Safety, PK | Healthy preterm infants 32 to < 35 weeks GA entering their first RSV season [a] 71 (278; 53) | IM: 10 mg (a = 8), 25 mg (n = 31), 50 mg (n = 32) | Study Day 0, 8, 31, 151, 361 | Study Day 31, 151, and 361 |

TABLE 13-continued

| Summary of Clinical Studies Included in the PK Analysis Dataset | | | | | |
|---|---|---|---|---|---|
| Study # Phase/Status | Study Design/ Objective | Population (Npk; N BLQ) | Study Drug Dose and Route | PK Sampling Time | ADA |
| D5290C00003 Phase 2b Pivotal Completed b* | Design Single Dose R, DB, PC Objective: Safety, efficacy, PK | Healthy preterm infants 29 to < 35 weeks GA and ≤ 8 months of age entering their first RSV season [a] 917(2373; 84) | IM: 50 mg (n = 968) | Study Day 91, 151, 361 | Study Day 91, 151, and 361 |

DB = double-blind; GA = gestational age; IM = intramuscular; IV = intravenous; PC = placebo controlled; PK = pharmacokinetic; R = randomised: RSV = respiratory syncytial virus.
[a] Preterm infant population not eligible to receive palivizumab per local guidelines.
[b] Results from the primary analysis are presented in the Briefrag Document Section 3.3.1; final analyses will be included in the updated Investigator's Brochure (planned early 2019).
[c] Liquid formulation. All other studies used a lyophiliized formulation of the study drug Bioanalytical Methods Nirsevimab concentrations in human serum samples were measured using a validated fluorescence ELISA method (with a Lower Limit of Quantification (LLOQ) value of 0.5 μg/mL. An electrochemiluminescent (ECL), solution-phase, bridging immunoassay was used for detection, confirmation, and titration of anti-drug antibody (ADA) in human serum.

Dataset Preparation and Handling

PK and clinical efficacy data were assembled using SAS (SAS Institute Inc., Cary, NC, USA) and R (R Foundation for Statistical Computing, Vienna, Austria) software. Data definition table and specifications were used to implement SAS programs followed by validation and quality control to ensure data consistency, reliability, and accuracy for all original or derived variables. The popPK data included demographics related parameters, for example, as baseline and time-varying age and bodyweight, sex, ethnicity, race, gestational age, and geographical location. Derived parameters included postmenstrual age, estimated as the sum of the gestational and the chronological age. Imputation methods for missing baseline or post-baseline bodyweight have previously been described (Robbie et al. 2013 Antimicrob Agents Chemother. 57:6147— 53.) The exposure-response dataset was assembled by merging a data-frame containing the estimated individual PK parameters output from the NONMEM program (Icon plc, Dublin, Ireland) such as baseline clearance, projected $AUC_{inf}$, $AUC_{0-inf}$, $AUC_{0-150}$, with the demographic dataset for Phase 2b study, using R software.

Data Disposition

Serum PK data from all subjects dosed with nirsevimab in Phase 1 and Phase 1b/2a were included in the popPK analysis. For Phase 2b, 51 infants with no quantifiable post-dose PK were excluded. Consequently, only the remaining 917 subjects exposed to nirsevimab and the 479 infants from the placebo group were included in the exposure response analysis.

Population Pharmacokinetics and Exposure-Response Modeling Strategy

Population Pharmacokinetics: Structural and Statistical Model

Figure 7:
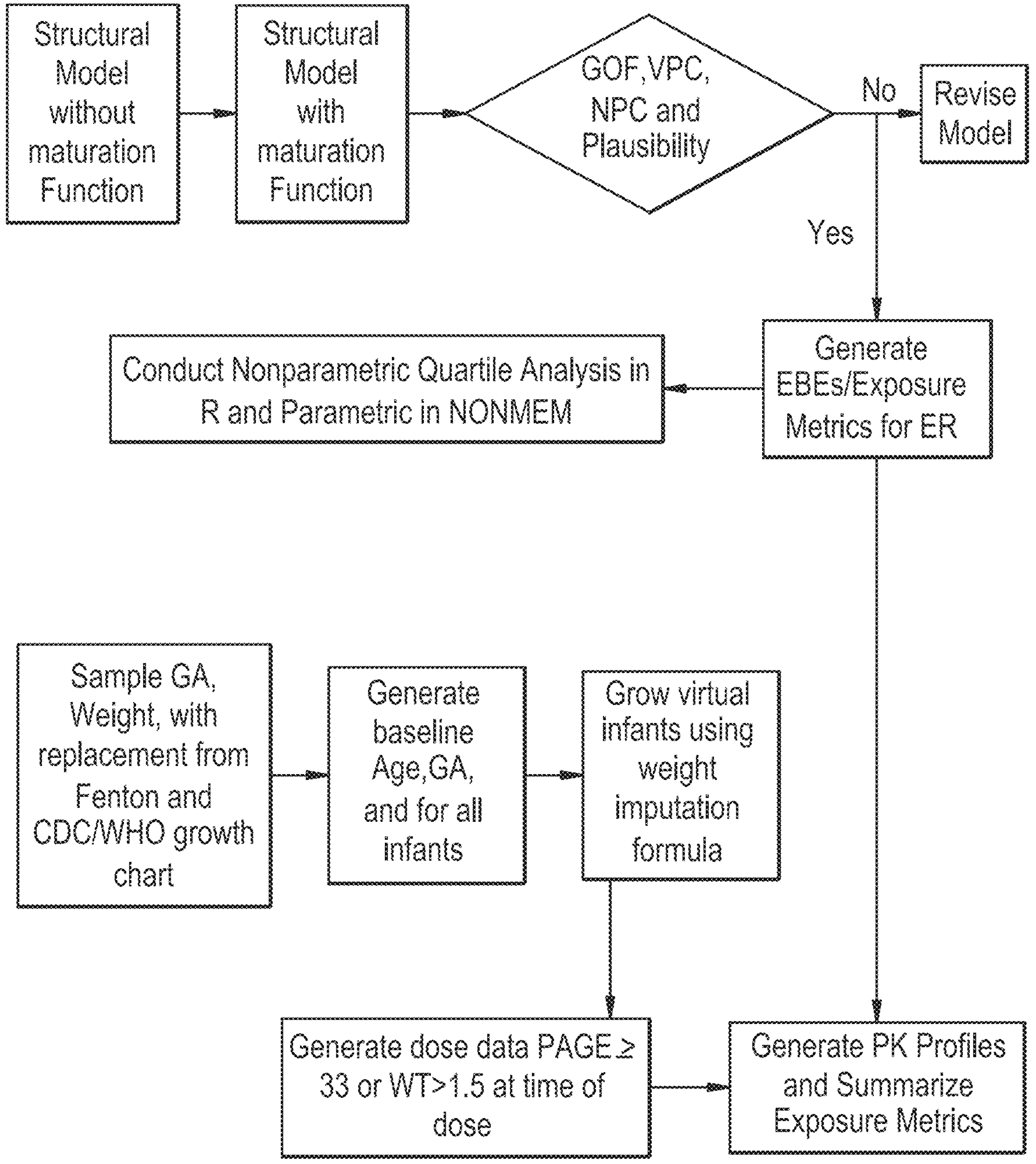
FIG. 7 shows a schematic of an exemplary population pharmacokinetic (popPK) analysis work flow, as further described in Example 2.
Figure 8:
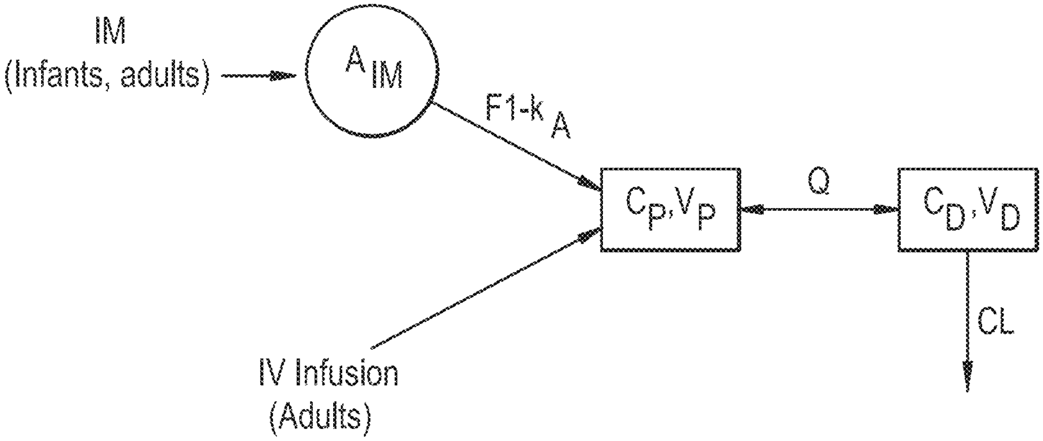
FIG. 8 shows a schematic of an exemplary population pharmacokinetic (popPK) structural model.

A two-compartment model with first order absorption, distribution clearance, as well as linear central elimination adequately characterized the PK data from the two studies. FIG. 7 and FIG. 8 show schematics of the popPK analysis work flow and the structural model, respectively.

Between subject variance (BSV) terms were estimated for systemic clearance, central volume of distribution, and absorption rate. Following allometric scaling of bodyweight on clearance and volume, the covariate model from the two studies only included the effects of bodyweight and maturation on clearance. Of note, the ETA distribution of clearance and absorption significantly deviated from the normality assumption for these parameters. Hence, a box-cox transformation was used to address this issue, which facilitated the simultaneous fitting of the densely sampled adult data and sparse PK data in infants. The strategy for the current work includes using the base estimate from the previous popPK model as the initial structural model for the analysis. The effects of allometrically scaled bodyweight, and maturation were assessed on clearance. Additional covariates such as anti-drug antibody on clearance, ethnicity on volume of distribution were also included in the covariate analysis. A full model approach followed by univariate elimination was used for final covariate selection. To maximize efficiency during parameter estimation, the PK parameters were mu-referenced, and Importance Sampling expectation maximization estimation algorithm was used within NONMEM. Details regarding the modeling methodology and workflow are outlined in FIG. 7.

Model Evaluation

Standard diagnostics and goodness of fit (GOF) plots were used to assess the adequacy of the popPK model. The plausibility and precision of the PK parameter estimates were also used as criteria for model selection. Using Perl speaks NONMEM (PsN) (Lindbom et al., 2004 Comput Methods Programs Biomed. 75(2):85-94), nonparametric bootstrap of 500 sampled datasets with replacement stratified by population (for example, adults versus infants) were conducted to assess the robustness of the model and generate confidence interval of the parameter estimates. For further assessment of the model adequacy, simulation-based visual predictive checks were conducted using the final covariate model parameters. Similar methodology was adopted for the qualification and evaluation of the exposure response model.

Exposure Metrics and Exposure-Response Analysis

The final covariate popPK model was used to generate empirical Bayesian estimates of the PK parameters for conducting the exposure-response (ER) analysis. Using R software, a cox proportional hazard model was fitted to the ER dataset to conduct semi-parametric exploratory quartile analysis for the primary efficacy outcome of Phase 2b (PCR-confirmed RSV positive medically-attended lower respiratory tract infection (MALRTI)).

Specifically, the incidence of the first MALRTI event was characterized using a time-to-event method. The survival function defined as the probability that an individual in the study experiences an event at time greater than 0. The probability of not having an MALRTI incident was estimated according to the following relationship shown in equation 1:

$$\mathrm{Surv}(t)=\exp(-\int_0^t \mathrm{haz}(t)dt) \quad (1)$$

Survival at any time t=exponent (– integral of instantaneous hazard dt).

The probability density function, which is also in this case the probability of MALRTI at any time t, was estimated as the product of the instantaneous hazard and the survival at time t as shown in equation 2.

$$pdf(t)=\mathrm{haz}(t)*\exp(-\int_0^t \mathrm{haz}(t)dt) \quad (2)$$

The probability density function was determined for infants with an MALRTI incident at time=t while the survival function was used for infants with right censored efficacy data, for example, no known MALRTI incidence over the time of interest (150 days post dose), or discontinued study, or removed consent prior to the censored time. Notably, Schoenfeld residual plots were evaluated to assess the constant hazard assumption for the exploratory model over the 150-day observation period.

NONMEM was used to conduct a multivariate ER analysis to identify influential covariates affecting the risk of MALRTI in infants in Phase 2b study (Table 14). Various parametric distributions, such as Weibull, and Gompertz, were evaluated during base model development. The Laplacian method was used in NONMEM to determine the Objective function and the log likelihood function. The final model was bootstrapped, and visual predictive checks were generated and stratified by the relevant covariates.

TABLE 14

Covariates Screened in the Hazard Model

| Covariate | Type | Parameter Assessed |
|---|---|---|
| Projected $AUC_{inf}$ | Continuous/ Categorical | Baseline hazard and Shape (if Weibull) |
| Region | Categorical | Baseline hazard and Shape (if Weibull) |
| Weight | Continuous | Baseline hazard and Shape (if Weibull) |
| Postmenstrual Age | Continuous | Baseline hazard and Shape (if Weiball) |

Simulation Methodology

The final popPK model was used to predict nirsevimab serum PK in late term to term infants (GA >35, Phase 3 Study), and preterm infants as well as children with congenital heart and lung disease (GA<29, CHD/CLD, Phase 2/3). Baseline characteristics for the virtual infants were generated using random sampling with replacement from Fenton's growth chart (Fenton and Kim, 2013 BMC Pediatrics. 13:59-72) or Olsen et al. (2015 Pediatrics 135:e572-81) for premature infants and the CDC/WHO chart (available on the worldwide web at www.cdc.gov/growthcharts/who/girls_length_weight.htm) for the term to late term infants. Of note, the virtual infants were limited to a minimum of 36 weeks postmenstrual age at baseline to mimic the clinical course for preterm infants, that is, infants will not be dosed until clinically stable at 34 weeks or higher postmenstrual age in NICU. To capture the effects of maturation, time-varying bodyweight were determined using the previously described imputation algorithm for bodyweight. PK profile and exposure metrics were summarized and tabulated for virtual infants for a single RSV season for the Phase 3 population and two consecutive seasons for the Phase 2/3 population.

Pharmacokinetic Results

Patient Characteristics

Figure 9A:
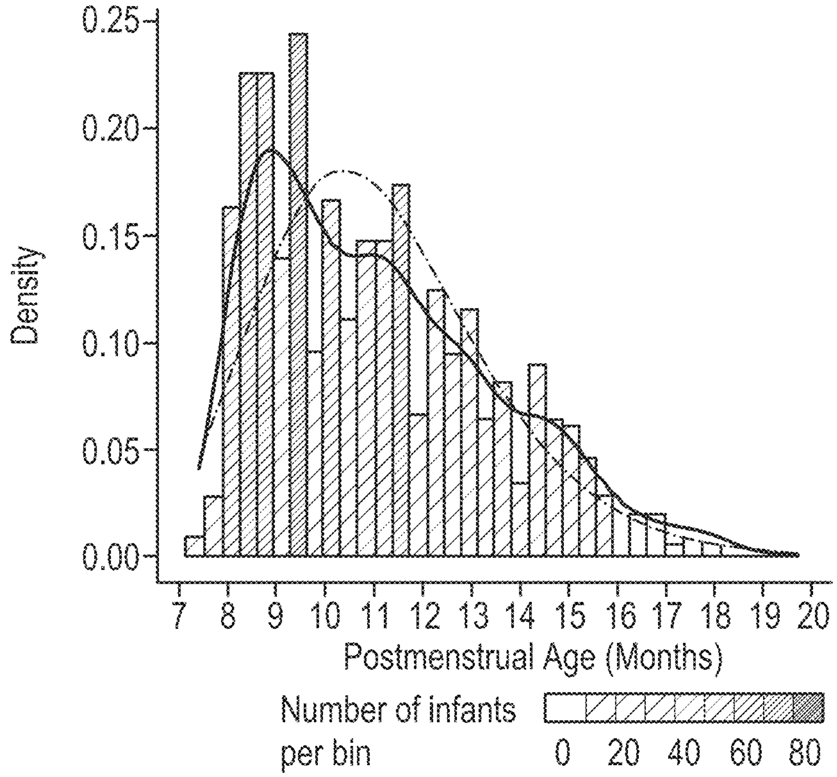
FIG. 9A shows postmenstrual age of infants exposed to nirsevimab in Phase 1b/2a and Phase 2b.
Figure 9B:
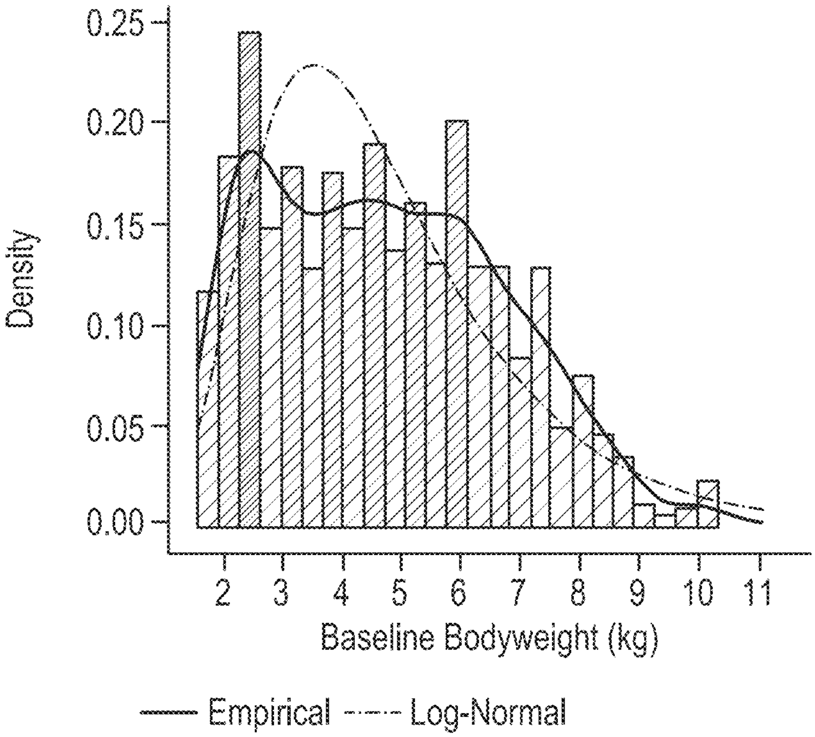
FIG. 9B shows baseline bodyweight distribution of infants exposed to nirsevimab in Phase 1b/2a and Phase 2b.
Figure 10:
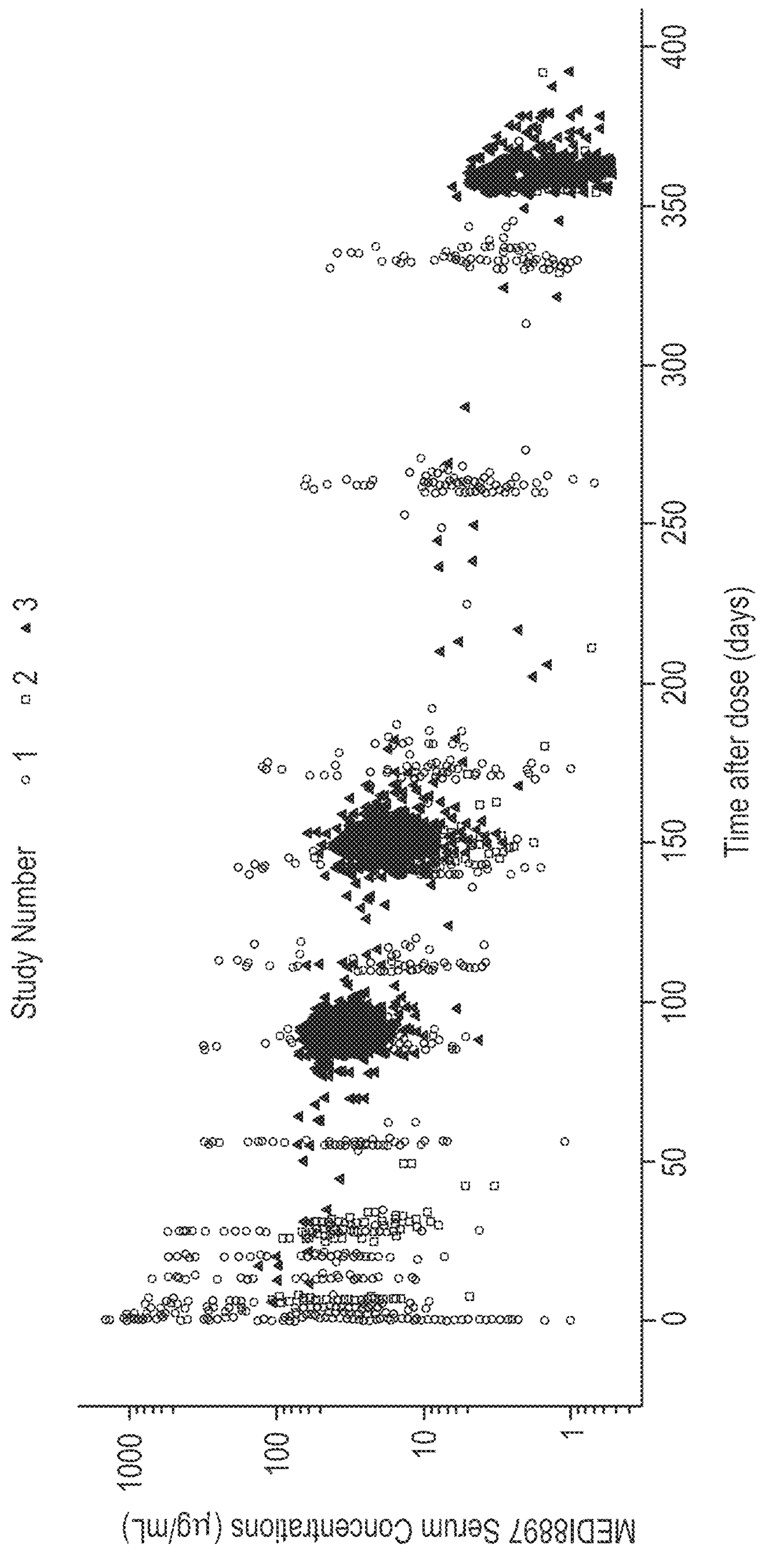
FIG. 10 shows distribution of available PK Data by study. Study 1—Phase 1 study in healthy adult volunteers (Griffin et al. 2017, Antimicrob Agents Chemother. 61(3), pii: e01714-16); Study 2—the Phase 1b/2a study in healthy preterm infants 32 to <35 weeks gestational age (GA) (Domachowske et al. Pediatr Infect Dis J. 2018; 37(9):886-892); and Study 3—the Phase 2b study in healthy preterm infants 29 to <35 weeks GA (Example 1).

The popPK analysis dataset included 3881 serum PK observations from 1090 individuals. Baseline characteristics are outlined in Table 15. The median (range) baseline postnatal and postmenstrual age ranged from 3 months (0.1-11.9 months) and 13.9 months (7.4-19.7 months) respectively (FIG. 9A). Baseline bodyweight ranged from 1.6 kg to 11.1 kg with a median of 6.8 kg (FIG. 9B). This broad distribution of postnatal and postmenstrual age as well as bodyweight facilitated the characterization of size and maturation effects on PK parameters. Observed serum concentrations from all the studies are illustrated in FIG. 10 and Table 16

PopPK Covariate Model

The effects of prematurity on PK parameters were modeled using a first-order exponential function as illustrated in equations 3-4:

$$CL_i = CLpop*\left(\frac{WT_i}{70}\right)^{\theta 1}*\left(1-(1-\beta_{CL})*e^{\left(-\left(PAGE_i-\left(\frac{40}{4.25}\right)\right)*\frac{LN(2)}{T50_{CL}}\right)}\right)*e^{\eta CL} \quad (3)$$

$$V_i = Vpop*\left(\frac{WT_i}{70}\right)^{\theta 2}*e^{\eta V} \quad (4)$$

Beta CL (V) represents the fractional change in the clearance of a premature infant with respect to a term infant whilst the $T50_{CL}$ denotes the corresponding maturation half-life of the parameter with respect to that of an adult. PAGE represents the sum of gestational age and postnatal age in months for each infant. Gestational age for adults was imputed to 40 weeks.

Figure 11:
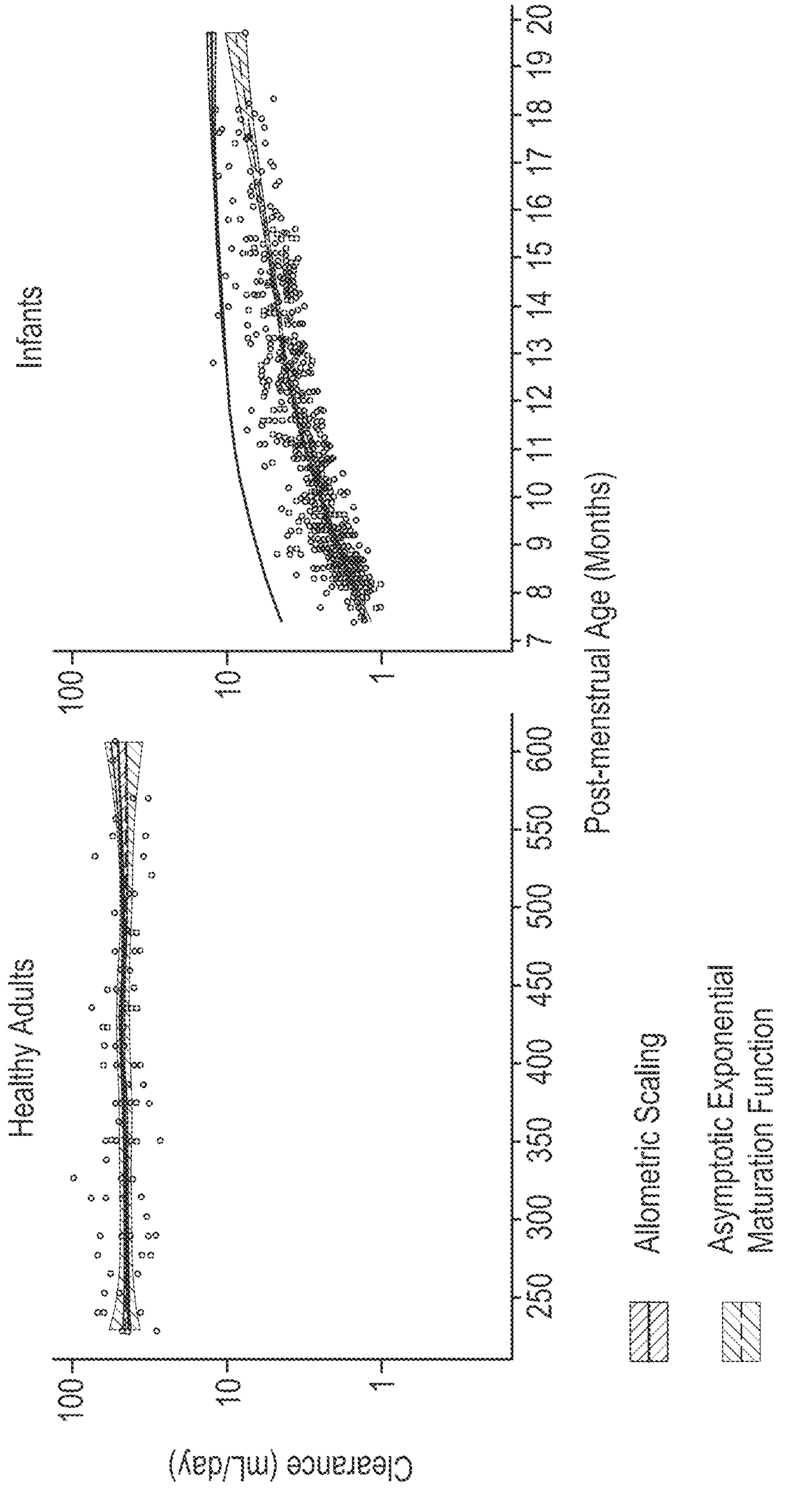
FIG. 11 shows effects of size and maturation on systemic clearance of nirsevimab.

The final population PK covariate model parameters with bootstrap estimates are shown in Table 17. Effect of size and maturation on clearance are depicted in FIG. 11.

Since inclusion of maturation on the central volume of distribution did not improve model fitting, only allometric scaling remained on this parameter. Based on the model analysis, between subject variance (BSV) was less than 30% for both clearance and volume of distribution. Baseline and time-varying bodyweight, along with postmenstrual age were the most influential predictors of clearance.

Model Evaluation

Figure 12:
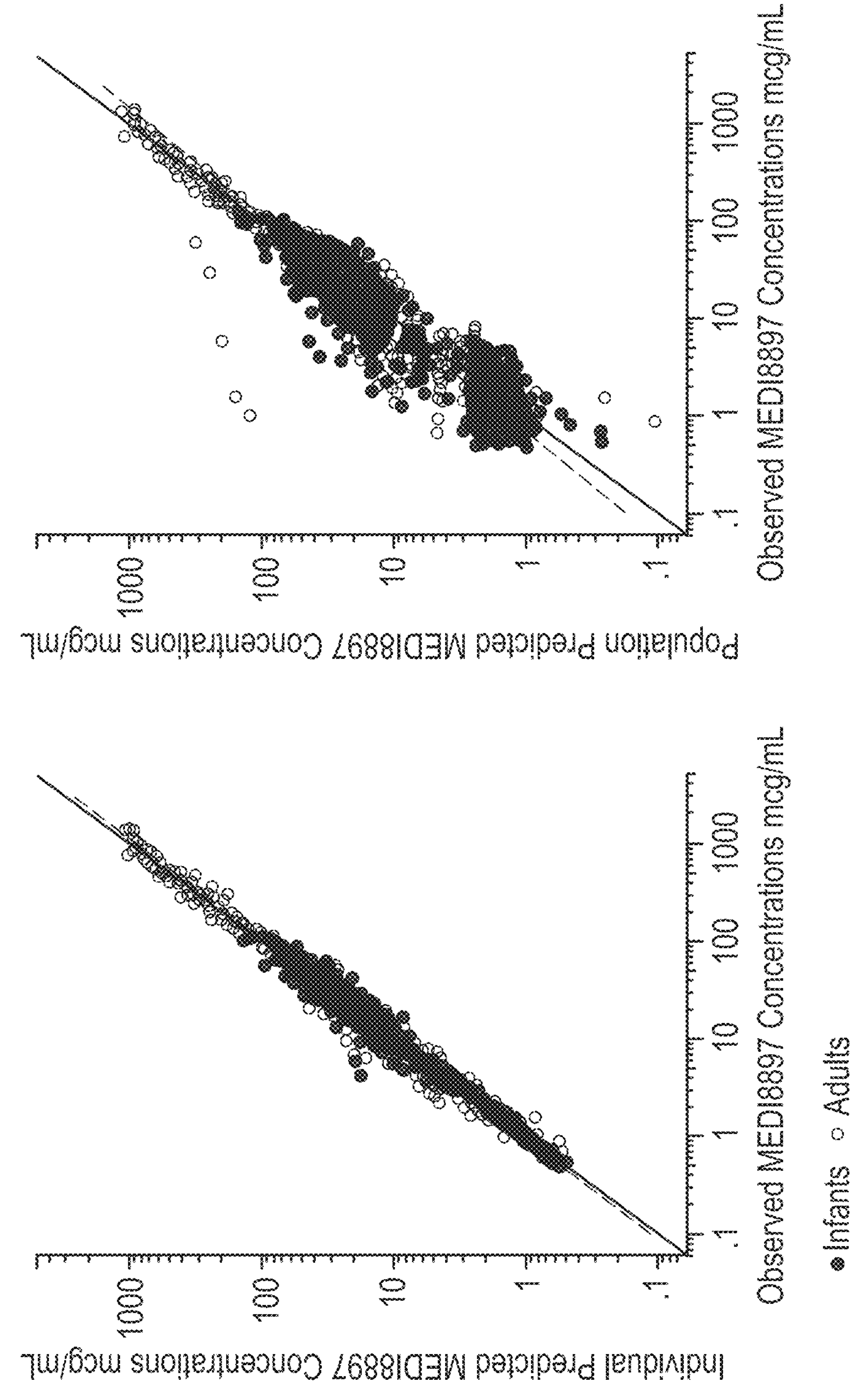
FIG. 12 shows a goodness of fit plot: Observed versus Individual (left panel) and Observed versus Population (right panel) predicted nirsevimab concentrations.
Figure 13A:
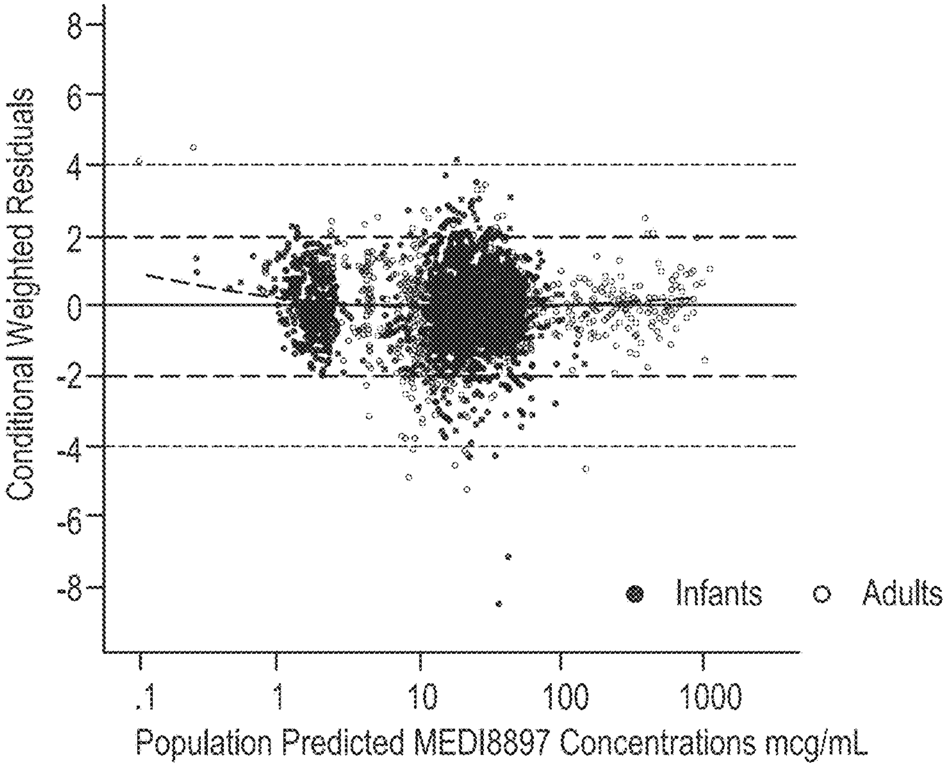
FIG. 13A-FIG. 13C show diagnostic plots of conditional weighted residuals.
Figure 13B:
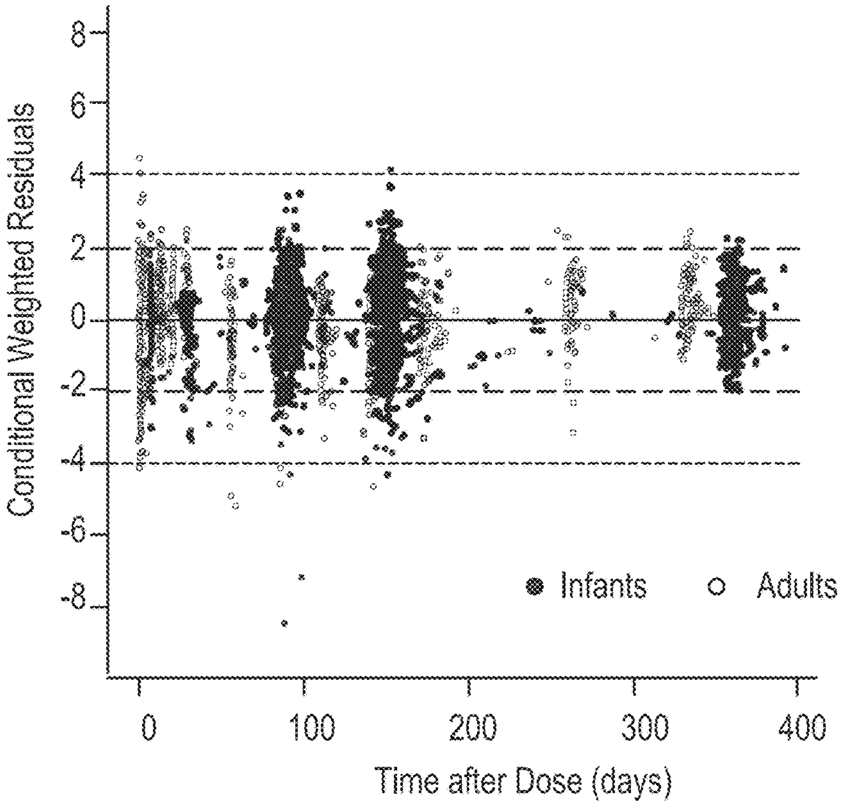
Figure 13C:
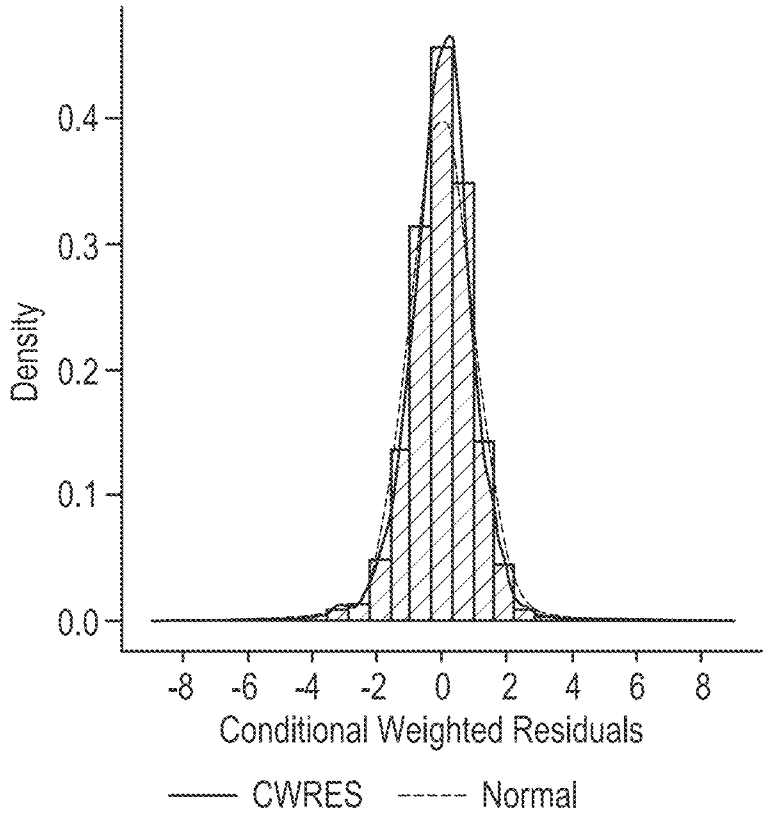
Figure 14:
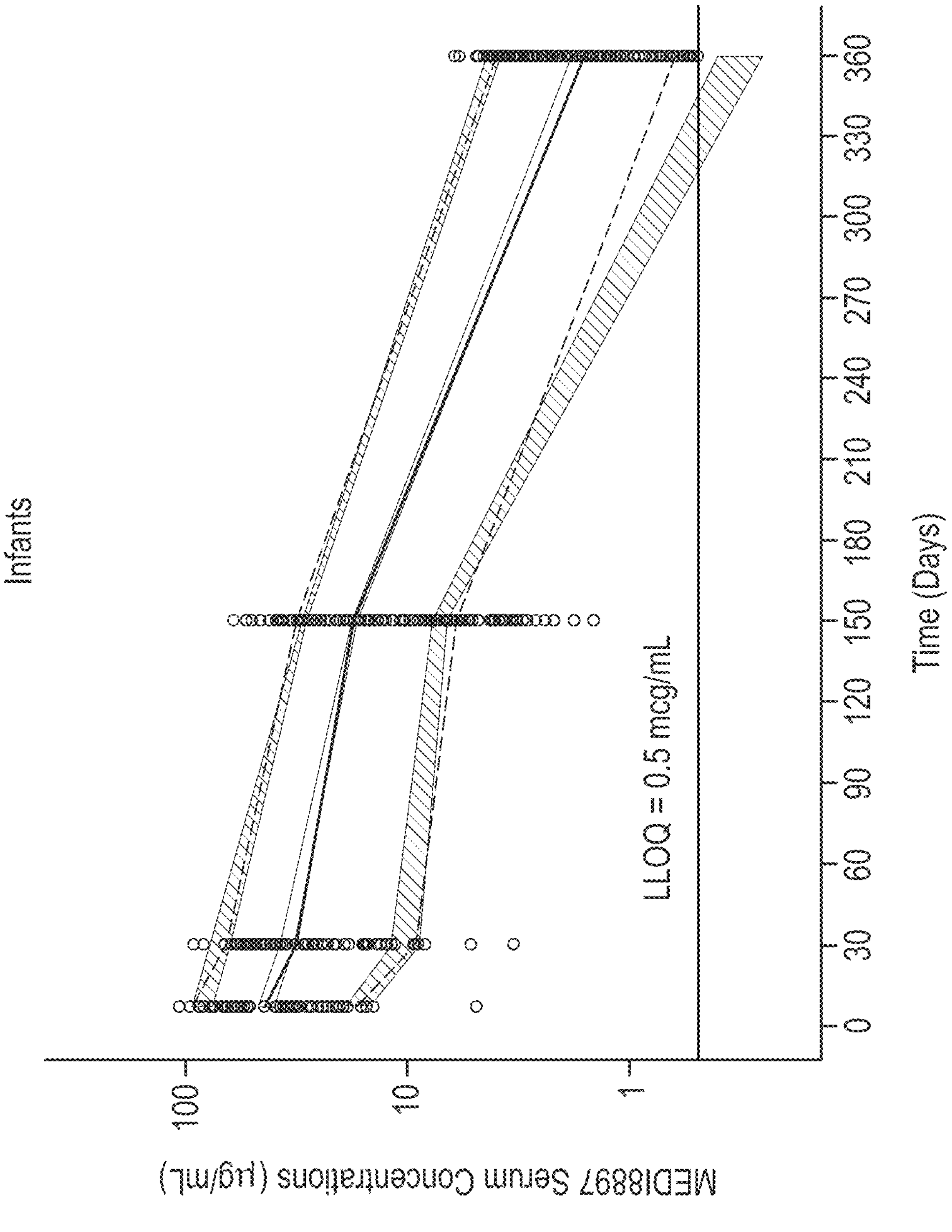
FIG. 14 shows a visual predictive check of infant PK Data by scheduled visit.

Inspection of the goodness of fit (FIG. 12, FIG. 13) and visual predictive check (FIG. 14) plots did not reveal any pertinent bias or misspecification in the model. The bootstrap results illustrate the stability of the final covariate model as all the bootstrapped datasets successfully converged. The 95% confidence interval (CI) of the bootstrap procedure included the median estimate of the original model for all parameters.

TABLE 15

Demographic and Baseline Characteristics of Subjects Included in the Population PK Analysis Datasets

| | Study D5290C00001 N = 102 Adults | Study D5290C00002 N = 71 Infants | Study D5290C00003 N = 968 Infants | p-value |
|---|---|---|---|---|
| Gestational Age (Weeks), Mean (SD) | 40.0 (0.00) | 33.1 (0.78) | 32.7 (1.42) | <0.001 |
| Baseline Age (Months), Mean (SD) | 377 (94.6) | 6.50 (2.64) | 3.27 (2.20) | 0.000 |
| Postmentrual Age (Months), Mean (SD) | 387 (94.6) | 14.3 (2.64) | 10.9 (2.22) | 0.000 |
| Baseline Bodyweight (kg), Mean (SD) | 78.0 (14.9) | 6.81 (1.89) | 4.59 (1.91) | 0.000 |
| Gender: Female, N (%) | 54 (52.93%) | 42 (59.2%) | 467 (48.2%) | 0.155 |
| Racial Background, N (%): | | | | |
| Native American | 0 (0.00%) | 1 (1.41%) | 0 (0.00%) | |
| Asian | 0 (0.00%) | 1 (1.41%) | 5 (0.52%) | |
| Black/African American | 56 (54.9%) | 41 (57.7%) | 187 (19.3%) | |
| Caucasian | 46 (45.1%) | 8 (11.3%) | 693 (71.7%) | |
| Hawarias | 0 (0.00%) | 0 (0.00%) | 8 (0.83%) | |
| Multiple Race | 0 (0.00%) | 2 (2.82%) | 12 (1.24%) | |
| Other | 0 (0.00%) | 18 (25.4%) | 62 (6.41%) | |
| Outcome: Event N (%) | 0 (%) | 0 (30) | 25 (2.58%) | |
| Excluded From PK Analysis, N (%) | 0 (0.00%) | 0 (0.00%) | 55 (5.68%) | 0.002 |
| Ethnicity, N(%): | | | | <0.001 |
| N/A | 0 (0.00%) | 0 (0.00%) | 1 (0.10%) | |
| Hispanic | 3 (2.94%) | 8 (11.3%) | 225 (23.230) | |
| Non-Hispanic | 99 (97.1%) | 63 (88.7%) | 742 (76.7%) | |
| Treatment, N(%): | | | | |
| MEDI8S97 10 mg IM | 0 (0.00%) | 8 (11.3%) | 0 (0.00%) | |
| MEDI8897 50 mg IM | 0 (0.00%) | 32 (45.1%) | 968 (100%) | |
| MEDI8897 25 mg IM | 0 (0.00%) | 31 (43.7%) | 0 (0.00%) | |
| MEDI8S97 100 mg IM | 5 (5.88%) | 0 (0.00%) | 0 (0.00%) | |
| MEDI8897 1000 mg IV | 6 (5.88%) | 0 (0.00%) | 0 (0.00%) | |
| MEDI8897 300 mg IM | 78 (76.5%) | 0 (0.00%) | 0 (0.00%) | |
| MEDI8897 300 mg IV | 6 (5.88%) | 0 (0.00%) | 0 (0.00%) | |
| MEDI8897 3000 mg IV | 6 (5.88%) | 0 (0.00%) | 0 (0.00%) | |

TABLE 16

Distribution of PK Samples from Infants Stratified by Study Visit

| | Study D5290C00002 N = 278 | Study D5290C00003 N = 2268 | p-value |
|---|---|---|---|
| Treatment: | | | |
| MEDI8897 10 MG IM | 29 (10.4%) | N/A | |
| MEDI8897 25 MG IM | 124 (44.6%) | N/A | |
| MEDI8897 50 mg IM | 125 (45.0%) | 2268 (100%) | |
| ADA Positive N(%) | 50 (28.8%) | 84 (3.70%) | |
| Hemisphere: | | | |
| Southern Hemisphere | 253 (91.0%) | 895 (39.5%) | <0.001 |
| Fraction LLOQ N (%) | 50 (18.0%) | 101 (4.45%) | <0.001 |
| PK Sample Visit: | | | <0.001 |
| Day 8 | 70 (25.2%) | N/A | |
| Day 31 | 70 (25.2%) | N/A | |
| Day 91 | 0 (0.00%) | 904 (39.9%) | |
| Day 151 | 70 (25.2%) | 872 (38.4%) | |
| Day 361 | 68 (24.5%) | 425 (18.7%) | |
| Unscheduled | 0 (0.00%) | 07 (2.95%) | |
| Excluded | 0 (0.00%) | 38 (1.68%) | 0.018 |

TABLE 17

Final Population PK Covariate Model Parameters with Bootstrap Estimates

| Parameter | Estimate (RSE %) | BSV Estimate % CV (RSE %) [Shrinkage %] | Bootstrap Estimate * | BSV Estimate % CV (95% CI) |
|---|---|---|---|---|
| CL(L/day)** | 4.3 | 26.7(13) [41] | 0.042 (0.04-0.045) | 28.9 (24.9-34.0) |
| Vp (L)** | 2990 | 24.3 (8) [13] | 3.08 (0.29-0.33) | 28.8 (22.6-35.7) |
| Q (L)** | 443 | | 0.44 (0.44-0.45) | |
| $V_D$ (L)** | 1780 | | 1.72 (1.66-1.78) | |
| $k_A$ (1/day) | 0.446 | 49 (21) [71] | 0.52 (0.44-0.59) | 58 (35.7-86.6) |
| F1 | 0.767 | | 0.75 (0.74-0.77) | |
| Box-cox CL Shape[a] | 1.05 | | 1.16 (0.40-2.0)) | |
| $\epsilon_{add}$ log scale | 0.205 | | 0.30 (0.45-0.10) | |
| Beta-CL | 0.292 | | 11.5 (7.5-17.2) | |
| $T_{50}$-CL (months) | 16.7 | | 0.60 (0.59-0.61) | |
| CLexp | 0.599 | | 0.89 (0.87-0.92) | |
| Vexp | 0.919 | | 0.27 (0.23-0.31) | |
| Box-cox $k_A$ Sharp[a] | 0.752 | | 45.2% (22.5-62.2) | |
| Corr $_{CL\text{-}Vp}$ | 53.4 (14.1%) | | | |
| Corr $_{Vp\text{-}kA}$ | 12.2 (126%) | | | |
| Corr $_{CL\text{-}kA}$ | −10 (133%) | | | |

*A total of 500 bootstrap sampled datasets ran with a 95% convergence rate

[a]Allometrically scaled to their respective exponent and a reference body weight of 70 kg $^b\eta_{trans,i} = \left(\frac{(e^{\eta_i})^{\theta n} - 1}{\theta n}\right)$ where $\eta_i$ and $\theta_n$ represents the untransformed between subject variance and the shape parameter, respectively.

Figure 15:
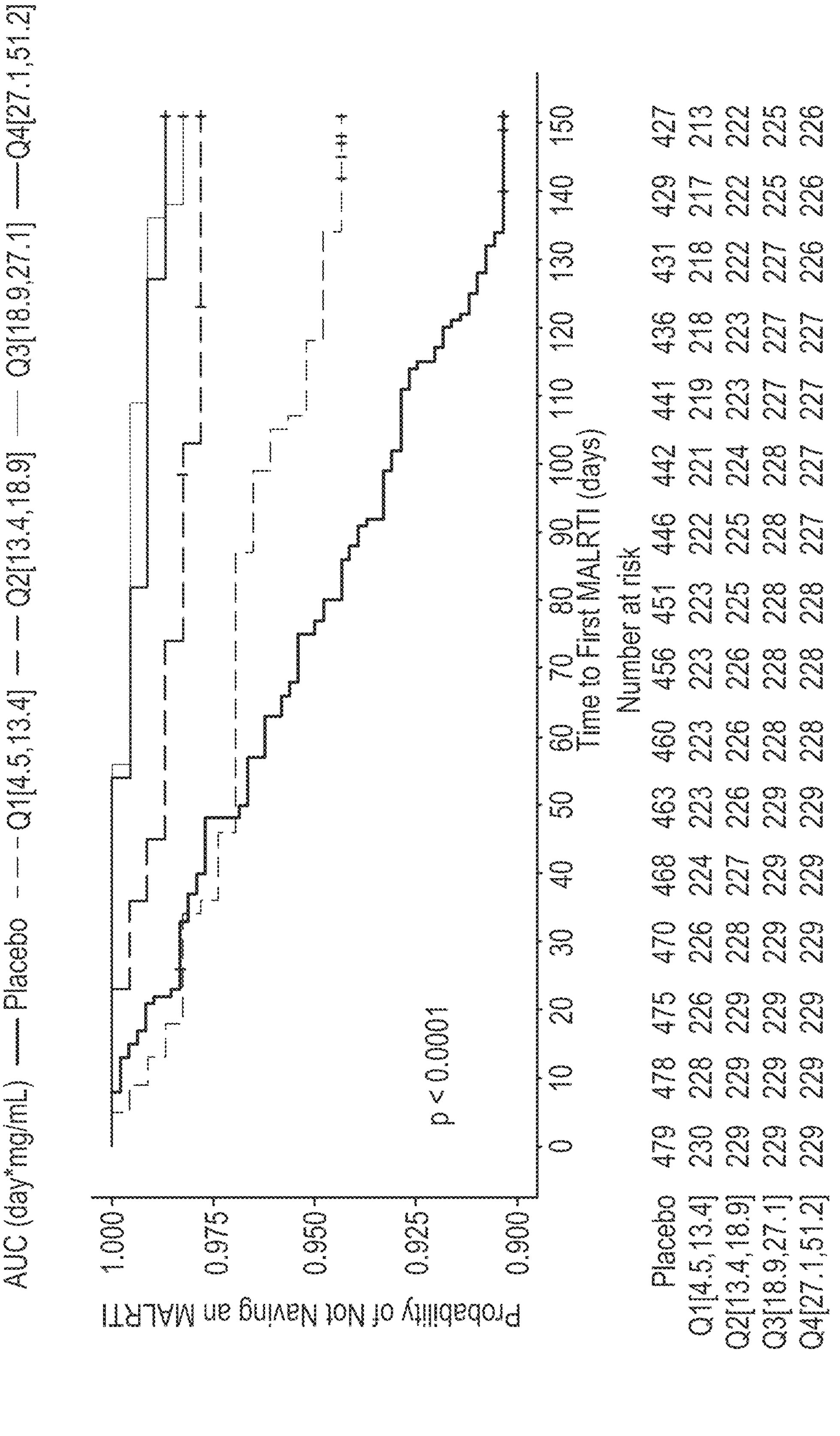
FIG. 15 shows a Kaplan-Meier plot of medically attended respiratory syncytial virus-confirmed lower respiratory tract infection (MALRTI) outcome in Phase 2b study stratified by AUC quartiles. $AUG_{0-\infty}$=area under the concentration-time curve from time 0 to infinity; MALRTI=medically attended respiratory syncytial virus-confirmed lower respiratory tract infection; Q=quartile. Figure presents data only from subjects in the As-treated Population who had at least one measurable post-dose nirsevimab serum concentration.

% CV = sqrt(exp($\omega^2$) −1); $Corr_{CL\text{-}Vp} = \omega_{CL\text{-}Vp}/(sqrt(\omega_{CL} * \omega_{Vp}))$ Exposure-Response Results The results of the cox proportional hazard model revealed a positive relationship between nirsevimab exposure and the risk of medically-attended lower respiratory tract infection (FIG. 15). The constant hazard assumption was not violated for any of the covariates assessed in the model. The estimates of the final model and bootstrapped parameters are shown in Table 18.

Figure 16:
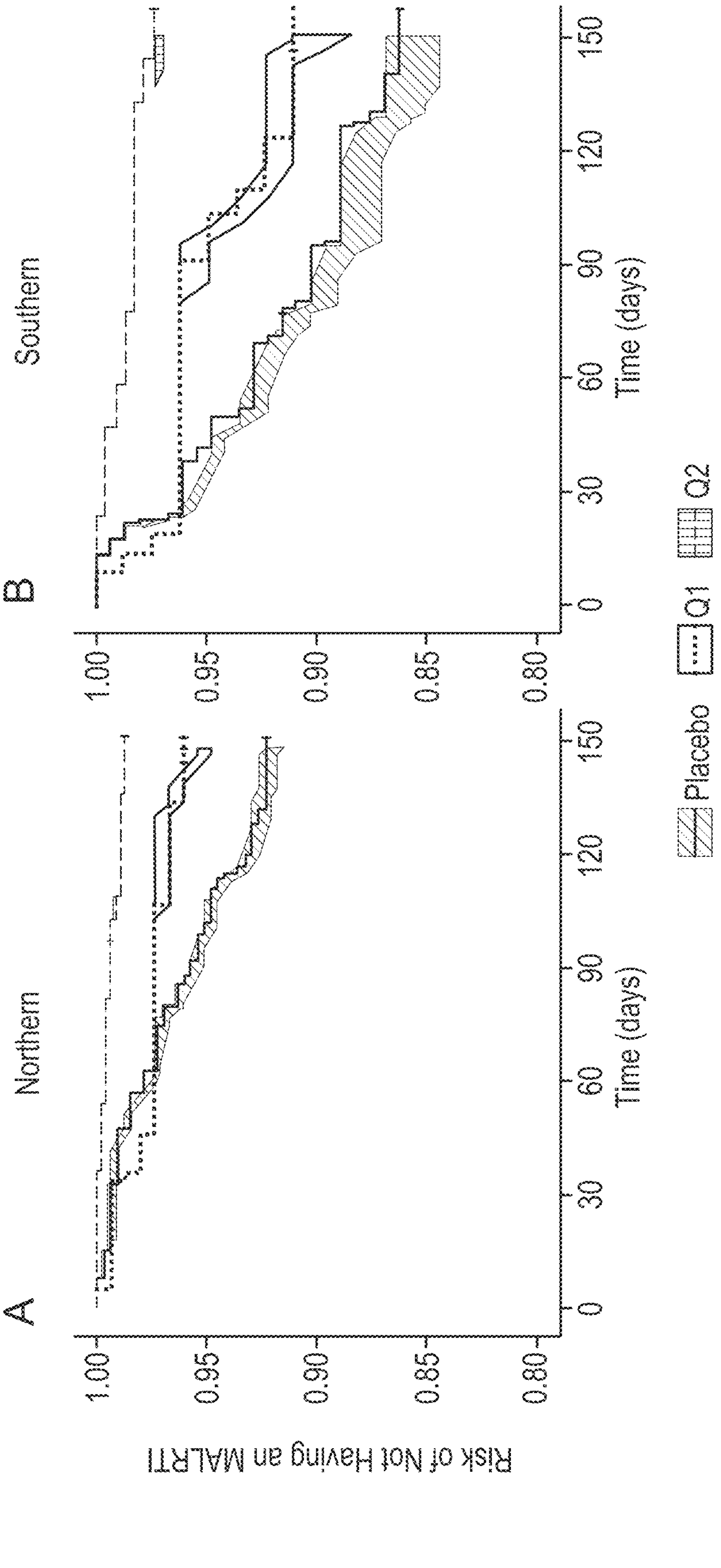
FIG. 16 shows a visual predictive check (VPC) of MALRTI by the geographical region, Northern in the left panel, Southern in the right panel. The indicated lines reflect the observed estimates for infants in the placebo group, those with serum AUC quartile 1, and AUC quartile 2, or greater. The area surrounding each line denotes the model-predicted 95% confidence interval around the median for each stratum.
Figure 17:
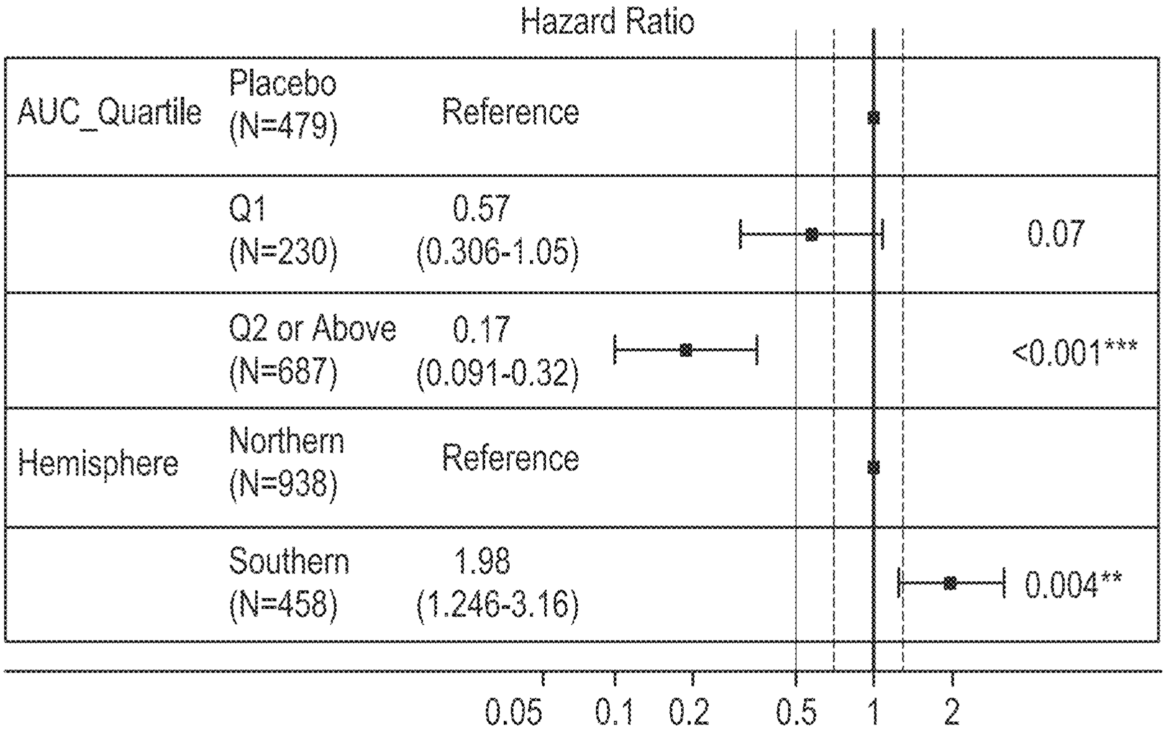
FIG. 17 shows a Forest plot of covariate effects in the final hazard model.

To further investigate these results, a parametric time-to-event analysis was conducted in NONMEM. An exponential hazard model adequately described the data as illustrated by the visual predictive check (VPC) (FIG. 16). The effects of geographical region and AUC quartiles on the risk of MALRTI were characterized and retained in the final covariate model (FIG. 17).

Figure 18:
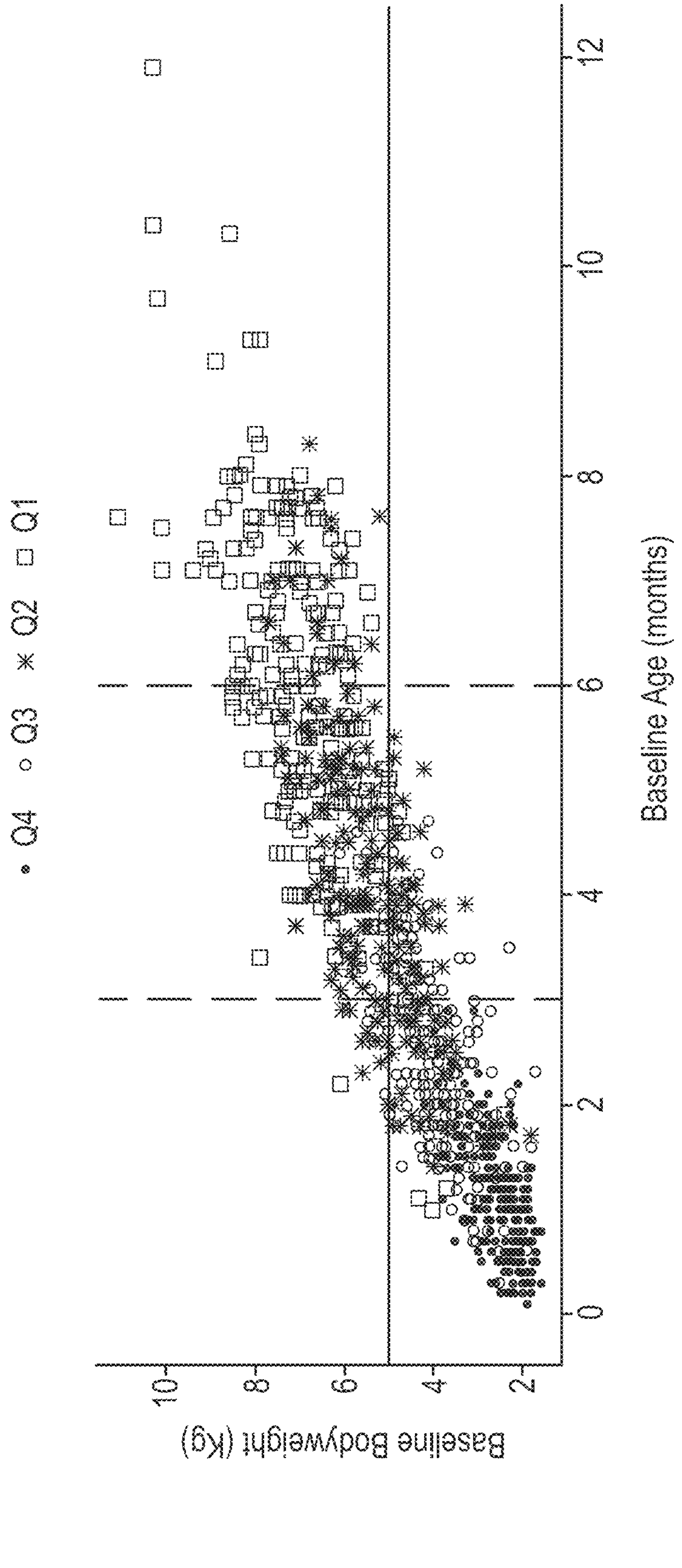
FIG. 18 shows distribution of exposure quartiles across age and bodyweight. $AUG_{0-\infty}$=area under the concentration-time curve from time 0 to infinity; Q=quartile. Figure presents data only from subjects in the As-treated Population who had at least one measurable post-dose nirsevimab serum concentration. The solid horizontal line at 5 kg and dashed vertical lines at 3 and 6 months highlight differences in Q1 distribution amongst various age and body weight ranges
Figure 19:
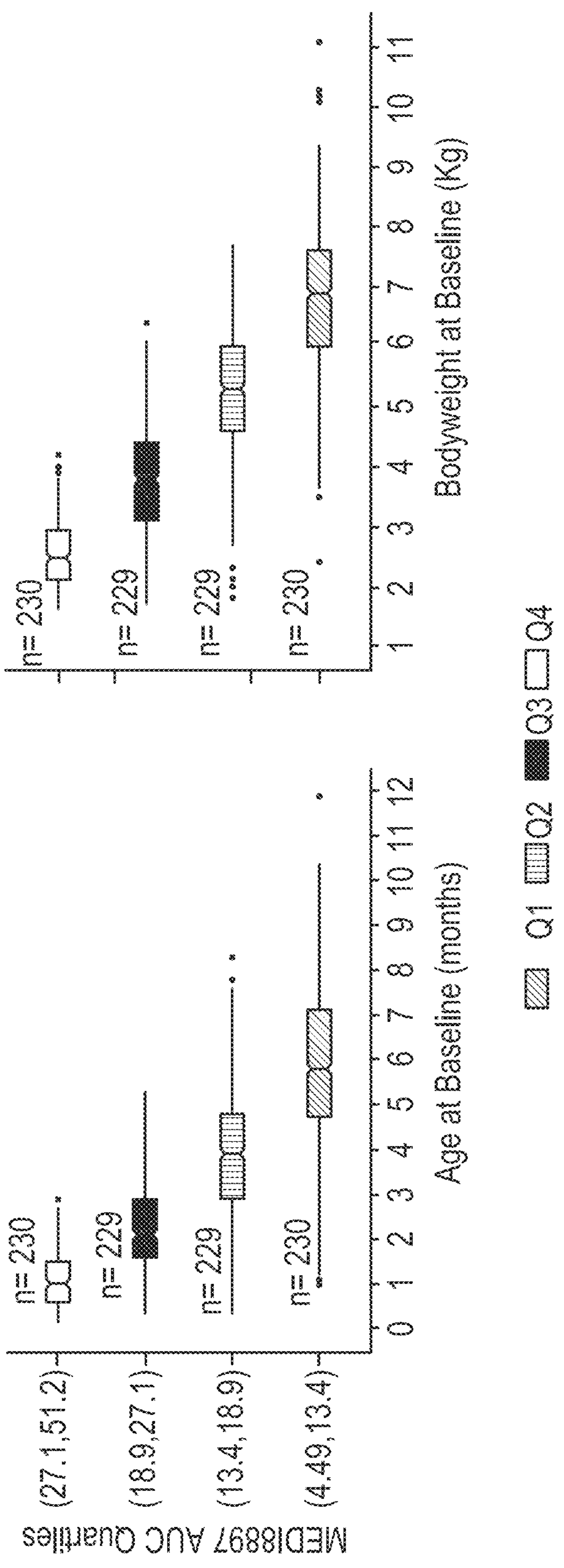
FIG. 19 shows effects of body weight and age on exposure and efficacy. The efficacy of nirsevimab efficacy in subjects in the lowest AUC quartile did not differ from placebo; AUC ranges in Q2 to Q4 were the in-vivo clinical efficacy target.

Given the marked effect of baseline bodyweight on clearance and consequently projected AUCia, a rank-based analysis was conducted using R software's Maxstat package to determine the optimal cut-point along the continuous distribution of body weight and weight-normalized doses to facilitate dose optimization for infant with suboptimal exposures (Hothorn and Lausen, 2003 Computational Statistics & Data Analysis. 43(2):121-137). A baseline bodyweight of 4.6 kg was determined to be the optimal weight cut-point from the analysis. In addition, exploratory analysis revealed a pertinent trend towards higher bodyweight for infants with Q1 serum AUC (FIG. 18, FIG. 19, & Table 19).

Figure 20:
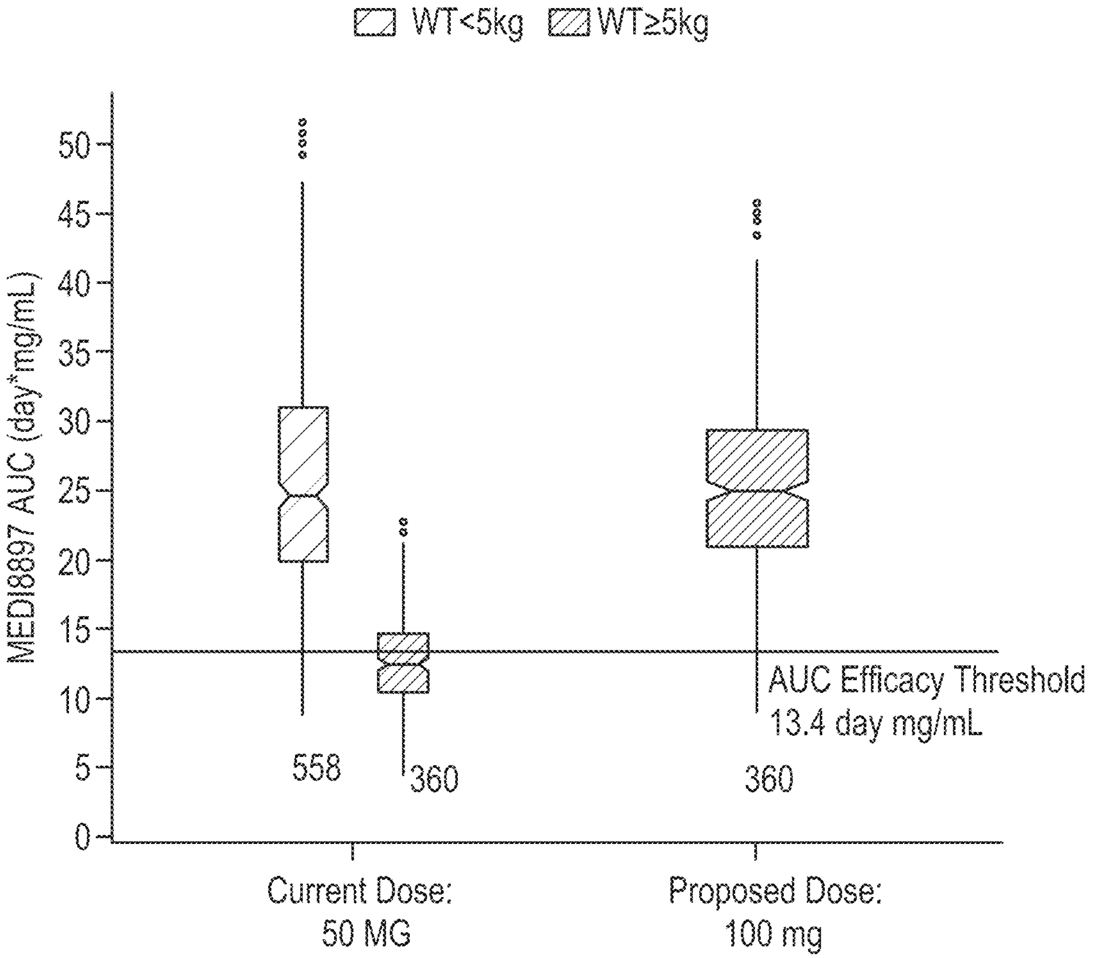
FIG. 20 shows predicted AUC distribution of the proposed dose of nirsevimab in the more than 5 kg in Phase 2b population to match exposures as observed in up to 5 kg in the first RSV Season. AUC=area under the concentration-time curve. The numbers above x-axis refer to the number of subjects in each category. The projected AUC values are estimated as the ratio of the administered dose and systemic clearance for all infants as derived from the population-PK model estimates. The projected AUC distribution in pink highlights the projected exposure for the 360 infants from the Phase 2b population weighing ≥5 kg when they are dosed with 50 mg (studied dose) versus 100 mg (proposed) nirsevimab. The boxplot in yellow illustrates the AUC distribution for infants from the Phase 2b population weighing <5 kg. Figure presents data only from subjects in the As-treated Population who had at least one measurable post-dose nirsevimab serum concentration.

Only 40% of the infants weighing 5 kg or higher had serum AUC ≥Q2 compared to 97% of those weighing up to 5 kg. Infants with AUC ≥Q2 have a lower risk of MALRTI with a hazard ratio (HR) and 95% confidence interval (CI) of 0.17 (0.09, 0.32), compared to the infants who received placebo or had serum AUC below 13.4 day·mg/mL. These results support a higher dose of 100 mg IM in infants with serum AUC below Q1 to match the exposure and consequently the benefit observed in infants with serum AUC ≥Q2 (FIG. 20).

TABLE 18

Parameter Table of the Final Model Estimate with Bootstrap

| Description | Model Estimate (% RSE) | Bootstrap Estimate (95% CI) |
|---|---|---|
| Baseline hazard (1/day) | 0.00051 (18.6) | 0.00052 (0.00034, 0.00072) |
| Lowest AUC Quartile (Q1) effect on baseline hazard | −0.569 (55.4) | −0.591 (−1.33, −0.0103) |
| Region effect on baseline hazard | 0.686 (34.7) | 0.675 (0.204, 1.14) |
| AUC > Q2 effect on baseline hazard | −1.77 (18.3) | −1.79 (−2.58, −1.18) |

$h(t) = \lambda_0 * exp(\beta_1 * AUC\_Q1 + \beta_2 * REGION + \beta_3 * AUC\_Q2)$

TABLE 19

Summary of Baseline Characteristics Stratified by AUC Quartiles

| | Placebo N = 479 | Q1 N = 230 | Q2 N = 229 | Q3 N = 229 | Q4 N = 229 |
|---|---|---|---|---|---|
| WT (kg) | 4.51 (1.96) | 6.83 (1.30) | 5.25 (1.06) | 3.71 (0.95) | 2.52 (0.56) |
| $C_{max}$ (μg/mL) | 0.00 (0.00) | 54.5 (7.89) | 62.4 (9.15) | 72.2 (13.2) | 82.7 (15.1) |
| Age (months) | 3.28 (2.31) | 5.79 (1.73) | 3.93 (1.44) | 2.22 (0.96) | 1.07 (0.59) |
| PAGE (months) | 10.8 (2.31) | 13.4 (1.72) | 11.5 (1.40) | 9.81 (0.94) | 8.61 (0.54) |

Simulation

Baseline characteristics for virtual infants were simulated using data for term and preterm infants from the CDC/WHO growth charts and Olsen et. al. (Pediatrics. 2015; 135:e572-81). These data were included in the childSDS package v0.6.4 in R software. Firstly, the virtual infants' data were sampled with replacement from the $3^{rd}$ to the $97^{th}$ percentile body weight with gestational age ranging from 24 to 40 weeks with a minimum baseline bodyweight of 1.5 kg at the time of dose administration. Subsequently, the simulation data was assembled to mimic the expected population for the phase 3 trial (>35 GA) and phase 2/3 trial (<29 GA or term infants with CHD/CLD) dosed at up to 8 months postnatal age. The simulation results (Table 20) further support the proposed dose of 100 mg for infants over 5 kg in the first RSV season. Over 95% of infants are expected to reach serum AUC above the target threshold. The average $C_{max}$ across all age groups are all within the safety margin or previously tolerated nirsevimab exposures. In addition, the PK parameters obtained from noncompartmental analysis of the simulated profiles are similar across age groups and doses, which further corroborates the adequacy of the exposure-matching approach for the proposed dosing strategy.

Figure 21:
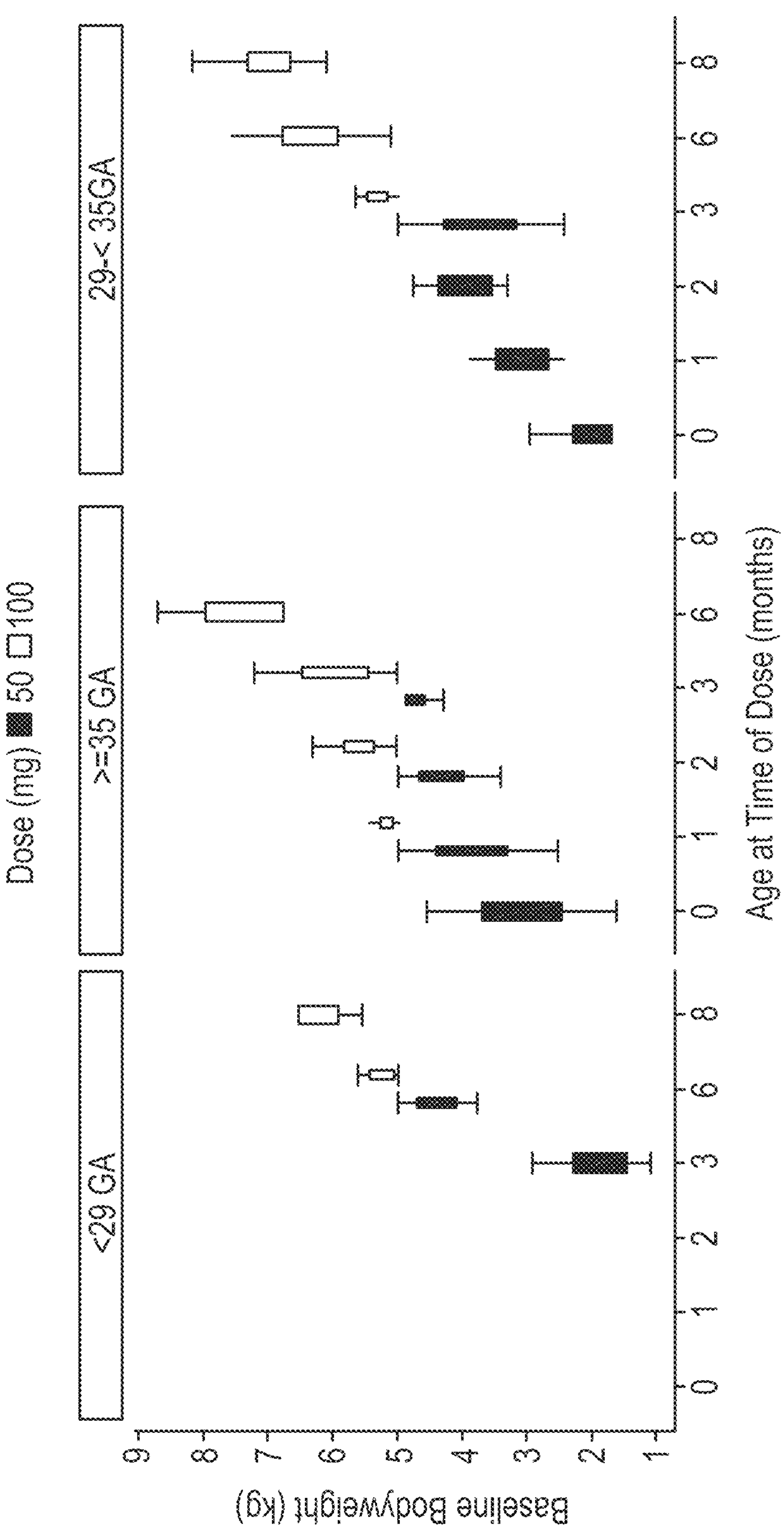
FIG. 21 shows distribution of age and bodyweight for virtual infants in Phase 3 and Phase 2/3 population in the $1^{st}$ RSV season. All virtual infants weighted 1.5 kg or >34 weeks gestational age (GA) at the time of the dose. Dose is a single fixed 50 mg IM dose or 100 mg IM dose. The boxes represent the interquartile range ($25^{th}$ to $75^{th}$ percentile), the top and bottom error bars show the largest value within 1.5 times the $75^{th}$ or the $25^{th}$ percentile, respectively.
Figure 22:
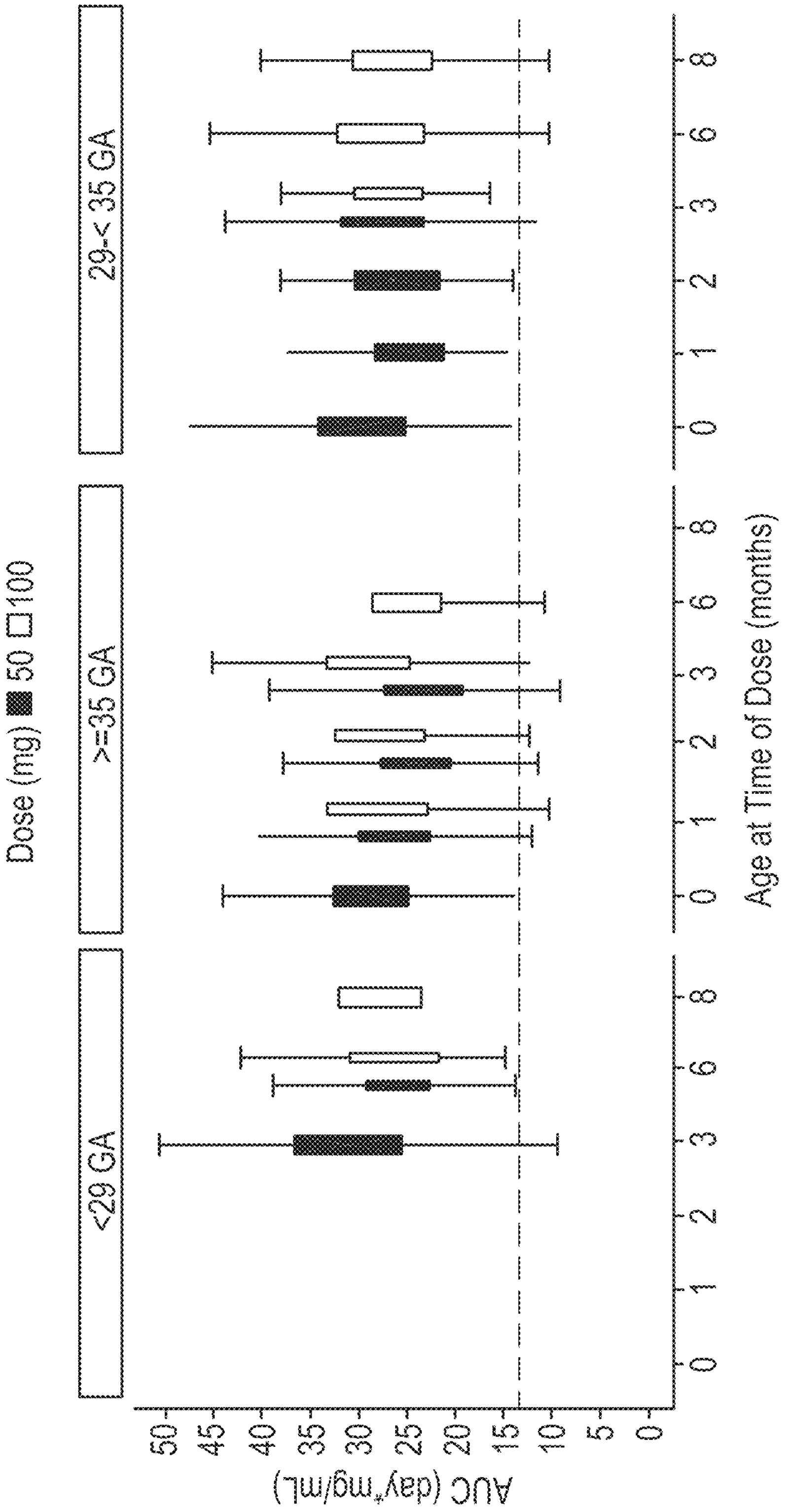
FIG. 22 shows predicted AUC for virtual infants in Phase 3 and Phase 2/3 Population in the $1^{st}$ RSV season. All virtual infants weighted 1.5 kg or >34 weeks gestational age (GA) at the time of the dose. Dose is a single fixed 50 mg IM dose or 100 mg IM dose. The dotted line reflects the target AUC threshold of 13.4 day·mg/mL. The boxes represent the interquartile range ($25^{th}$ to $75^{th}$ percentile), the top and bottom error bars show the largest value within 1.5 times the 75th or the 25th percentile, respectively.
Figure 23:
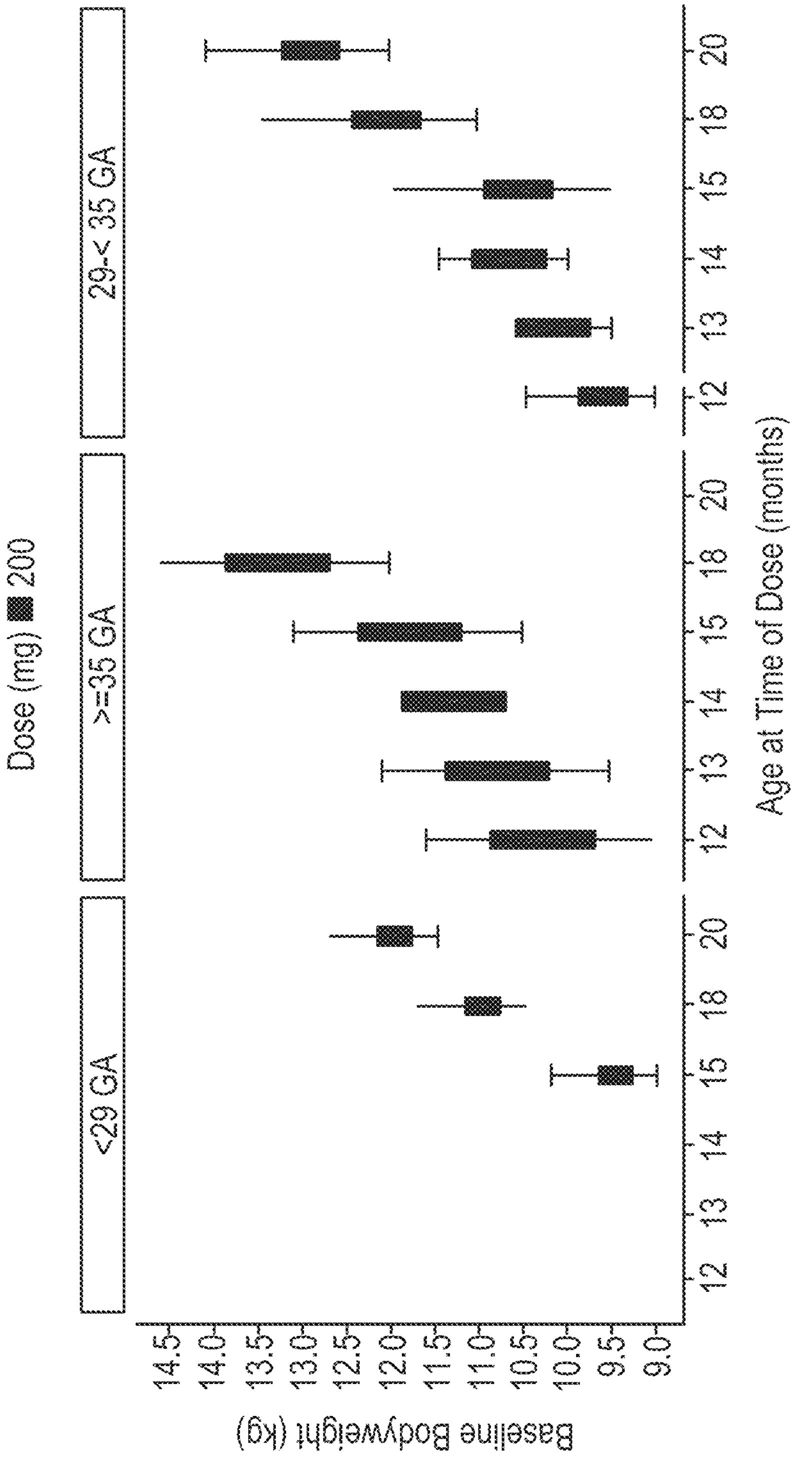
FIG. 23 shows distribution of age and bodyweight for virtual infants in Phase 2/3 population in the $2^{nd}$ RSV season. Dose is a single fixed 200 mg IM dose. The boxes represent the interquartile range ($25^{th}$ to $75^{th}$ percentile), the top and bottom error bars show the largest value within 1.5 times the $75^{th}$ or the $25^{th}$ percentile, respectively.
Figure 24:
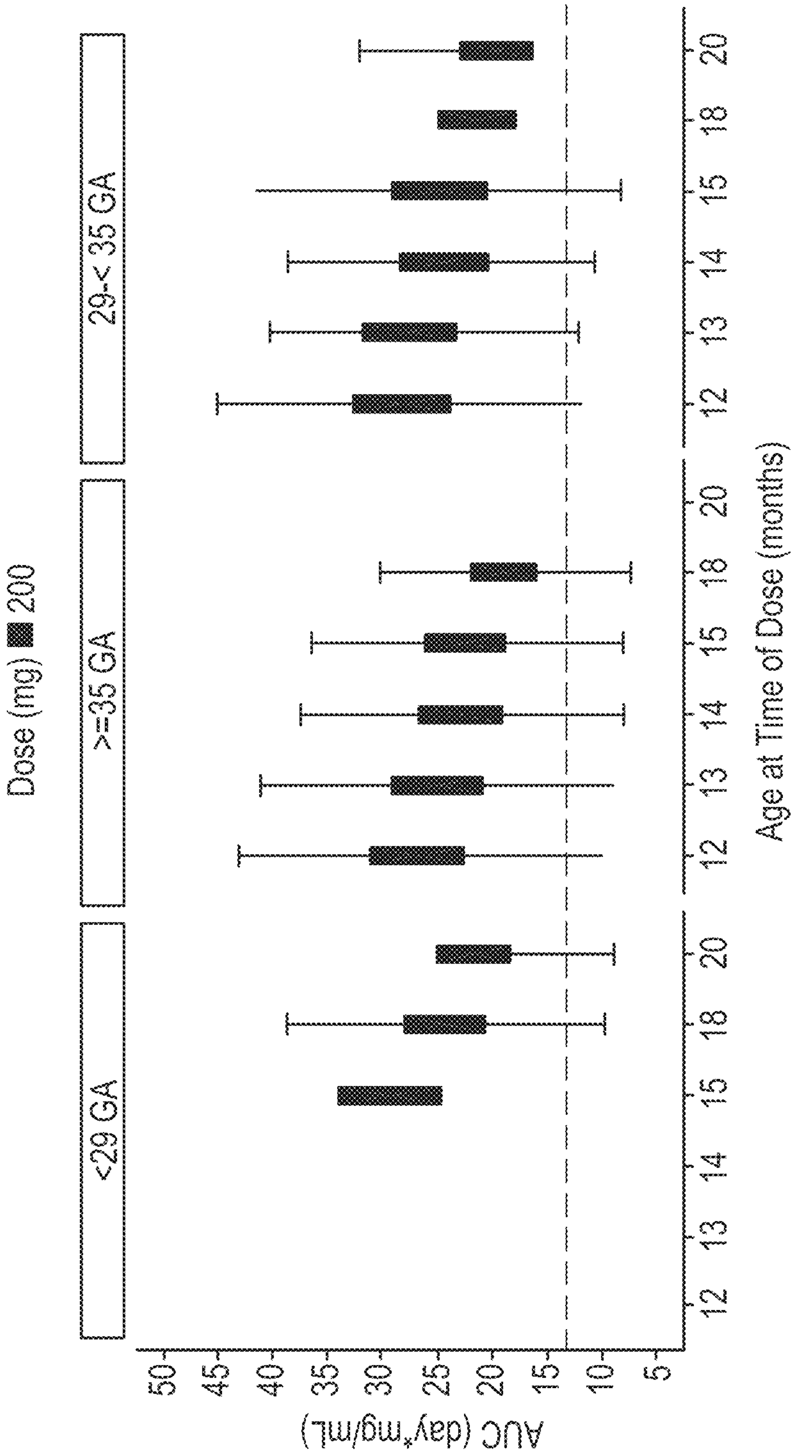
FIG. 24 shows predicted AUC for virtual infants in Phase 2/3 population in the $2^{nd}$ RSV season. Dose is a single fixed 200 mg IM dose. The dotted line reflects the target AUC threshold of 13.4 day·mg/mL. The boxes represent the interquartile range ($25^{th}$ to $75^{th}$ percentile), the top and bottom error bars show the largest value within 1.5 times the $75^{th}$ or the $25^{th}$ percentile, respectively.

With the proposed doses shown in Table 20 and the anticipated body weight distributions in $1^{st}$ (FIG. 21) and $2^{nd}$ (FIG. 23) RSV season, it is predicted that the AUCs will be similar, largely overlapping and above the target AUC in majority of the infants (FIG. 22, FIG. 24).

CONCLUSIONS

Based on the exposure-response analysis, a nirsevimab dose resulting in serum AUC above 13.4 day·mg/mL throughout the typical 5-month RSV season is anticipated to provide optimal protection against RSV in infants during the first year of life and high-risk children during the second year of life. Using the final popPK model, simulations indicate that a single fixed 50 mg dose (in infants <5 kg) or a 100 mg dose (in infants ≥5 kg) is expected to result in at least 80% of the population having an expected $AUG_{0-\infty}$ above 13.4 day·mg/mL in the first RSV season in the first year of life. Additionally, a single fixed 200-mg nirsevimab dose is expected to result in at least 80% of the population with expected $AUG_{0-\infty}$ being above 13.4 day·mg/mL and expected to be safe and effective for children in second year of life.

TABLE 20

Simulated Bodyweights and Exposures in the $1^{st}$ and $2^{nd}$ RSV Season

| | | <29 GA N = 1234 | 29-<35 GA N = 2905 | ≥35 GA N = 1993 |
|---|---|---|---|---|
| 50 mg Dose ($1^{st}$ RSV Season) | Bodyweight (kg) | 3.0 (1.3) | 3.7 (0.9) | 3.0 (1) |
| | PAGE (months) | 8.4 (1.5) | 8.8 (1.2) | 9.6 (1) |
| | $C_{max}$ (μg/mL) | 191 (82) | 173 (63) | 155 (55) |
| | Half-life (days) | 63.3 (29) | 62.7 (39) | 66.7 (40) |
| | Projected $AUC_{INF}$ | 27 (24) | 26.5 (24) | 25.7 (24) |
| | % Above AUC Threshold: | 99 | 99 | 99 |
| 100 mg Dose ($1^{st}$ RSV Season) | Bodyweight (kg) | 6.0 (0.5) | 6.5 (1) | 6.5 (0.7) |
| | PAGE (months) | 11.9 (0.8) | 13.3 (1.3) | 12.8 (1.7) |
| | $C_{max}$ (μg/mL) | 159 (31) | 155 (32) | 154 (32) |
| | Half-life (days) | 63.9 (26) | 62.6 (22) | 66.6 (40) |
| | Projected $AUC_{INF}$ | 27 (22) | 26 (3) | 26 (22) |
| | % Above AUC Threshold | 99 | 99 | 99 |
| 200 mg Dose ($2^{nd}$ RSV Season) | Bodyweight (kg) | 10.8 (1.1) | 11.3 (1.3) | 11.4 (1.2) |
| | PAGE (months) | 21.6 (2.2) | 22.9 (2.6) | 22.8 (2.1) |
| | $C_{max}$ (μg/mL) | 235 (62) | 221 (57) | 226 (62) |
| | Half-life (days) | <51 (41) | 60 (16) | 60 (19) |
| | Projected $AUC_{INF}$ | 24 (26) | 22 (26) | 23 (27) |
| | % Above AUC Threshold: | 97 | 95 | 95 |

Example 3

Microneutralization assays were performed as follows: Briefly, 2-fold serial dilutions of MAb were introduced into 384-well microtiter plates in HEp-2 cell culture medium at a volume of 15 μL/well. Subsequently, 15 μL of either RSV A2 or RSV B 9320 virus diluted into HEp-2 cell culture medium to concentration ranging from 80 to 150 pfu/well and was added to each well including control wells containing HEp-2 cell culture medium alone, and plates were incubated for 1.5 hours at 37° C. with 5% CO2. HEp-2 cells were added at $2.5\times10^5$ cells/mL in 30 μL to each well and the plates were incubated at 37° C. with 5% CO2. After 3 days for RSV A2 or 4 days for RSV B9320, medium was removed and 30 μL of ice cold 80% acetone/20% PBS was added to fix the cells.

Viral replication was measured by enzyme-linked immunosorbent assay (ELISA) using a horseradish peroxidase conjugated anti-RSV F MAb targeting the C site of RSV F (1331H) (Beeler and van Wyke Coelingh, J Virol. 63(7): 2941-2950 (1989). 1331H MAb was diluted 1:6,000 in PBS and 30 μl was added to each well. Following two hours of incubation at 37° C., the plates were washed three times with PBS-T. TMB peroxidase 30 μL was added to each well and the plates were incubated at room temperature in the dark for 15 minutes. The reaction was stopped by the addition of 15 μL of 2N H2SO4 to each well. Substrate turnover was measured by monitoring absorbance at 450 nm using a microplate reader. IC50 values were calculated using a non-linear fit algorithm in Graphpad Prism using the log (inhibitor) vs. response with variable slope curve fit and represent the concentration of MAb required for a 50% reduction in absorbance measured at 450 nm.

Figure 25:
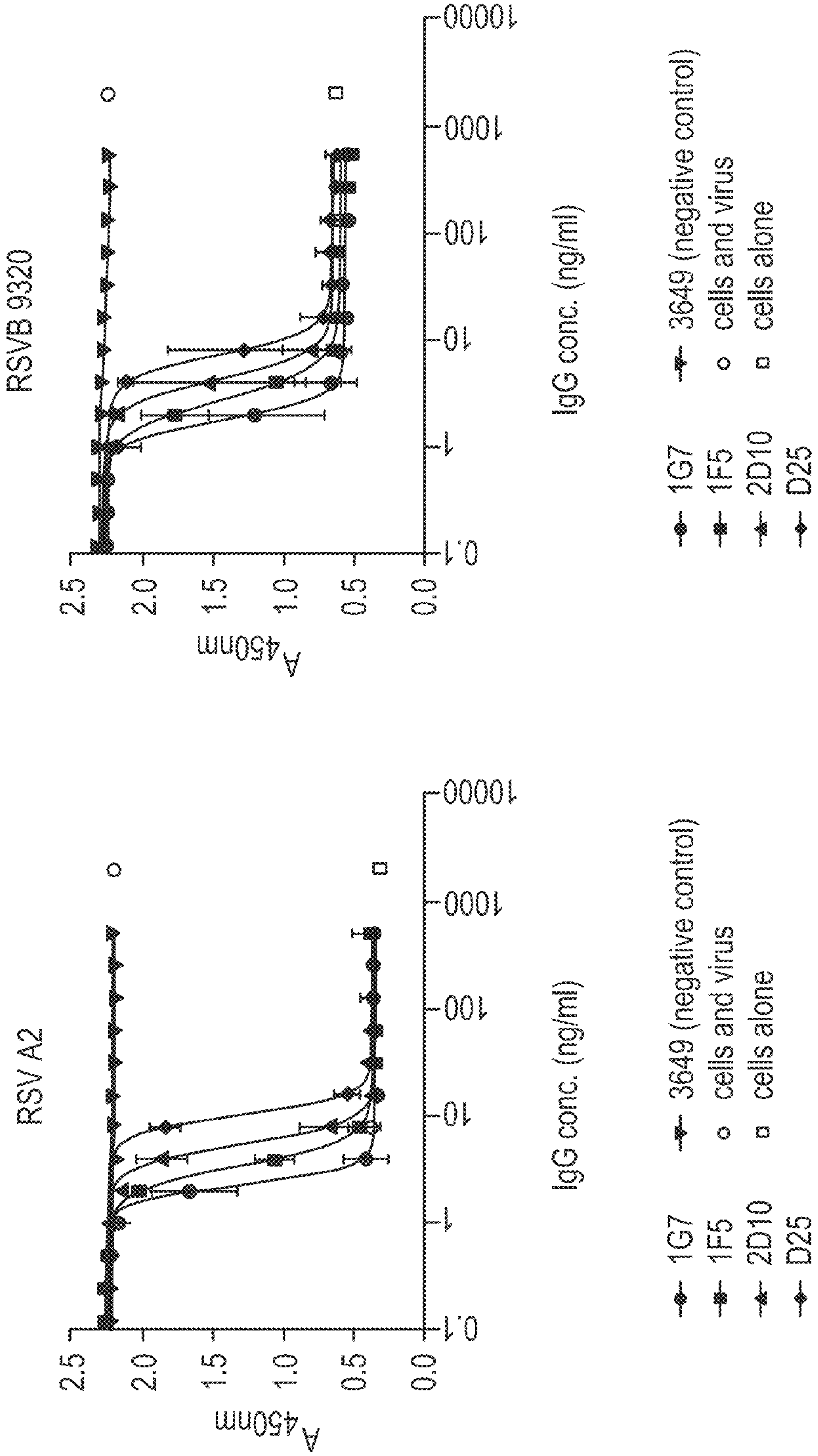
FIG. 25 shows in vitro neutralization of RSV A2 (left panel) and RSVB 9320 (right panel) by various antibodies including nirsevimab (1G7), 1F5, 2D10, and D25 each inhibited RSV A2 and RSV B9320 as measured in a microneutralization assay.

Results are provided in FIG. 25, which shows that nirsevimab, 1F5, 2D10, and D25 each inhibited RSV A2 and RSV B9320 replication in the microneutralization. The sequences of the variable regions of each of these antibodies are shown in Table 20A and Table 20B. Nirsevimab was the most effective, followed by 1F5, 2D10, and then D25.

TABLE 20A

| Light Chain Variable Region | |
|---|---|
| DIQMTQSPSS LSAAVGDRVT ITCQASQDIV<br>NYLNWYQQKP GKAPKLLIYV ASNLETGVPS<br>RFSGSGSGTD FSLTISSLQP EDVATYYCQQ<br>YDNLPLTFGG GTKVEIK | SEQ ID NO: 9 |

TABLE 20B

| | Heavy Chain Variable Region | |
|---|---|---|
| D25 | QVQLVQSGAE VKKPGSSVMV SCQASGGPLR NYIINWLRQA PGQGPEWMGG<br>IIPVLGTVHY APKFQGRVTI TADESTDTAY IHLISLRSED TAMYYCATET<br>ALVVSTTYLP HYFDNWGQGT LVTVSS | SEQ ID NO: 13 |
| Nirsevimab | QVQLVQSGAE VKKPGSSVMV SCQASGGLLE DYIINWVRQA PGQGPEWMGG<br>IIPVLGTVHY GPKFQGRVTI TADESTDTAY MELSSLRSED TAMYYCATET<br>ALVVSETYLP HYFDNWGQGT LVTVSS | SEQ ID NO: 10 |
| 1F5 | QVQLVQSGAE VKKPGSSVMV SCQASGGPLE DYIINWVRQA PGQGPEWMGG<br>IIPVLGTVHY GPKFQGRVTI TADESTDTAY MELSSLRSED TAMYYCATET<br>ALVVSTTYLP HYFDNWGQGT LVTVSS | SEQ ID NO: 14 |
| 2D10 | QVQLVQSGAE VKKPGSSVMV SCQASGGPLE DYIINWVRQA PGQGPEWMGG<br>IIPVLGTVHY GPKFQGRVTI TADESTDTAY MELSSLRSED TAMYYCATET<br>ALVVSTTYRP HYFDNWGQGT LVTVSS | SEQ ID NO: 15 |

Example 4

The cotton rat model was used as described in WO 2015/011391. Variants of nirsevimab (1G7-GLM, B12-1, E3-5, and E9-2) were made to alter the isoelectric point (pI) by incorporating germline residues in the heavy chain of the antibody. Sequences of the heavy chain variable regions of those variants are shown in Table 21; residues designated with a "~" represent modifications made relative to nirsevimab.

The concentrations of human IgG in cotton rat serum samples on the day of lung harvest were determined using an ELISA method. The human antibodies were captured by a goat anti-human antibody bound to microtiter plates. The goat anti-human IgG (H+L) antibody (0.5 μg/mL in 1×PBS) was coated onto Nunc Maxisorp 384 well microtiter plates overnight at 4° C. in a 30 μL volume. Plates were washed then blocked with 60 μL of a solution of PBS+3% heat inactivated goat serum for 1 hour at room temperature. The blocking buffer was removed and samples were applied as follows: A two-fold serial dilution of the standard human antibody diluted in assay buffer was used for the standard curve with a concentration range of 500 ng/ml to 0.488 ng/ml. Standard curves were fitted using a 4 parameter curve fit.

Figure 26:
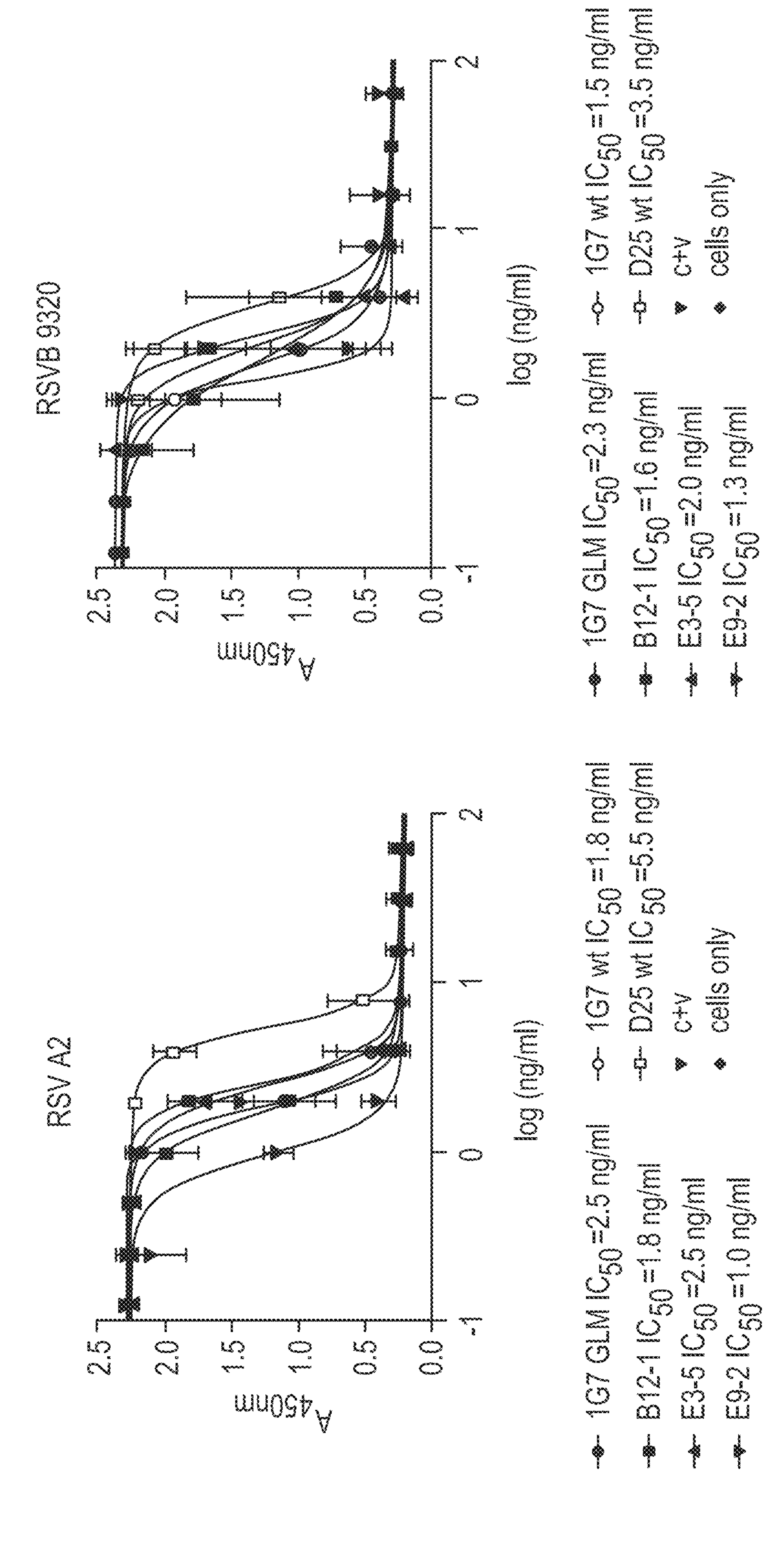
FIG. 26 shows in vitro neutralization of RSV A2 (left panel) and RSVB 9320 (right panel) by various antibodies including D25, nirsevimab (1G7), and variants of nirsevimab (1G7-GLM, B12-1, E3-5, and E9-2) as measured in a microneutralization assay (c+v=cells plus virus).

Results are provided in FIG. 26, showing that the variants described herein have lower IC50s than D25 in neutralizing both RSV A2 and RSV B9320. This also demonstrates that there was no loss of activity against the A2 or B9320 virus with increased activity seen with E9-2 and B12-1 and only a nominal loss of activity against the B9320 virus with 1G7 GLM and E3-5.

TABLE 21

| | | |
|---|---|---|
| 1G7-GLM | 1G7-GLM (pI 7.31)<br>QVQLVQSGAEVKKPGSSVKVSCKASGGLLEDYIINWVRQAPGQGPEWMGGIIPVLG<br>TVHYGPKFQGRVTITADESTSTAYMHLSSLRSEDTAMYYCARETALVVSTTYLPHY<br>FDNWGQGTLVTVSS | SEQ ID NO: 16 |
| B12-1 | B12-1 (pI 6.97)<br>QVQLVQSGAEVKKPGSSVKVSCKASGGLLEDYIINWVRQAPGQGPEWMGGIIPVLG<br>TVHYGPKFQGRVTITADESTDTAYMHLSSLRSEDTAMYYCATETALVVSTTYLPHY<br>FDNWGQGTLVTVSS | SEQ ID NO: 17 |
| E3-5 | E3-5 (pI 6.94)<br>QVQLVQSGAEVKKPGSSVKVSCKASGGLLEDYIINWVRQAPGQGPEWMGGIIPVLG<br>TVHYGPKFQGRVTITADESTSTAYMELSSLRSEDTAMYYCATETALVVSTTYLPHY<br>FDNWGQGTLVTVSS | SEQ ID NO: 18 |

TABLE 21-continued

E9-2    E9-2 (pI 7.13)                                              SEQ ID NO: 19

QVQLVQSGAEVKKPGSSVKVSCKASGGLLEDYIINWVRQAPGQGPEWMGGIIPVLG

TVHYGPKFQRVTITADESTSTAYMHLSSLRSEDTAMYYCATETALVVSTTYLPHY
FDNWGQGTLVTVSS

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of preventing Respiratory Syncytial Virus (RSV) lower respiratory tract infection (LRTI) in a subject by administering to the subject a single fixed dose of an anti-RSV monoclonal antibody or an antigen-binding fragment thereof, wherein the single fixed dose is in a pharmaceutical composition, wherein the anti-RSV monoclonal antibody or antigen-binding fragment comprises a light chain variable region comprising a CDR-L1 of SEQ ID NO: 3, a CDR-L2 of SEQ ID NO: 4, and a CDR-L3 of SEQ ID NO: 5, and a heavy chain variable region comprising a CDR-H1 of SEQ ID NO: 6, a CDR-H2 of SEQ ID NO: 7, and a CDR-H3 of SEQ ID NO: 8; and wherein (i) if the subject weighs <5 kg, and is in the first year of life and/or is entering or experiencing their first RSV season, the single fixed dose is 50 mg;

(ii) if the subject weighs 5 kg, and is in the first year of life and/or is entering or experiencing their first RSV season, the single fixed dose is 100 mg; and (iii) if the subject is in the second year of life and/or is entering or experiencing their second RSV season, and the subject is at high risk of severe RSV infection, the single fixed dose is 200 mg.

2. The method of claim 1, wherein the subject at high risk of severe RSV infection has chronic lung disease, congenital heart disease, Down's Syndrome, primary immunodeficiency, and/or acquired immunodeficiency.

3. The method of claim 1, wherein the subject in the first year of life and/or entering or experiencing their first RSV season has chronic lung disease, congenital heart disease, Down's Syndrome, primary immunodeficiency, and/or acquired immunodeficiency.

4. The method of claim 1, wherein the subject in the second year of life and/or entering or experiencing their second RSV season weighs 5 kg.

5. The method of claim 1, wherein the subject weighs 5 kg and is in the first year of life and the single fixed dose is 100 mg; or the subject is in the second year of life and the single fixed dose is 200 mg.

6. The method of claim 1, wherein the subject weighs 5 kg and is entering or experiencing their first RSV season and the single fixed dose is 100 mg; or the subject is entering or experiencing their second RSV season and the single fixed dose is 200 mg.

7. The method of claim 1, wherein the subject weighs <5 kg, is in the first year of life, and is entering their first RSV season, and the single fixed dose is 50 mg; or the subject weighs ≥5 kg, is in the first year of life, and is entering their first RSV season, and the single fixed dose is 100 mg.

8. The method of claim 1, wherein the anti-RSV monoclonal antibody or antigen-binding fragment comprises a light chain variable region comprising SEQ ID NO: 9 and a heavy chain variable region comprising SEQ ID NO: 10.

9. The method of claim 1, wherein the anti-RSV monoclonal antibody is nirsevimab.

10. The method of claim 1, wherein the anti-RSV monoclonal antibody or antigen-binding fragment is present in the pharmaceutical composition at a concentration of 100 mg/mL.

11. The method of claim 10, wherein the pharmaceutical composition further comprises:

an ionic excipient comprising 50 mM to 150 mM arginine or lysine, a buffer comprising 20 mM to 50 mM histidine, a sugar comprising 100 mM to 140 mM sucrose, and a surfactant comprising 0.01% (w/v) to 0.05% (w/v) polysorbate-80;

wherein the pharmaceutical composition has a pH of 5.5 to 6.5.

12. The method of claim 11, wherein:

the ionic excipient comprises 80 mM L-arginine hydrochloride, the buffer comprises 30 mM L-histidine, L-histidine hydrochloride, or a combination thereof, the sugar comprises 120 mM sucrose, the surfactant comprises 0.02% (w/v) or 0.04% (w/v) polysorbate-80, and the pharmaceutical composition has a pH of 5.5 to 6.5.

13. The method of claim 1, wherein preventing RSV LRTI comprises preventing medically attended RSV-confirmed LRTI or preventing RSV LRTI hospitalization.

14. The method of claim 1, wherein the amount of the single fixed dose is selected to maintain nirsevimab serum concentrations in the subject above an $AUC_{0-\infty}$ of 13.4 day·mg/mL.

15. The method of claim 1, wherein the method comprises administering the pharmaceutical composition intramuscularly.

16. The method of claim 1, wherein the method comprises administering the pharmaceutical composition at the beginning of the RSV season.

17. The method of claim 1, wherein the method comprises administering the pharmaceutical composition in combination with at least one other agent.

18. The method of claim 17, wherein the at least one other agent comprises an anti-viral agent.

* * * * *

UNITED STATES PATENT AND TRADEMARK OFFICE

CERTIFICATE OF CORRECTION

PATENT NO. : 12,024,553 B2
APPLICATION NO. : 16/859750
DATED : July 2, 2024
INVENTOR(S) : Anis Ahmed Khan et al.

It is certified that error appears in the above-identified patent and that said Letters Patent is hereby corrected as shown below:

In the Claims

Claim 1, Column 73, Line 36, "if the subject weighs 5 kg" should read --if the subject weighs ≥ 5 kg--.

Claim 4, Column 73, Line 54, "weighs 5 kg" should read --weighs ≥ 5 kg--.

Claim 5, Column 73, Lines 55-56, "wherein the subject weighs 5 kg" should read --wherein the subject weighs ≥ 5 kg--.

Claim 6, Column 73, Lines 59-60, "wherein the subject weighs 5 kg" should read --wherein the subject weighs ≥ 5 kg--.

Claim 10, Column 74, Lines 27-28, "100 mg/m L" should read --100 mg/mL--.

Claim 14, Column 74, Line 54, "day·mg/m L" should read --day·mg/mL--.

Signed and Sealed this
Seventh Day of January, 2025

Derrick Brent
*Acting Director of the United States Patent and Trademark Office*